United States Patent
Alvarez et al.

(10) Patent No.: US 9,623,160 B2
(45) Date of Patent: Apr. 18, 2017

(54) QUANTIFICATION AND INVENTORY MANAGEMENT OF EXPRESSED HUMAN BREAST MILK

(71) Applicant: Naya Health, Inc., Redwood City, CA (US)

(72) Inventors: Jeffery B. Alvarez, Redwood City, CA (US); Janica B. Alvarez, Redwood City, CA (US); Nathaniel Gaskin, Palo Alto, CA (US); Polina A. Segalova, Redwood City, CA (US)

(73) Assignee: Naya Health, Inc., Redwood City, CA (US)

( * ) Notice: Subject to any disclaimer, the term of this patent is extended or adjusted under 35 U.S.C. 154(b) by 0 days.

(21) Appl. No.: 14/858,924

(22) Filed: Sep. 18, 2015

(65) Prior Publication Data

US 2016/0082165 A1     Mar. 24, 2016

Related U.S. Application Data

(60) Provisional application No. 62/052,941, filed on Sep. 19, 2014.

(51) Int. Cl.
G06F 17/00 (2006.01)
A61M 1/06 (2006.01)
G06Q 10/08 (2012.01)

(52) U.S. Cl.
CPC ............. *A61M 1/062* (2014.02); *A61M 1/06* (2013.01); *G06Q 10/087* (2013.01); *A61M 2205/071* (2013.01); *A61M 2205/3393* (2013.01); *A61M 2205/502* (2013.01); *A61M 2205/6072* (2013.01)

(58) Field of Classification Search
CPC ...... G06Q 30/02; G06Q 10/087; G06Q 10/08; G06Q 7/1008
USPC .................................................. 235/375, 380
See application file for complete search history.

(56) References Cited

U.S. PATENT DOCUMENTS

| | | |
|---|---|---|
| 4,263,912 A | 4/1981 | Adams |
| 5,423,781 A | 6/1995 | Alexander et al. |
| 5,885,246 A | 3/1999 | Ford |
| 6,383,163 B1 | 5/2002 | Kelly et al. |
| 6,616,037 B2 | 9/2003 | Grimm et al. |
| 6,652,484 B1 | 11/2003 | Hunckler et al. |
| 6,673,036 B1 | 1/2004 | Britto |
| 6,749,582 B2 | 6/2004 | Britto et al. |
| 6,840,918 B1 | 1/2005 | Britto et al. |
| 6,887,210 B2 | 5/2005 | Quay |
| 7,029,454 B2 | 4/2006 | Watanabe |
| 7,118,709 B2 | 10/2006 | Treptow |

(Continued)

OTHER PUBLICATIONS

International search report and written opinion dated Dec. 18, 2015 for PCT/US2015/051078.

*Primary Examiner* — Karl D Frech
(74) *Attorney, Agent, or Firm* — Wilson Sonsini Goodrich & Rosati

(57) ABSTRACT

Systems, methods, and devices for milk expression are provided. In one aspect, a system includes an expression apparatus having an interface configured to engage a breast and an actuation assembly operably coupled to the interface. Actuation of the actuation assembly causes the interface to apply vacuum pressure against the breast to express milk from the breast. The system also includes various sensors for quantifying characteristics of the expressed milk, and a unique identifier allows inventory management of the expressed milk.

51 Claims, 39 Drawing Sheets

(56) References Cited

U.S. PATENT DOCUMENTS

| | | |
|---|---|---|
| 7,662,127 B2 | 2/2010 | Silver et al. |
| 7,758,540 B2 | 7/2010 | Yamashita et al. |
| 7,875,000 B2 | 1/2011 | Krebs et al. |
| 7,972,297 B2 | 7/2011 | Bryan et al. |
| 8,116,933 B2 | 2/2012 | Underdal et al. |
| 8,118,772 B2 | 2/2012 | Dao et al. |
| 8,164,454 B2 | 4/2012 | Teller |
| 8,216,179 B2 | 7/2012 | Bosshard et al. |
| 8,323,235 B2 | 12/2012 | Bryan et al. |
| 8,453,878 B2 | 6/2013 | Palmquist |
| 8,801,658 B2 | 8/2014 | Horari et al. |
| 8,813,551 B2 | 8/2014 | Boiarski |
| 8,827,947 B2 | 9/2014 | Bosman et al. |
| 8,876,760 B2 | 11/2014 | Bosman et al. |
| 9,033,953 B2 | 5/2015 | Felber |
| 2005/0234370 A1 | 10/2005 | Beal et al. |
| 2006/0042376 A1 | 3/2006 | Reusche et al. |
| 2007/0125162 A1 | 6/2007 | Ghazi et al. |
| 2010/0217148 A1 | 8/2010 | Binder |
| 2013/0096461 A1 | 4/2013 | Sella |
| 2013/0131588 A1 | 5/2013 | Silver et al. |
| 2013/0245548 A1 | 9/2013 | Cook et al. |
| 2014/0121593 A1 | 5/2014 | Felber et al. |
| 2014/0262918 A1 | 9/2014 | Chu |
| 2014/0263611 A1 | 9/2014 | Bauer |
| 2014/0276629 A1 | 9/2014 | Bauer et al. |
| 2014/0288466 A1 | 9/2014 | Alvarez et al. |
| 2015/0038945 A1 | 2/2015 | McCabe |
| 2015/0051458 A1 | 2/2015 | Chen et al. |
| 2015/0122688 A1 | 5/2015 | Dias et al. |
| 2015/0265753 A1 | 9/2015 | Prentice et al. |
| 2015/0274329 A1 | 10/2015 | Harp et al. |
| 2015/0283311 A1 | 10/2015 | Alvarez et al. |
| 2015/0314053 A1 | 11/2015 | Furrer et al. |
| 2015/0328380 A1 | 11/2015 | Furrer et al. |

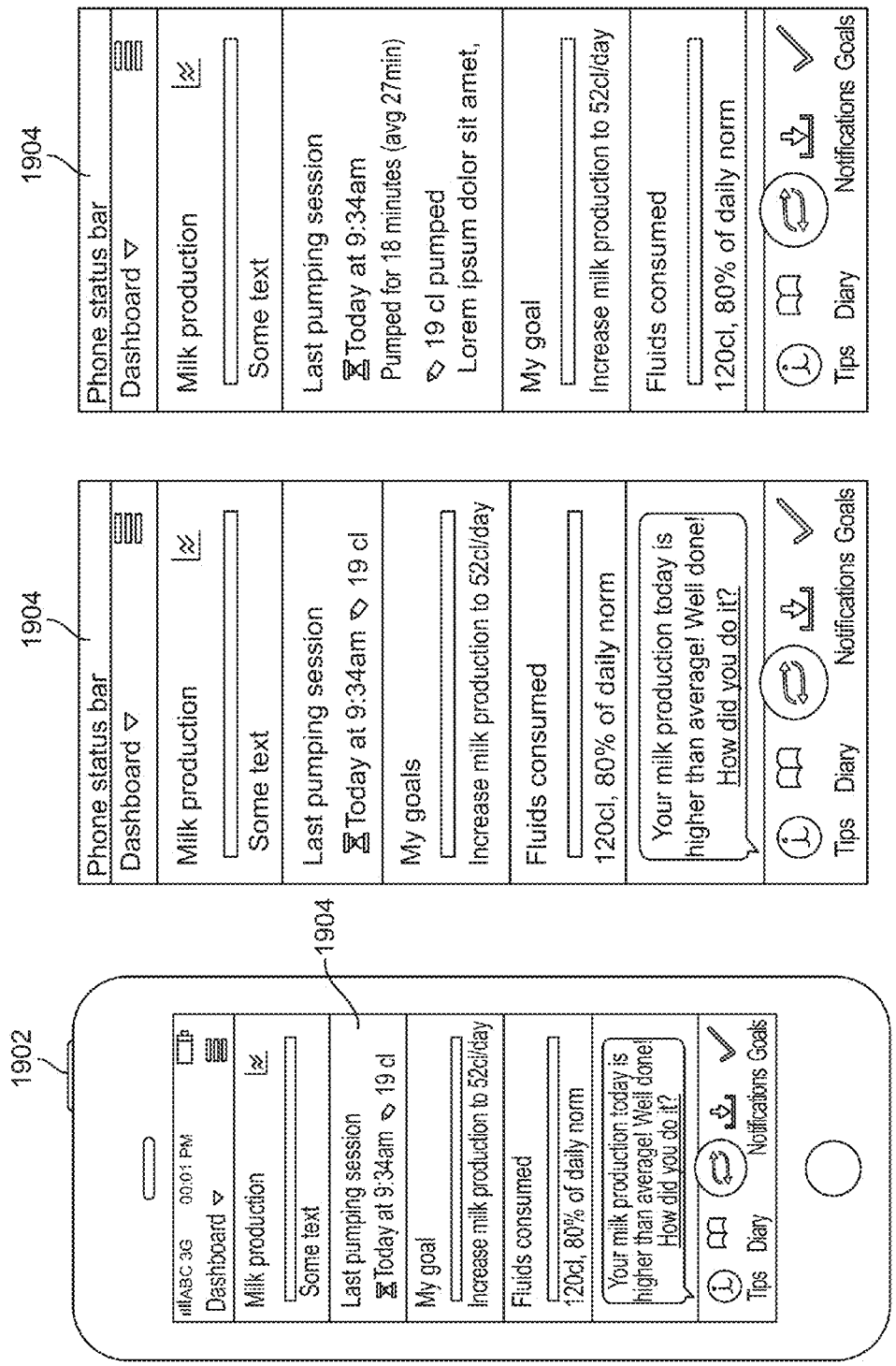

QUANTIFICATION AND INVENTORY MANAGEMENT OF EXPRESSED HUMAN BREAST MILK

CROSS-REFERENCE

The present application is a non-provisional of, and claims the benefit of U.S. Provisional Patent Application No. 62/052,941, filed on Sep. 19, 2014, the entire contents of which are incorporated herein by reference.

This application is related to the following co-pending provisional and non-provisional patent applications: U.S. patent application Ser. No. 14/221,113, U.S. patent application Ser. No. 14/616,557, U.S. patent application Ser. No. 14/793,606, U.S. patent application Ser. No. 14/793,613, and U.S. patent application Ser. No. 14/793,617, the entire contents of which are incorporated herein by reference.

BACKGROUND OF THE INVENTION

1. Field of the Invention

The present invention generally relates to medical devices and methods, and more particularly relates to devices and methods for expression and collection of human breast milk. Such devices and methods preferably facilitate quantification of properties of the expressed milk as well as inventory control of the expressed milk.

Breast pumps are commonly used to collect breast milk in order to allow mothers to continue breastfeeding while apart from their children. It would be desirable to provide breast pumps that not only collect the milk, but that can provide additional information about the expressed milk. Additional features such as quantification of milk production and nutritional information as well as inventory management are further desirable for enhanced user convenience. Managing the inventory of expressed breast milk can pose challenges for the user, because of the fluctuating supply and demand for the milk over time and the limited shelf-life of expressed breast milk. It would be desirable to provide a way for users to automatically keep track of the expressed milk inventory, to manage the inventory, and even forecast both future consumption and production. It would also be desirable to provide quantitative information that characterizes the nutritional information about the expressed milk.

At least some of these objectives will be satisfied by the devices and methods disclosed below.

2. Description of the Background Art

The following US patents are related to expression and collection of human breast milk: U.S. Pat. Nos. 6,673,036; 6,749,582; 6,840,918; 6,887,210; 7,875,000; 8,118,772; and 8,216,179.

SUMMARY OF THE INVENTION

The present invention generally relates to medical devices and methods, and more particularly relates to devices and methods for expression and collection of human breast milk.

In one aspect, a system for quantifying expressed milk from a human breast comprises a breast milk expression device configured to express milk from the breast and a reservoir fluidly coupled to the breast milk expression device, configured to collect the expressed breast milk. The reservoir comprises a unique identifier. The system further comprises a sensor unit configured to quantify one or more attributes of the expressed breast milk. The system further comprises a peripheral device in communication with the sensor unit, wherein the peripheral device is configured to associate the one or more attributes of the expressed milk quantified by the sensor unit with the unique identifier of the reservoir containing the expressed breast milk.

In any embodiment of the system, the sensor unit may be integrated with the reservoir and configured to quantify the one or more attributes of the expressed breast milk as the expressed breast milk is collected into the reservoir. Additionally or alternatively, the sensor unit may be integrated with the breast milk expression device and configured to quantify the one or more attributes of the expressed breast milk as the expressed breast milk is collected into the reservoir. Additionally or alternatively, the sensor unit may comprise a separate sensor unit in communication with the peripheral device, the separate sensor unit configured to quantify one or more attributes of the expressed breast milk after the expressed breast milk has been collected in the reservoir.

The one or more attributes of the expressed breast milk quantified by the sensor unit may comprise a volume of the expressed breast milk collected in the reservoir. Additionally or alternatively, the one or more attributes may comprise a composition of the expressed milk, wherein the sensor unit is configured to quantify the relative amount of one or more compounds present in the expressed breast milk.

In any embodiment of the system, the breast milk expression device may be configured to generate pump session data comprising a start time of a pump session and an end time of the pump session. The peripheral device may be further configured to associate the pump session data with the unique identifier of the reservoir.

In any embodiment of the system, the peripheral device may be further configured with instructions to update an inventory of expressed breast milk in response to the association of the one or more attributes of the expressed milk with the unique identifier of the reservoir containing the expressed breast milk. The peripheral device may be configured to generate an inventory item in the inventory of expressed breast milk corresponding to the unique identifier of the reservoir containing the expressed breast milk.

The unique identifier may comprise one or more of a human-readable code, a barcode, a Quick Response (QR) code, and a radio-frequency identification (RFID) tag.

In any embodiment of the system, the system may further comprise a label printer for generating a label for the reservoir comprising the unique identifier. The label printer may be configured to communicate with the peripheral device and provide the unique identifier to the peripheral device when the label is generated.

In another aspect, a method for quantifying expression of breast milk from a human breast comprises expressing breast milk from a human breast using a breast milk expression device, and collecting the expressed breast milk into a reservoir fluidly coupled to the breast milk expression device. The method further comprises quantifying one or more attributes of the expressed breast milk with a sensor unit and generating pump session data comprising a start time of expression of the breast milk and an end time of the expression. The method further comprises digitally associating the pump session data with the one or more attributes of the expressed milk. The method further comprises updating a pump session log with the pump session data, wherein the pump session log is stored on a peripheral device in communication with the breast milk expression device.

The quantifying may comprise quantifying the one or more attributes of the expressed breast milk as the expressed breast milk is collected into the reservoir. Additionally or alternatively, the quantifying may comprise quantifying the one or more attributes of the expressed breast milk after the expressed breast milk has been collected in the reservoir. The quantifying may comprise quantifying a volume of the expressed breast milk collected in the reservoir, a relative amount of one or more compounds present in the expressed breast milk, or a combination thereof.

The method may further comprise feeding the expressed breast milk to a child, and determining a volume of expressed breast milk consumed by the child. The method may further comprise updating a feed log stored on the peripheral device to add feeding session data, wherein the feeding session data comprises a time of the feeding and the volume of consumed breast milk.

In any embodiment of the method, the reservoir may comprise a unique identifier, and the method may further comprise providing the unique identifier to the peripheral device. The method may further comprise digitally associating the unique identifier with the pump session data and the one or more attributes of the expressed milk.

The unique identifier may comprise a human-readable code, wherein providing the unique identifier to the peripheral device may comprise prompting a user to input the human-readable code via an application of the peripheral device. Additionally or alternatively, the unique identifier may comprise a machine-readable code, wherein providing the unique identifier to the peripheral device may comprise reading the machine-readable code with a machine configured to recognize the machine-readable code. The machine-readable code may comprise a radio-frequency identification (RFID) tag, and providing the unique identifier to a peripheral device may comprise scanning the RFID tag with an RFID reader in communication with the peripheral device.

The method may further comprise updating an inventory of expressed breast milk to add a new inventory item corresponding to the unique identifier of the reservoir containing the expressed breast milk.

The method may further comprise transferring the expressed milk from the reservoir to another storage reservoir comprising a unique identifier.

In another aspect, a system for managing an inventory of expressed breast milk comprises a reservoir containing expressed breast milk, wherein the reservoir comprises a unique identifier. The system further comprises an inventory management database comprising one or more inventory items, each inventory item associated with a unique identifier of a reservoir. The system further comprises a computing device configured with instructions to receive the unique identifier of the reservoir, receive one or more attributes of the expressed breast milk digitally associated with the unique identifier, and update the inventory management database in response to receiving the unique identifier.

In any embodiment of the system, the one or more attributes of the expressed breast milk may comprise a date and time of expression of the expressed breast milk.

In any embodiment of the system, the computing device may be further configured to sort the one or more inventory items in the inventory management database in order of first-to-feed to last-to-feed. The computing device may be further configured to display the inventory management database to a user. The computing device may be further configured to locally store the inventory management database.

Any embodiment of the system may further comprise a server in communication with the computing device, the server configured to remotely store the inventory management database.

In any embodiment of the system, the unique identifier may comprise a Quick Response (QR) code, and the computing device may be further configured to recognize the QR code. Alternatively or additionally, the unique identifier may comprise a radio-frequency identification (RFID) tag, wherein the system may further comprise an RFID reader in communication with the computing device. The RFID reader may be configured to recognize the RFID tag and provide identifier information to the computing device.

Any embodiment of the system may further comprise a reservoir organizer configured to store a plurality of reservoirs in a stacked configuration. The organizer may comprise a top opening configured to receive the plurality of reservoirs one at a time, and a bottom opening configured to allow withdrawal of a reservoir disposed at the bottom of a stack of the plurality of reservoirs, thereby facilitating a first-in, first-out system of organization. Optionally, the reservoir organizer may further comprise an integrated RFID reader configured to scan an RFID tag disposed on a storage reservoir as the storage reservoir enters or exits the reservoir organizer. The RFID reader may communicate detected scans to the computing device. Optionally, the reservoir organizer may further comprise an integrated weight sensor configured to measure a weight of the stack of the plurality of reservoirs. The weight sensor may communicate detected changes in the weight of the stack to the computing device.

In another aspect, a method for managing an inventory of expressed breast milk comprises identifying, from an inventory of expressed breast milk, an inventory item associated with a unique identifier of a reservoir containing expressed breast milk. The method further comprises updating the inventory of expressed breast milk with respect to the identified inventory item. The inventory may be locally stored on a computing device, wherein the computing device may be configured with instructions to provide an inventory management application.

In any embodiment of the method, the unique identifier may be digitally associated with pump session data for the expressed breast milk contained in the reservoir. The pump session data may comprise a date and time of expression of the expressed breast milk. Additionally or alternatively, the unique identifier may be digitally associated with one or more attributes of the expressed breast milk contained in the reservoir.

Identifying an inventory item may comprise obtaining the unique identifier of the reservoir selected and removed from storage by a user. Identifying an inventory item may comprise displaying, via the inventory management application of the computing device, a list of inventory items in the inventory, and prompting a user to select the inventory item from the list of inventory items. The method may further comprise sorting the list of inventory items in order of first-to-feed to last-to-feed. Sorting in order of first-to-feed to last-to-feed may comprise sorting in order of date of expression of the expressed breast milk, wherein an inventory item corresponding to expressed breast milk with an oldest date of expression is determined to be the first-to-feed, and an inventory item corresponding to expressed breast milk with a newest date of expression is determined to be the last-to-feed. Optionally, the method may further comprise providing, via the inventory management application of the computing device, a visual display of a plurality of reservoirs corresponding to a plurality of inventory items in the inventory, the visual display identifying the first-to-feed inventory item. Optionally, the method may further comprise indicating an inventory item as expired if a difference between a current date and a date of expression of the expressed breast milk corresponding to the inventory item exceeds a predetermined expiry threshold.

Updating the inventory may comprise removing the inventory item from the inventory in response to a determination that there is no remaining milk in the reservoir. Alternatively, updating the inventory may comprise updating information associated with the inventory item in response to a determination that there is remaining milk in the reservoir. Updating information associated with the inventory item may comprise updating a volume of the expressed breast milk contained in the reservoir, a storage location of the reservoir, or a combination thereof.

In any embodiment of the method, the inventory may be locally stored on the computing device. Additionally or alternatively, the inventory may be remotely stored on a server in communication with the computing device.

In any embodiment of the method, the unique identifier may comprise a radio-frequency identification (RFID) tag, and the method may further comprise scanning the RFID tag with an RFID reader in communication with the computing device.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 19A-19C illustrate exemplary displays on a computing device;

DETAILED DESCRIPTION OF THE INVENTION

Specific embodiments of the disclosed systems, devices, and methods will now be described with reference to the drawings. Nothing in this detailed description is intended to imply that any particular component, feature, or step is essential to the invention. Although the present invention primarily relates to breast milk, any description herein of expression and collection of breast milk can also be applied to other types of fluids expressed from other portions of the body including but not limited to colostrum fluid from the breast. Furthermore, the disclosed embodiments may be used in other applications, such as applications wherein negative pressure is used to help collect a body fluid or other specimen.

The systems, devices, and methods of the present invention provide improved pumping devices for the expression and collection of breast milk, such as human breast milk. Contrary to existing devices, the mechanisms described herein enable the development of smaller and more efficient pumping devices, thereby enhancing convenience and ease of use. Additionally, any of the exemplary embodiments disclosed herein may optionally incorporate sensors for measuring characteristics of milk expression. The resultant data can be used, for instance, as feedback for improving pumping efficiency, as well as to provide information and/or analytics relevant to milk expression to the user. Furthermore, in preferred embodiments, the data can be transmitted to another device in communication with the pumping device, thereby enabling control, display, and/or analysis of milk expression to be performed remotely.

Figure 1:
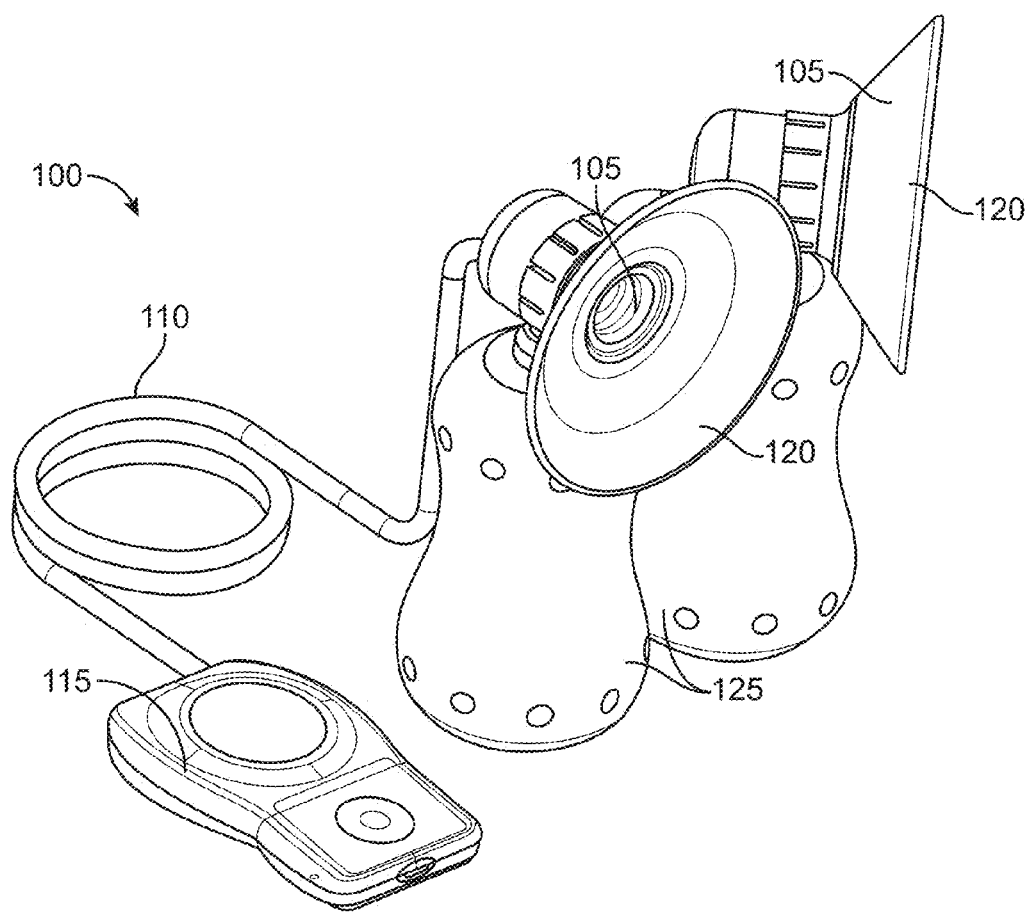
FIG. 1 is a perspective view of a pumping device, in accordance with embodiments.

FIG. 1 illustrates an exemplary embodiment of a milk expression device. Pumping device 100 (also known as an "expression apparatus" or "expression device") includes breast interfaces 105, a tube 110, and a controller 115 (sometimes also referred to as a "pendant unit") operatively coupled to breast interfaces 105 through tube 110. Breast interfaces 105 include resilient and conformable flanges 120, for engaging and creating a fluid seal against the breasts, and collection vessels 125. Controller 115 houses the power source and drive mechanism for pumping device 100, and also contains hardware for various functions, such as controlling pumping device 100, milk production quantification, and communication with other devices, as described in further detail below. Tube 110 transmits suitable energy inputs, such as mechanical energy inputs, from controller 115 over a long distance to breast interfaces 105. Breast interfaces 105 convert the energy inputs into vacuum pressure against the breasts in a highly efficient manner, resulting in the expression of milk into collection vessels 125.

Hydraulic Pumping Device

Hydraulic systems can reduce pumping force requirements, and therefore also reduce the size of the pumping device, while maintaining high pumping efficiencies. In a preferred embodiment, the pumping device can utilize a hydraulic system to generate a pressure differential against the breast for the expression and collection of milk.

Figure 2:
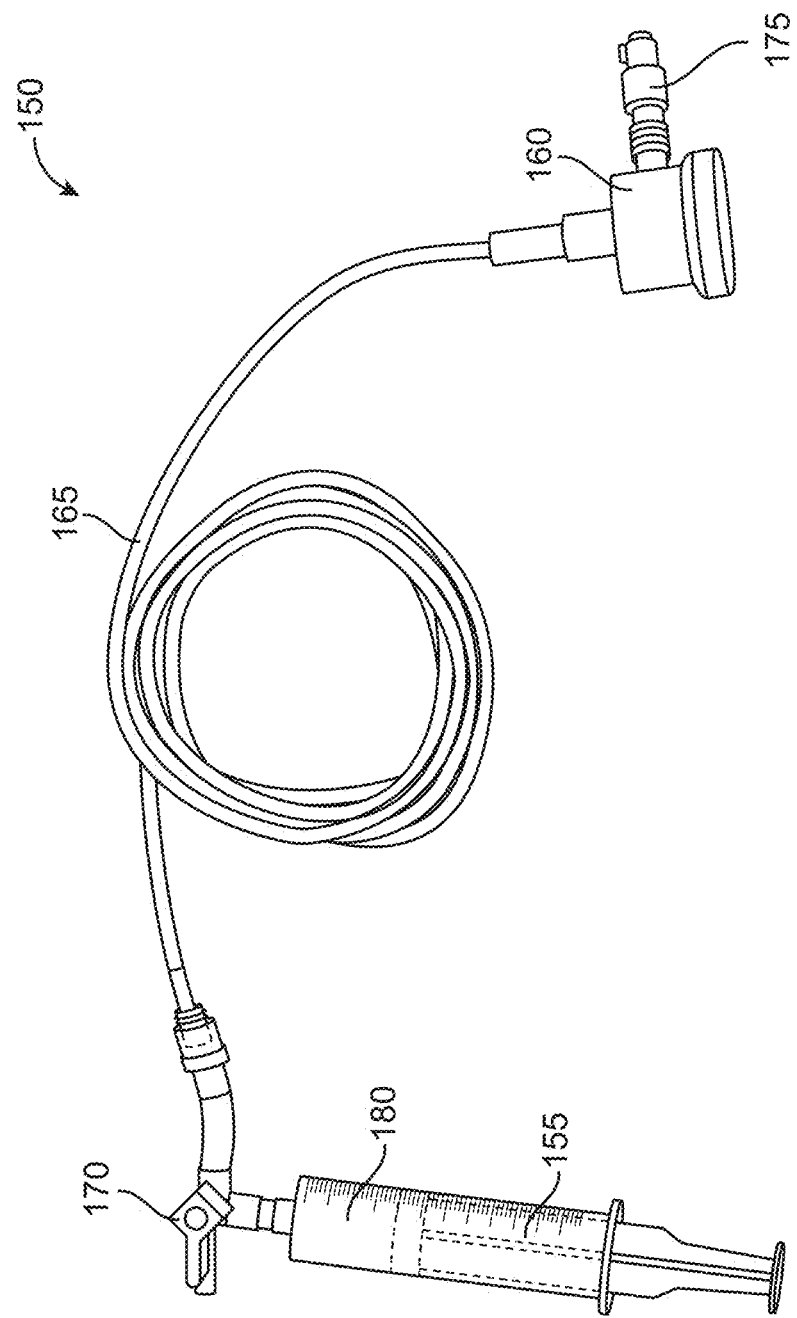
FIG. 2 is a perspective view of a hydraulic pumping device, in accordance with embodiments.
Figure 3:
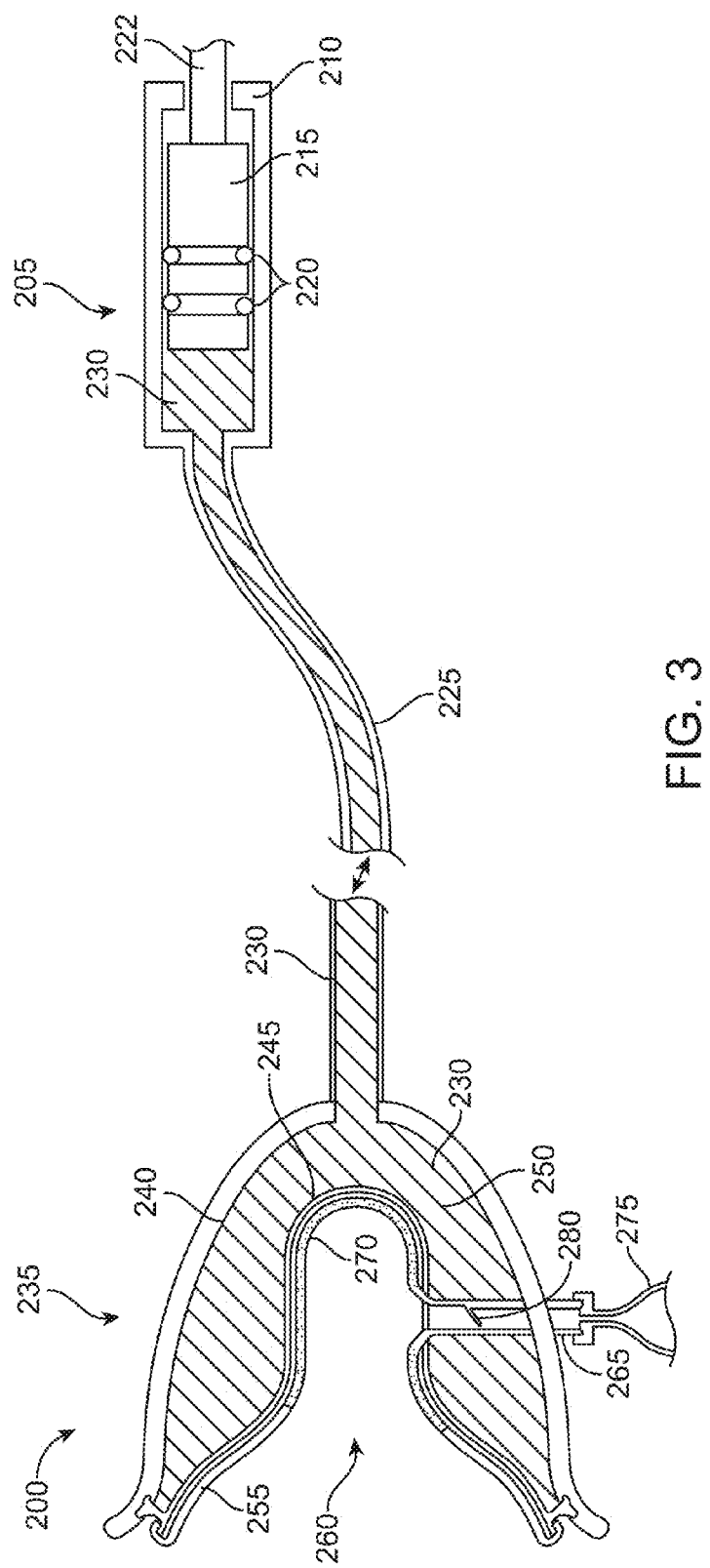
FIG. 3 is a cross-section of a hydraulic pumping device, in accordance with embodiments.

Exemplary hydraulic pumping devices are depicted in FIGS. 2 and 3. FIG. 2 illustrates a pumping device 150 with a syringe 155 fluidly coupled to breast interface 160 by tube 165. Syringe 155 is coupled to tube 165 through a three-way valve 170. Breast interface 160 contains an exit port 175. The syringe 155 drives a fluid 180 contained within tube 165 against a flexible member contained within breast interface 160 to create the pressure differential necessary for milk expression from the breast.

FIG. 3 illustrates another embodiment of a pumping device 200. The actuation assembly 205 includes an assembly housing 210, a driving element 215, radial seals 220, and a shaft 222. Driving element 215 is operatively coupled to a controller, such as controller 115, through shaft 222. The tube 225 contains a fluid 230 and is fluidly coupled to the actuation assembly 205 and the breast interface 235. The breast interface 235 consists of an interface housing 240, a flexible membrane 245, a reservoir 250, a sealing element 255, an expression area 260, and a drain port 265. The sealing element 255 includes deformable portion 270. The drain port 265 is coupled to a collection vessel 275 and includes a flap valve 280.

Actuation assembly 205 displaces fluid 230 contained within tube 225, which can be a flexible line. Fluid 230 occupies reservoir 250 within breast interface 235 and is coupled with flexible membrane 245. Preferably, the couplings between the flexible membrane 245, sealing element 255, and interface housing 240 are fluid-tight couplings, such that the fluid 230 is contained within the reservoir 250 and cannot infiltrate into the expression area 260. Flexible membrane 245 transmits vacuum pressure from fluid 230 to the deformable portion 270 of sealing element 255. When a breast is engaged into and fluidly sealed with breast interface 235 by sealing element 255, displacement of the actuation element 215 produces substantial vacuum pressure against the breast through flexible membrane 245 and deformable portion 270, resulting in the expression of breast milk into expression area 260. The expressed milk drains through drain port 265 into collection vessel 275. Drain port 265 is configured with a flap valve 280 to provide passage of milk while maintaining vacuum pressure in expression area 260. Collection vessel 275 can be any suitable container, such as a bottle or a bag. In many embodiments, collection vessel 275 is removably coupled to flexible membrane 245. Collection vessel 275 can be coupled directly or remotely via any suitable device such as extension tubing. Preferably, the collection vessel can be quickly decoupled from the other components of the pumping device 22 (e.g., for milk storage, cleaning, etc.).

The fluid for the hydraulic pumping device can be any suitable fluid, such as an incompressible fluid. In many embodiments, the incompressible fluid can be a liquid, such as water or oil. Alternatively, the fluid can be any suitable gas, such as air. Any liquid or gas suitable for use with hydraulic systems can be used for the hydraulic pumping devices described herein.

Actuation Mechanism

Many actuation mechanisms known to those of skill in the art can be utilized for the actuation assembly 205. Actuation assembly 205 can be a piston assembly, a pump such as a diaphragm pump, or any other suitable actuation mechanism. The optimal configuration for actuation assembly 205 can depend on a number of factors, such as: vacuum requirements; size, power, and other needs of the pumping device 200; and the properties of the fluid 230, such as viscosity, biocompatibility, and fluid life requirements.

FIG. 3 illustrates an exemplary embodiment in which actuation assembly 205 is a piston assembly and driving element 215 is a piston. Actuation assembly 205 includes radial seals 220, such as O-rings, sealing against assembly housing 210 to prevent undesired egress of fluid 230 and to enable driving of fluid 230.

Figure 4:
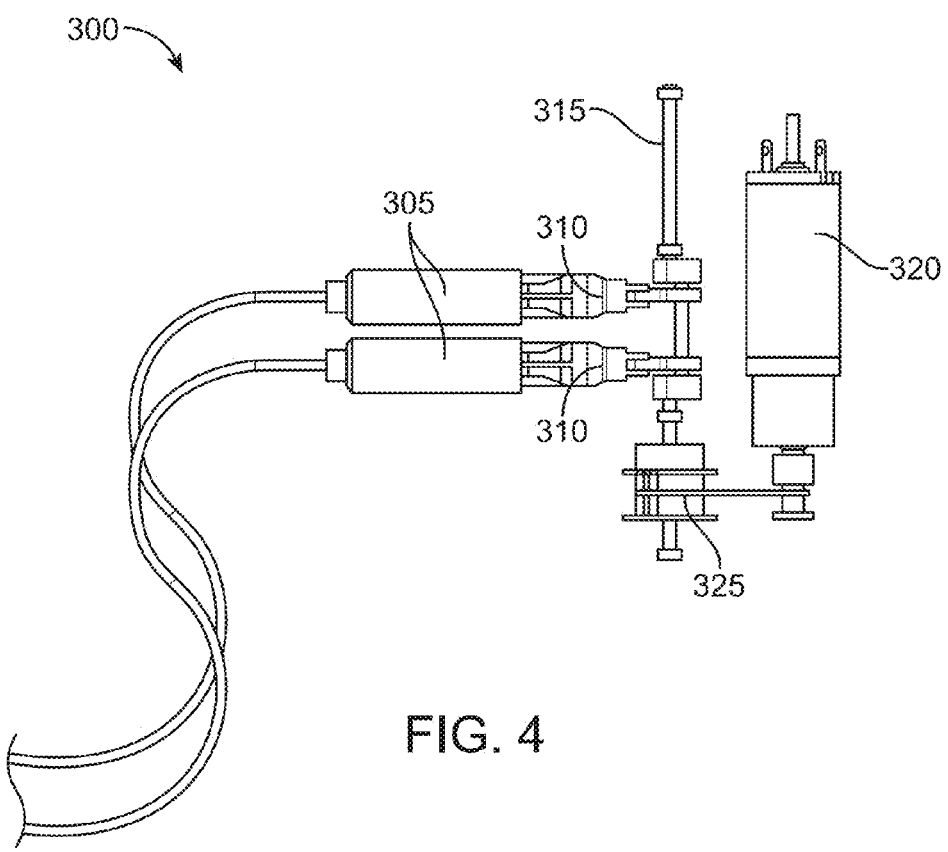
FIG. 4 illustrates an actuation assembly coupled to a driving mechanism, in accordance with embodiments.

FIG. 4 illustrates another exemplary embodiment of an actuation assembly 300 including a pair of pistons 305.

In preferred embodiments, the actuation assembly includes a driving element powered by a suitable driving mechanism, such as a driving mechanism residing in controller 115. Many driving mechanisms are known to those of skill in the art. For instance, the driving element, such as driving element 215, may be actuated electromechanically by a motor, or manually by a suitable user-operated interface, such as a lever. Various drive modalities known to those of skill in the art can be used. In particular, implementation of the exemplary hydraulic pumping devices as described herein enables the use of suitable drive modalities such as direct drive and solenoids, owing to the reduced force requirements of hydraulic systems.

Referring now to the exemplary embodiment of FIG. 4, the pistons 305 include couplings 310 to a crankshaft 315. The crankshaft 315 is operatively coupled to a motor 320 through a belt drive 325. The crankshaft 315 drives the pair of pistons 305 with the same stroke timing in order to apply vacuum pressure against both breasts simultaneously, a feature desirable for increased milk production. Alternatively, the crankshaft 315 can drive the pair of pistons 305 with any suitable stroke timing, such as alternating or offset stroke cycles.

The driving mechanism can be powered by any suitable power source, such as a local battery or an AC adaptor. The driving mechanism can be controlled by hardware, such as onboard electronics located within controller 115.

Figure 22:
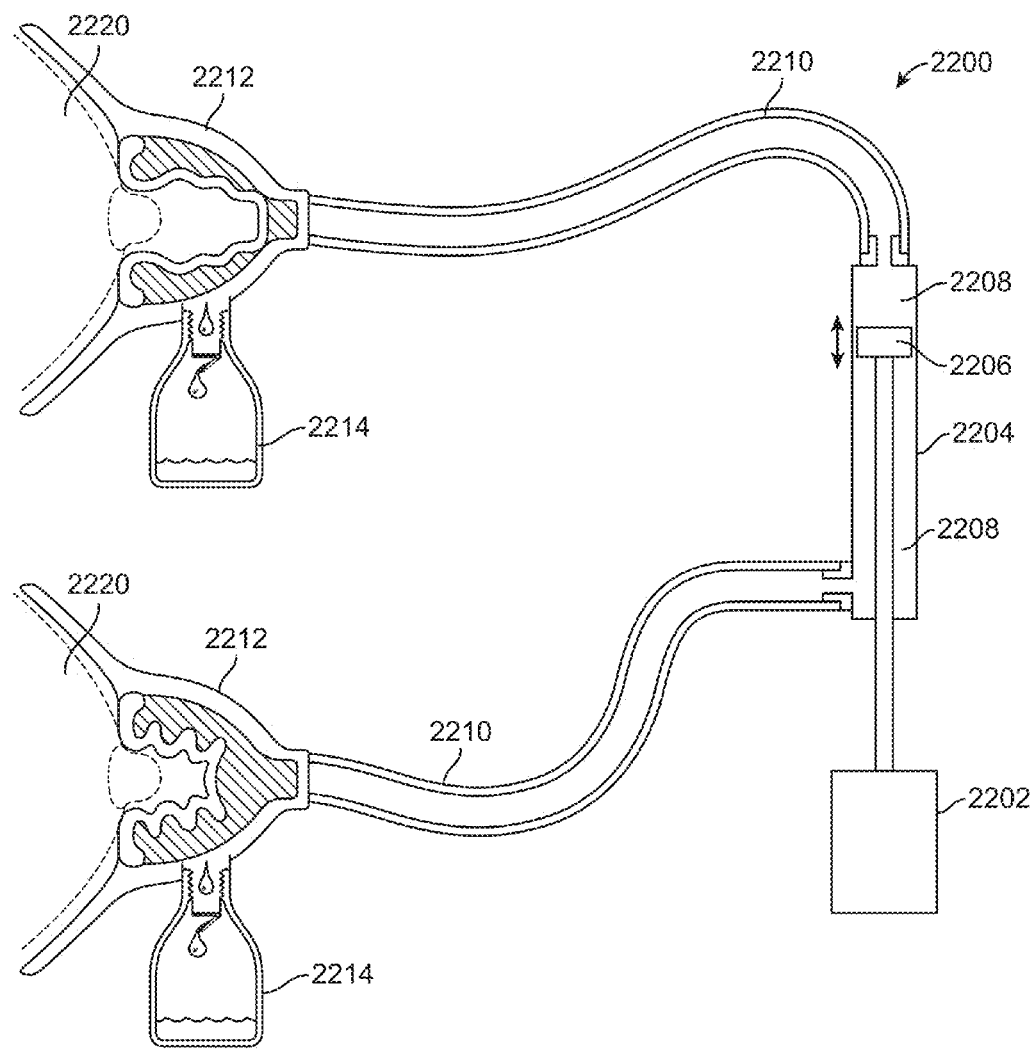
FIG. 22 illustrates a dual expression system.

FIG. 22 illustrates another embodiment of an alternating pump system 2200. The system 2200 includes dual expression devices with an interface 2212 sized and shaped to conform to the target tissue, here a breast. A reservoir 2214 is threadably or otherwise coupled to the expression device. A hydraulic line 2210 fluidly couples each expression device to a hydraulic piston assembly 2204 which has an incompressible fluid such as oil in a piston chamber and an actuatable piston 2206. One hydraulic line 2210 is coupled to the high pressure side 2208 of the hydraulic piston, and the other hydraulic line is coupled to the lower pressure side 2208 of the piston. A motor 2202 actuates the piston 2206. Thus, in operation, as the piston is actuated the high pressure side creates a higher pressure in one of the expression devices and a lower pressure in the other expression device. The lower pressure expression device results in a vacuum which creates conditions under which milk expression occurs, while the high pressure side does not express milk. Then, as the piston reaches the end of its stroke, and reciprocates in the opposite direction, the high and low pressure sides are reversed, thereby causing expression of milk on the opposite side and no expression on the original side. This process allows milk to be collected in an alternating fashion. The expression devices, reservoirs in this system may be any of the components disclosed elsewhere in this disclosure.

In any pump system comprising a pair of breast interfaces as described herein, each breast interface may be fluidly coupled to a separate hydraulic line, and each separate hydraulic line may be operably coupled to a separate actuation assembly (e.g., actuatable piston).

Figure 5A:
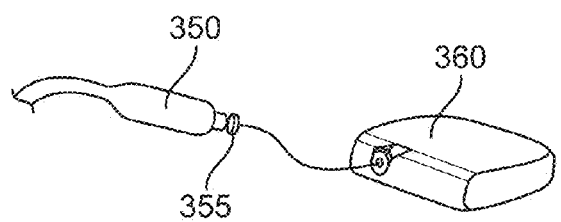
FIGS. 5A-5B illustrate an actuation assembly coupled to a controller, in accordance with embodiments.
Figure 5B:
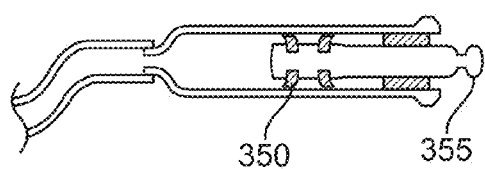

FIGS. 5A-5B illustrate an exemplary embodiment of an actuation assembly 350 that includes releasable coupling 355. FIG. 5A is a perspective view of the embodiment, and FIG. 5B is a cross-sectional view of the embodiment. Preferably, actuation assembly 350 is releasably coupled to a controller 360 and the driving mechanism housed therein. The coupling can be a mechanical coupling or any suitable quick release mechanism known to those of skill in the art. The releasably coupled design allows for flexibility in the configuration and use of the pumping device. For instance, user comfort can be improved through the use of differently sized breast interfaces for compatibility with various breast sizes. Additionally, this feature enables a common pumping device to be used with interchangeable breast interfaces, thus reducing the risk of spreading pathogens. Furthermore, the releasable coupling enables easy replacement of individual parts of the pumping device.

Flexible Membrane

In any of the embodiments, such as the embodiment depicted in FIG. 3, the flexible membrane 245 is optionally located within breast interface 235 and disposed over at least portion thereof, forming reservoir 250 between the interface housing 240 and the flexible membrane 245. Preferably, the flexible membrane 245 deforms substantially when subject to the negative pressures created when the fluid 230 is displaced from reservoir 250 by actuation assembly 205. The amount of deformation of the flexible membrane 245 can be controlled by many factors, (e.g., wall thickness, durometer, surface area) and can be optimized based on the pumping device (e.g., pump power, vacuum requirements).

Figure 6:
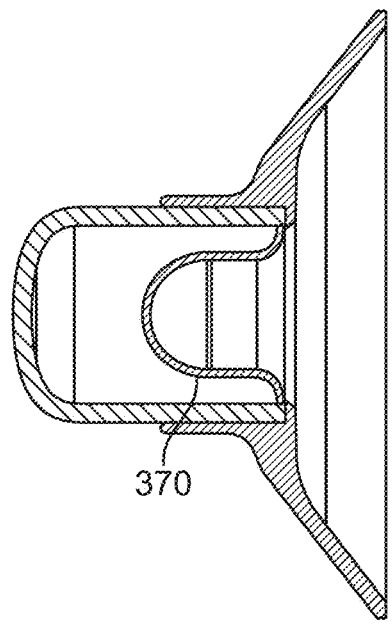
FIG. 6 is a cross-sectional view of a breast interface, in accordance with embodiments.

FIG. 6 illustrates an exemplary flexible membrane 370 with a specified thickness and durometer.

Figure 7:
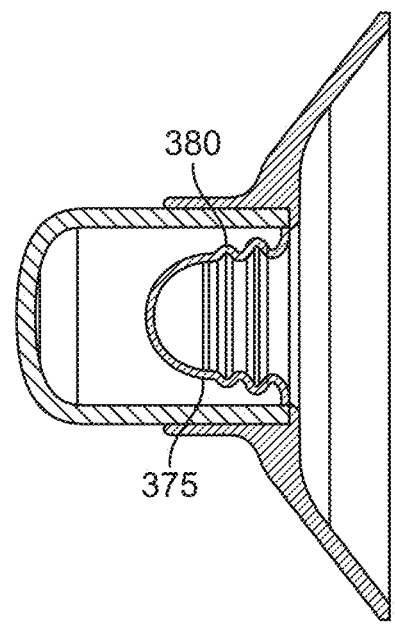
FIG. 7 is a cross-sectional view of another a breast interface, in accordance with embodiments.

FIG. 7 illustrates another embodiment of flexible membrane 375 with corrugated features 380 for increased surface area.

Suitable materials for the flexible membrane are known to those of skill in the art. In many embodiments, the flexible membrane can be made of a material designed to expand and contract when subject to pressures from the coupling fluid such as silicone, polyether block amides such as PEBAX, and polychloroprenes such as neoprene. Alternatively, the flexible membrane can be fabricated from a substantially rigid material, such as stainless steel, nitinol, high durometer polymer, or high durometer elastomer. In these embodiments, the rigid material would be designed with stress and/or strain distribution elements to enable the substantial deformation of the flexible membrane without surpassing the yield point of the material.

Figure 8A:
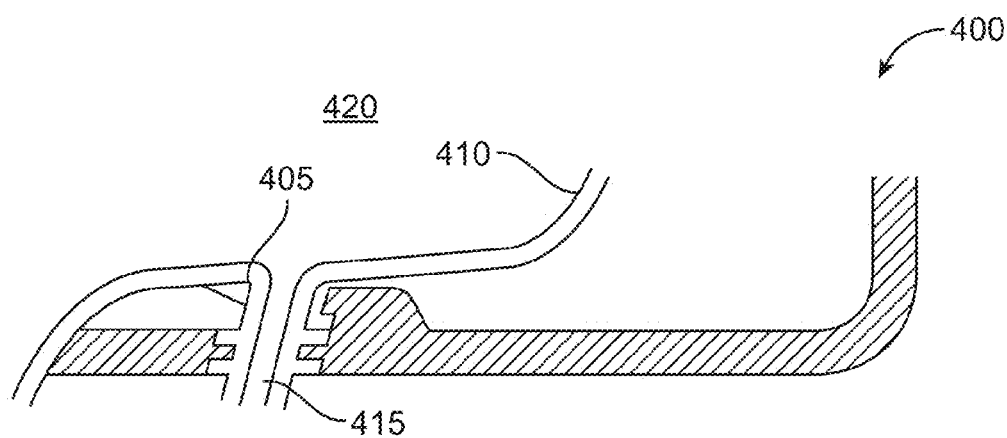
FIG. 8A is a cross-sectional view of an integrated valve within a flexible membrane in an open position, in accordance with embodiments.
Figure 8B:
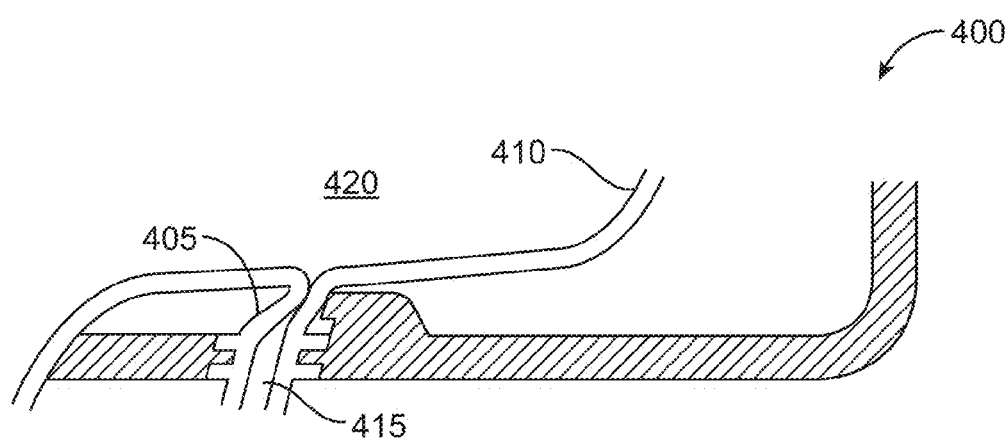
FIG. 8B is a cross-sectional view of an integrated valve within a flexible membrane in a closed position, in accordance with embodiments.

FIGS. 8A and 8B illustrate preferred embodiments of a breast interface 400 in which an exit valve 405 is integrated into the flexible membrane 410 to control the flow of expressed milk through exit port 415. The exit valve 405 is opened to allow fluid flow when the flexible membrane 410 is relaxed, as shown in FIG. 8A, and is closed to prevent fluid flow when the flexible membrane 410 is deformed, as shown in FIG. 8B. The exit valve 405 enables substantial vacuum pressure to be present in expression area 420 during extraction, while allowing milk to drain during the rest phase of the pump stroke. While many conventional breast pump valves function on pressure differentials alone, the exit valve 405 can preferably be configured to also function on the mechanical movement of flexible membrane 410. Incorporation of an integrated exit valve 405 with mechanical functionality as described herein can improve the sealing of the breast interface 400 during vacuum creation. Furthermore, the implementation of an exit valve integrally formed within the flexible membrane 410 such as exit valve 405 reduces the number of parts to be cleaned.

Mechanical Pumping Device

Figure 9:
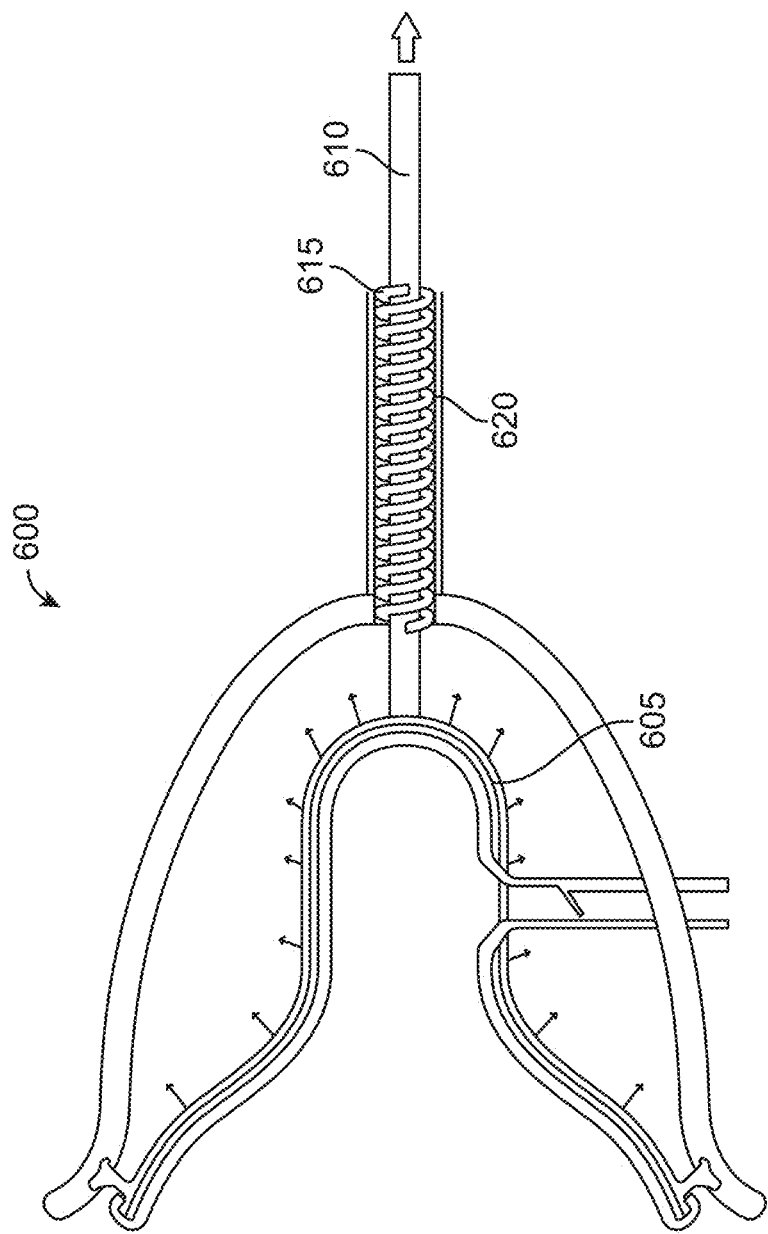
FIG. 9 is a cross-sectional view of a breast interface with a mechanical deformable member, in accordance with embodiments.

FIG. 9 illustrates an alternative embodiment of a breast interface 600 in which a mechanical deformable member 605 can be used in place of a flexible membrane. The mechanical deformable member 605 can be constructed from similar techniques as those used for the flexible membrane as described herein. The mechanical deformable member 605 is coupled to a tensile element 610. In some instances, tensile element 610 is disposed within an axial load absorbing member 615. The axial load absorbing member 615 is disposed within tube 620. Preferably, tensile element 610 is concentrically disposed within axial load absorbing member 615 and axial load absorbing member 615 is concentrically disposed within tube 620. Alternative arrangements of tensile element 610, axial load absorbing member 615, and tube 620 can also be used.

Figure 10:
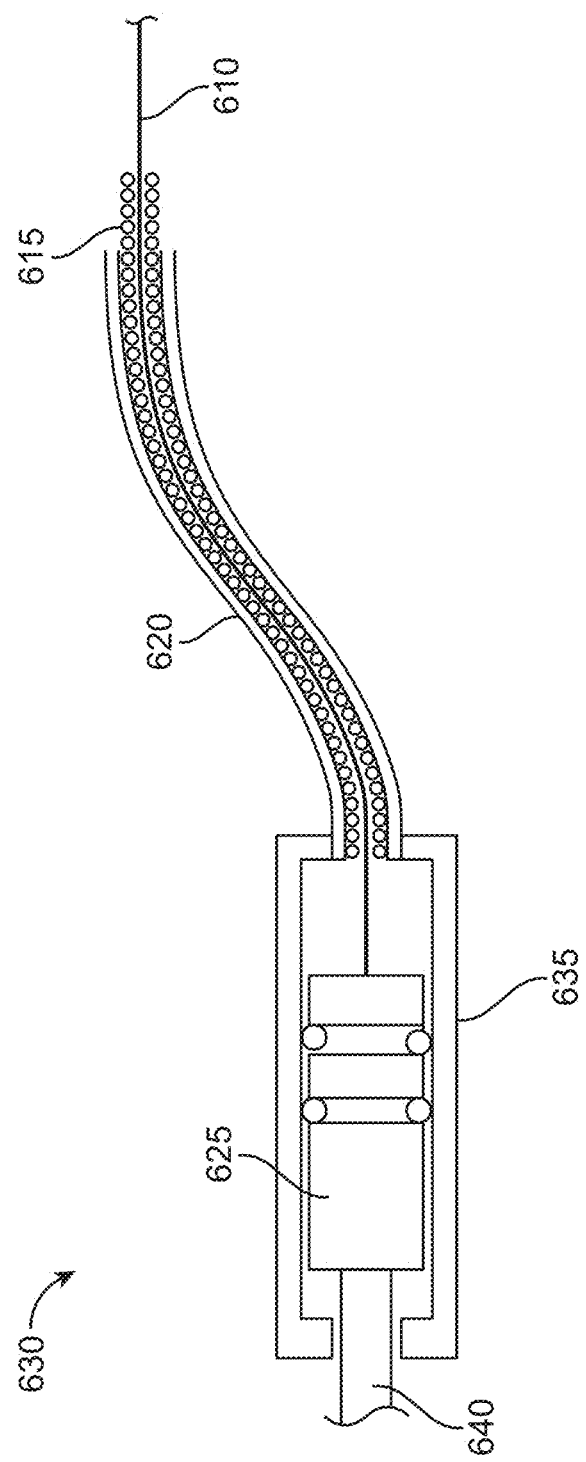
FIG. 10 is a cross-sectional view of a mechanical driver for a mechanical deformable member, in accordance with embodiments.

FIG. 10 illustrates the tensile element 610 coupled to driving element 625 of an actuation assembly 630 within an assembly housing 635. Driving element 625 is operatively coupled to a driving mechanism, such as a driving mechanism housed within a controller, through shaft 640. Axial load absorbing member 615 within tube 620 is fixedly coupled to the assembly housing 635. Displacement of the driving element 625 transmits tensile force through tensile element 610 to the mechanical deforming member 605 to create vacuum pressure against the breast. The driving element 625 can be actuated by a suitable driving mechanism, such as the embodiments previously described herein.

The tensile element 610 can be any suitable device, such as a wire, coil, or rope, and can be made from any suitable material, such as metals, polymers, or elastomers. Axial load absorbing member 615 can be made from any suitable axially stiff materials, such as metals or polymers, and can be configured into any suitable axially stiff geometry, such as a tube or coil.

Fluid Collection and Quantification System

In many instances, it can be desirable to measure and track various characteristics of the collected fluid such as milk expression and collection, such as the amount of milk production (e.g., volume, weight), expression frequency (e.g., time, date), expression duration, and/or the composition of the expressed milk. In existing approaches, the tracking of milk production is commonly accomplished by manual measurements and record-keeping. Exemplary embodiments of the devices described herein may provide digital-based means to automatically measure and track milk production for improved convenience, efficiency, and accuracy.

In order to facilitate milk inventory tracking and management, a unique identifier may be assigned to the milk expressed during a single pumping session and preferably for only a single breast. Alternatively, a single unique identifier may be assigned to milk expressed during multiple pumping sessions within a pre-designated time window, from one or both breasts. The pre-designated time window may comprise any length of time that is appropriate or convenient for a user in managing the user's milk inventory. For example, many users combine milk expressed during multiple pumping sessions within the same calendar day or within 24 hours. Accordingly, the same unique identifier may be assigned to milk expressed during all pumping sessions within the desired time window.

The unique identifier may be disposed on the collection vessel or on the reservoir coupled to the expression device, wherein the reservoir may comprise a bottle and/or a bag. The reservoir may be removably couplable to the expression device, such that a new reservoir with a unique identifier may be used for each pumping session. The collection reservoir, once removed from the expression device, may be used as a storage reservoir for the expressed milk. Alternatively or in combination, the unique identifier may be disposed on a storage reservoir separate from the collection vessel, such as a storage bottle or bag into which a user may transfer the expressed milk collected in the collection vessel.

The unique identifier may comprise a pre-labeled identifier such as a barcode or a Quick Response (QR) code, or it may comprise an identifier that is manually labeled by the user, such as a label removably disposed in a label window, or an area that can be written on with a pen or a marker. A pre-labeled serial number may also be provided on the reservoir. The unique identifier may be digitally coupled to the basic information pertaining to the pumping session such as the date, start time, and end time of the session, collected by either the controller of the pump or a sensor integrated with the expression device. The unique identifier may also be digitally coupled to the one or more attributes of the expressed milk as quantified by the sensors as described herein. The data associated with each unique identifier can be stored in a data array either locally or remotely as described in further detail herein, such that the data may be used to track and manage the inventory of the expressed milk. A single unique identifier may also be digitally coupled to information pertaining to multiple pumping sessions, for example to all pumping sessions within the same calendar day as described herein, or any other defined collection period. The single unique identifier may additionally be digitally coupled to the one or more attributes of the expressed milk from the multiple pumping sessions. The attributes of the expressed milk from each pumping session may be separately recorded and each associated with the single unique identifier. Alternatively, the attributes of the expressed milk from the multiple pumping sessions may be combined. For example, the volume of expressed milk from each of the multiple pumping sessions may be added together to generate a total volume that is associated with the single unique identifier, and/or the composition of the expressed milk (e.g., fat content, calories, etc.) from the multiple pumping sessions may be averaged to generate the average composition of expressed milk that is associated with the single unique identifier.

Alternatively to or in combination with the various types of unique identifiers discussed above, the unique identifier may comprise a radio-frequency identification (RFID) tag or near field communication (NFC) tag. Preferably, the RFID tag comprises a passive tag that may produce an authentication response to radio energy transmitted by an RFID scanner or reader. Alternatively, the RFID tag may comprise an active tag or a battery-assisted passive tag configured to periodically transmit its ID signal. The RFID tag may be read-only, wherein the tag comprises a pre-assigned ID, or the tag may be read/write-enabled, wherein the tag may be programmed by a user. The RFID tag may be read or scanned by an RFID reader by placing the RFID tag near or in contact with the RFID reader. The scanning of an RFID tag by an RFID reader can lead to the addition or removal of the tagged milk to or from a user's inventory, as described in further detail elsewhere herein.

In exemplary embodiments, the pumping devices described herein can include one or more sensors for generating measurement data indicative of one or more characteristics of milk expression, such as the volume of expressed milk. In preferred embodiments, the volume can be measured as volume per unit time, volume per pump stroke (e.g., stroke of the actuation assembly), or volume per pump power cycle (e.g., power cycle of the actuation assembly). Any description herein pertaining to measurement of volume can also be applied to measurements of other characteristics, and vice-versa. Any suitable type of sensor can be used, such as accelerometers, Hall effect sensors, photodiode/LED sensors, CCD sensors, cameras and other imaging devices, capacitive sensors, strain gauges, etc., and such sensors can be used in any number and combination. The sensors can be positioned at any location suitable for monitoring fluid flow from the breast, such as on or near a breast interface (e.g., the expression area 260, drain port 265, collection vessel 275). In embodiments where milk is concurrently expressed from a pair of breasts via a pair of breast interfaces, sensors can be located on or near both breast interfaces, or on or near only one of the breast interfaces. The sensors may be integrally formed with or permanently affixed to the pumping device, or they may be provided separately and coupled to the pumping device prior to use. Alternatively, the sensors may be provided as a separate unit that can measure the one or more characteristics of the expressed milk after the milk has been expressed.

Sensors for quantifying the composition of the expressed milk may also be provided with the pumping devices described herein. For example, sensors may be provided for measuring the relative amounts of certain carbohydrates, fats, proteins, vitamins, and minerals known to be present in breast milk. Sensors may also be configured to determine the estimated caloric value of the expressed milk and/or the percentage of alcohol present in the milk. Such sensors may include devices that can spectroscopically measure the presence of certain compounds in a volume of breast milk, or a multi-spectral imaging system that can image the collected fluid under different wavelengths to estimate composition and density, or devices that can measure the enzymatic activity produced by certain compounds of breast milk that act as substrates for specific enzymes. The sensors may comprise stand-alone units with their own user interface, or they may be removably couplable with a peripheral device such a mobile phone, tablet, or personal computer, wherein the peripheral device can be provided with an application programmed to control the sensor unit. The data may also be stored in the cloud so that it may be accessed and used by other computing devices and other users such as a physician or a child caretaker. Other characteristics which may be sensed include but are not limited to milk density, weight, percent fat content, as well as other attributes.

Figure 11A:
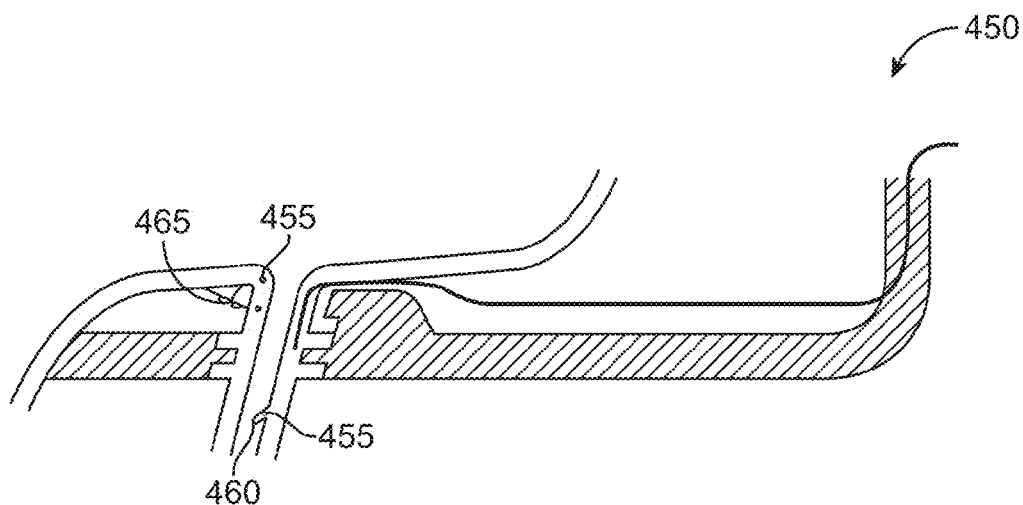
FIGS. 11A-11L illustrate exemplary embodiments of sensors for detecting fluid.
Figure 11B:
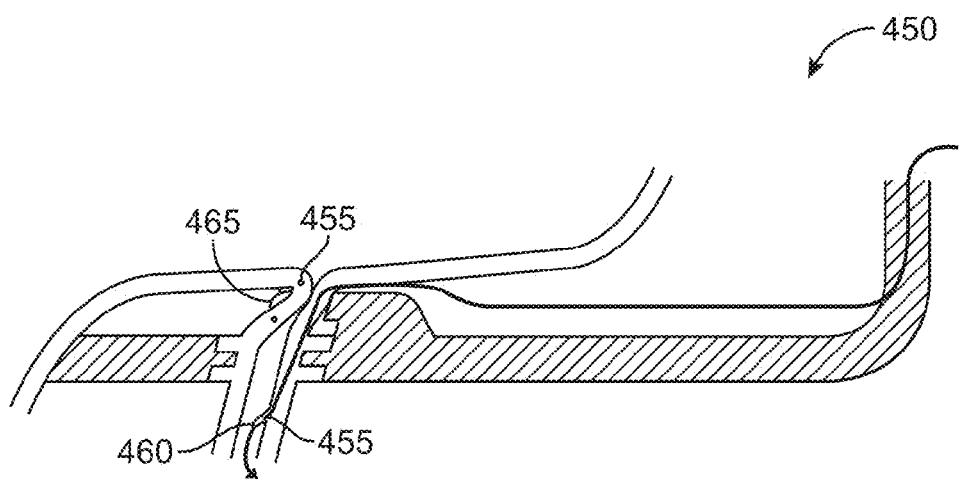

FIGS. 11A and 11B illustrate exemplary embodiments of a breast interface 450 with valve-integrated sensors 455. Sensors 455 are preferably located in a valve, such as the flap valve 460, but may also be located in exit valve 465, or any other valve (e.g., on or near the collection vessel) that is opened by fluid flow. In exemplary embodiments, the sensor 455 includes an accelerometer measuring the position and/or motion of the valve, such as a length of time that the valve is opened, and the resultant measurement data can be interrogated to quantify the fluid flow. Preferably, the breast interface 450 is used in conjunction with a second, identical breast interface to concurrently express milk from a pair of breasts (e.g., simultaneously, alternatingly, or sequentially). A pair of accelerometers can be used to detect the position and/or motion of the corresponding valve in each interface. In some instances, movements of the user may cause the accelerometers to produce motion signals that are erroneously interpreted as valve motion. Accordingly, in preferred embodiments, suitable approaches are used to distinguish between signals resulting from motion of the user and signals generated by motion of the valves. For example, the pumping device can be configured to alternatingly express milk from each breast, such that the corresponding valves are also opened alternatingly. Consequently, motion detected simultaneously from both accelerometers can be regarded as resulting from user motion, rather than from valve motion. The user motion can be subtracted from the total motion signal obtained by the accelerometers in order to obtain the valve motion, and thereby determine the position of each valve.

Figure 11C:
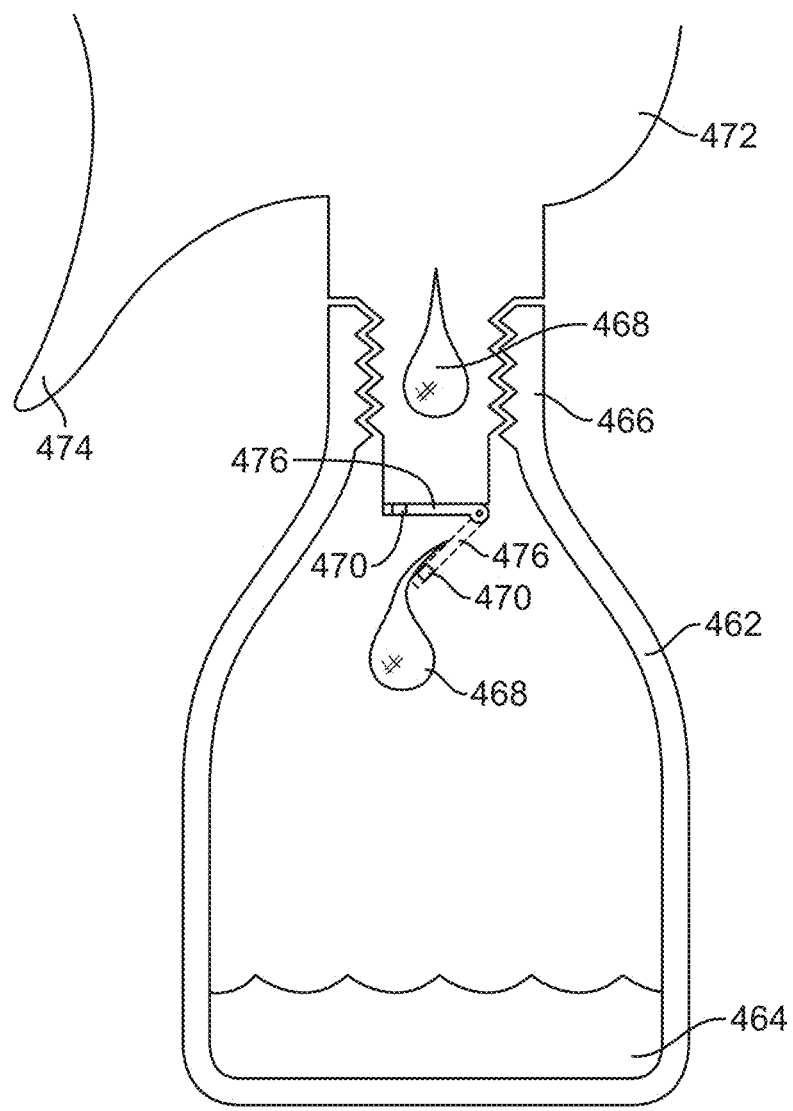

FIG. 11C illustrates an embodiment with an accelerometer 470 more clearly. The accelerometer 470 is coupled to a flap valve 476 on the output of the expression device 472 which has a breast interface 474 (sometimes also referred to as a distal assembly in this specification). The expression device and breast interface may be any of the embodiments disclosed herein. As breast milk 468 is expressed, it collects at the output of the device. When enough fluid is collected, flap valve 470 opens, and the milk 468 drains into reservoir 462 and collects in a layer 464 therein. The reservoir 462 is preferably threadably connected to the expression device 472 so that it may easily be attached and detached. Movement of the flap valve 476 is tracked using accelerometer 470. Data from the accelerometer is then processed, transmitted or displayed using any of the methods or means disclosed herein.

In other exemplary embodiments, the pumping devices described herein can utilize one or more beam-break sensors (e.g., infrared-based, laser-based, etc.) situated at a suitable location in the pumping device (e.g., in or near a valve, an exit port, or other component permitting fluid passage). The beam-break sensor can include a plurality of sensor components and can be configured to detect passage of fluid between or near one or more of the components. Preferably, the sensor can be configured to generate a signal when the expressed fluid breaks a beam by passing between a beam emitter and a beam detector. The resultant signal can be used to produce measurement data indicative of the volume of expressed fluid. For example, the measurement data can be based on the length of time the fluid passes between or near the sensor components.

Figure 11D:
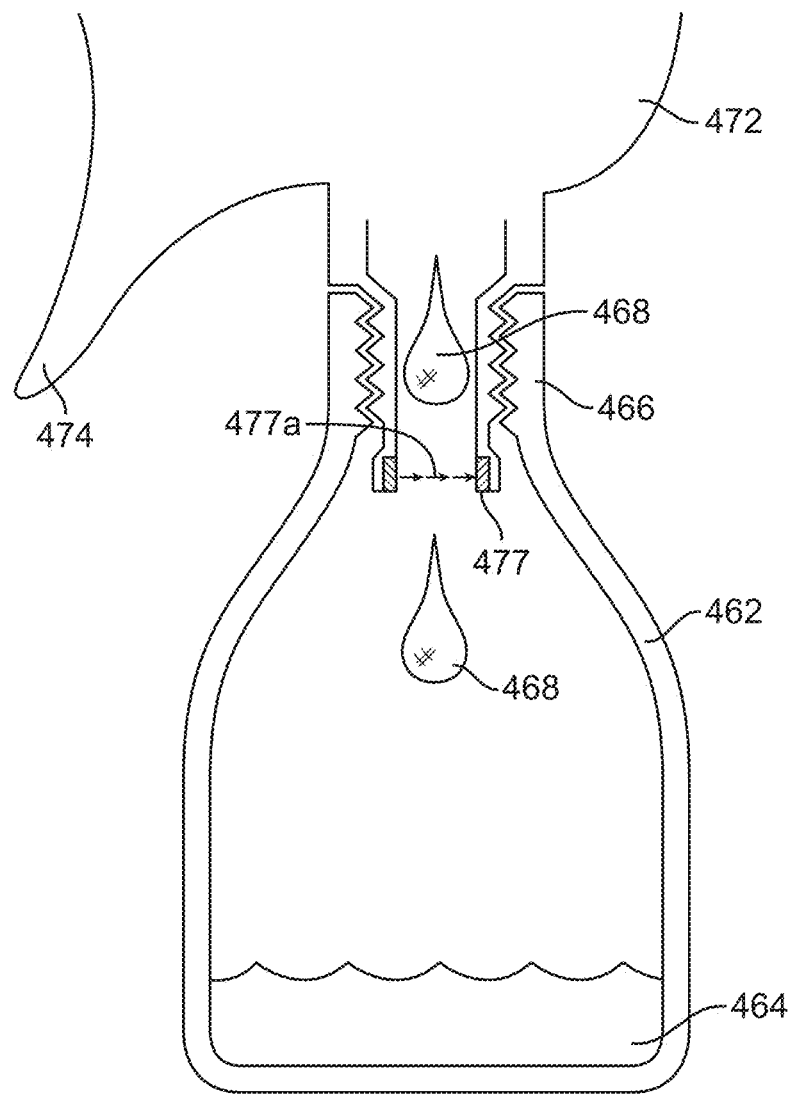

FIG. 11D illustrates an exemplary embodiment of a milk expression device that employs a beam break sensor 477. The expression device 472 includes a breast interface 474 and a reservoir 462. The reservoir is threadably or otherwise coupled 466 to the expression device. Any of the exemplary embodiments of expression devices, interfaces, reservoirs, etc. disclosed in this specification may be used in this exemplary system. A beam-break sensor 477 is disposed adjacent the output of the expression device, and thus as droplets 468 of milk drain from the expression device outlet into reservoir 462, they break the light beam 477a, allowing measurement of the fluid expressed. The fluid collects in a layer 464 in reservoir 462. The data from the sensor can then be processed, transmitted, or otherwise displayed using any of the methods disclosed herein.

In another exemplary embodiment, the pumping devices described herein can include one or more image sensors for capturing images of the fluid in order to quantify the expression volume, such as a charge-coupled device (CCD) or a camera. The image sensors may be integrated with or coupled to a suitable portion of the pumping device. Conversely, the image sensors can be located on another device separate from the pumping device, such as a smartphone or other mobile device. In exemplary embodiments, the breast interface includes a valve permitting the passage of expressed fluid, as previously described herein, and a suitable image sensor is positioned on or near the valve in order to capture images of fluid passing through the valve. Preferably, the image sensor is operably coupled to a processing unit configured to analyze the image data (e.g., using a suitable image analysis algorithm) in order to determine the fluid volume. For example, the image sensors can be used to capture images of drops of fluid, and the images can be analyzed to count the number of drops. In some instances, the image data can be transmitted to a computing device (e.g., a smartphone) for analysis, as described in further detail below.

Figure 11E:
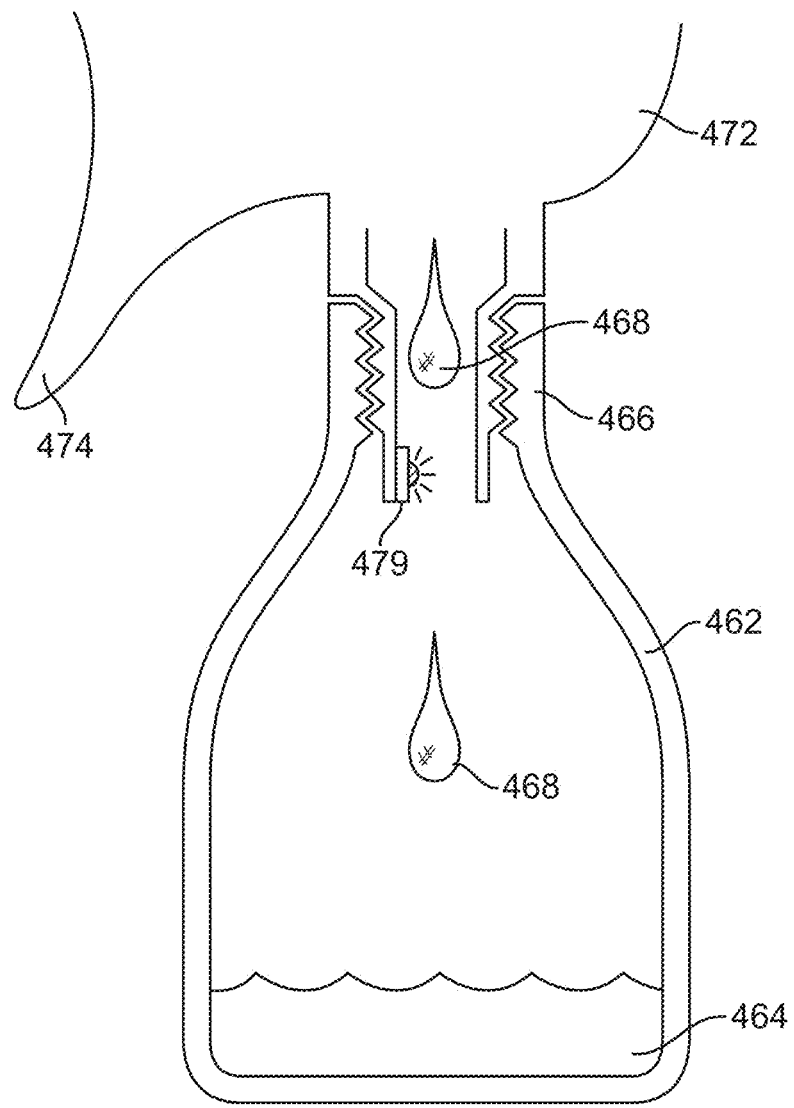

FIG. 11E illustrates an exemplary embodiment having a CCD device 479 adjacent an outlet of the expression device. The expression device 472 includes interface 474 and reservoir 462, either of which may be any of the embodiments disclosed herein. As milk 468 is expressed, it passes through the outlet of the expression device past CCD 479 which detects the fluid and allows quantification thereof as previously described. The milk 468 then accumulates in a layer 464 in reservoir 462. Data from the CCD may then be processed, transmitted, or otherwise displayed using any of the methods disclosed herein.

Figure 11F:
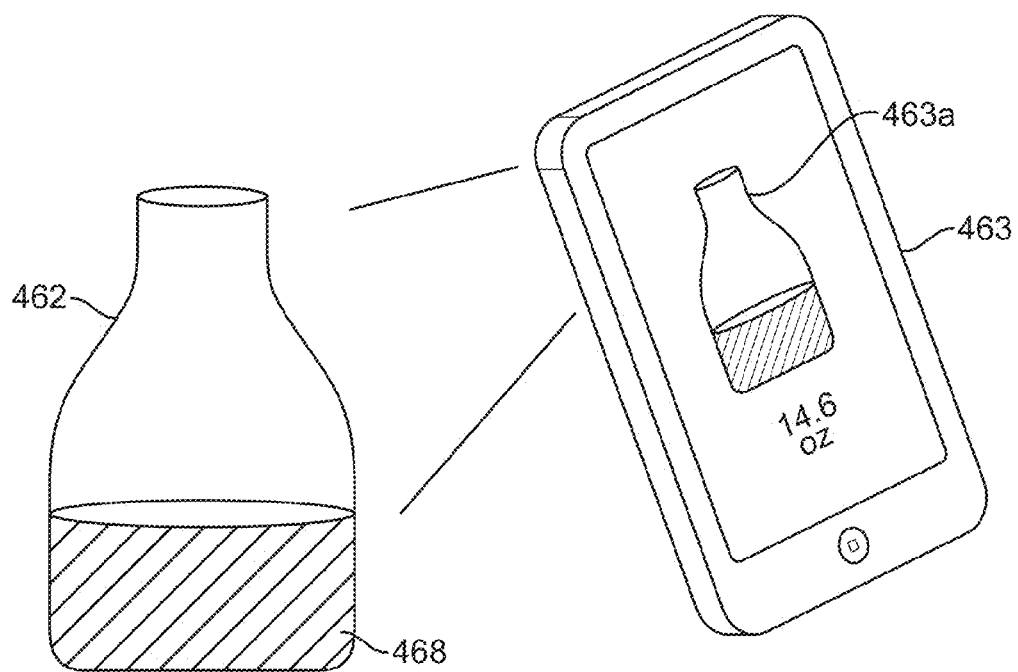

FIG. 11F illustrates an exemplary embodiment that uses an image of the reservoir to characterized the expressed milk. Once milk 468 has been collected in reservoir 462, the reservoir may optionally be detached from the expression device. A mobile phone or other device may then be used to take a photo 463a of the reservoir which has a suitable application for analyzing the photo and determining how much milk has been expressed, as well as optionally providing other details about the expressed milk. The data is processed, transmitted, or otherwise displayed using any of the methods disclosed herein.

Figure 11G:
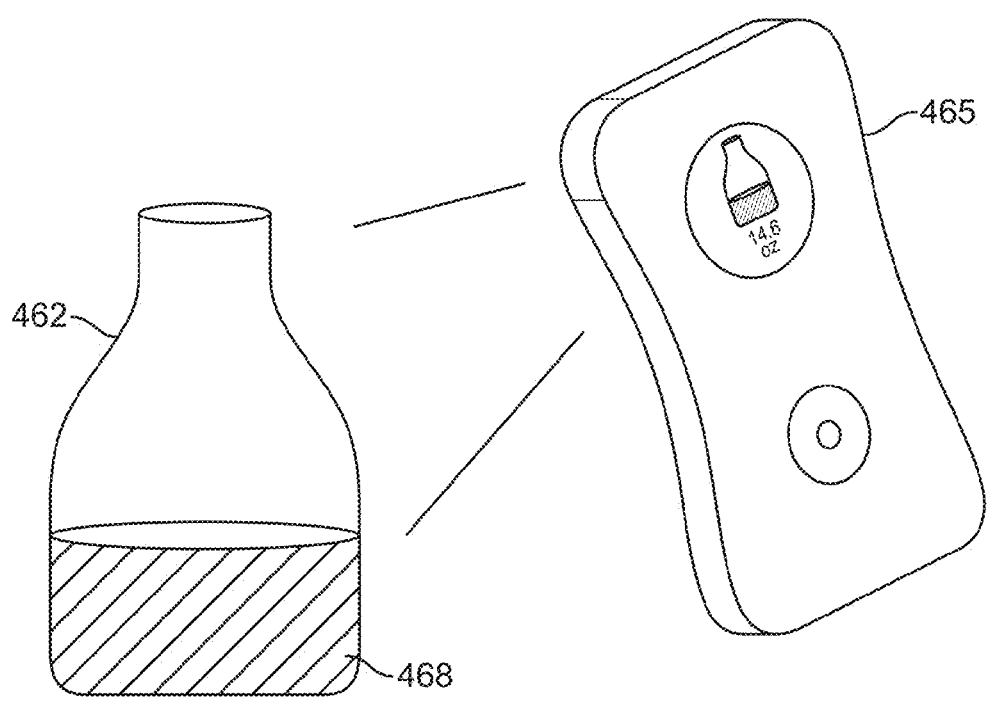

FIG. 11G illustrates an alternative embodiment of a photo sensor system. After milk 468 has been expressed and collected in a reservoir 462, a camera in the pump control unit 465 may be used to obtain an image of the milk in the reservoir and analyze it for quantity or other characteristics. The pump control 465 may be any of the pump controls described elsewhere in this applications, and the data may be processed, transmitted, or displayed using any of the methods disclosed herein.

In some exemplary embodiments, the pumping devices described herein can employ one or more capacitive sensors for measuring fluid volume. The capacitive sensors can be configured to detect the volume of fluid contained in any suitable portion of the pumping device, such as fluid contained within a collection reservoir and/or within a breast interface (e.g., expression area 260, a component permitting passage of fluid from the interface such as a valve, exit port, or tube).

Figure 11H:
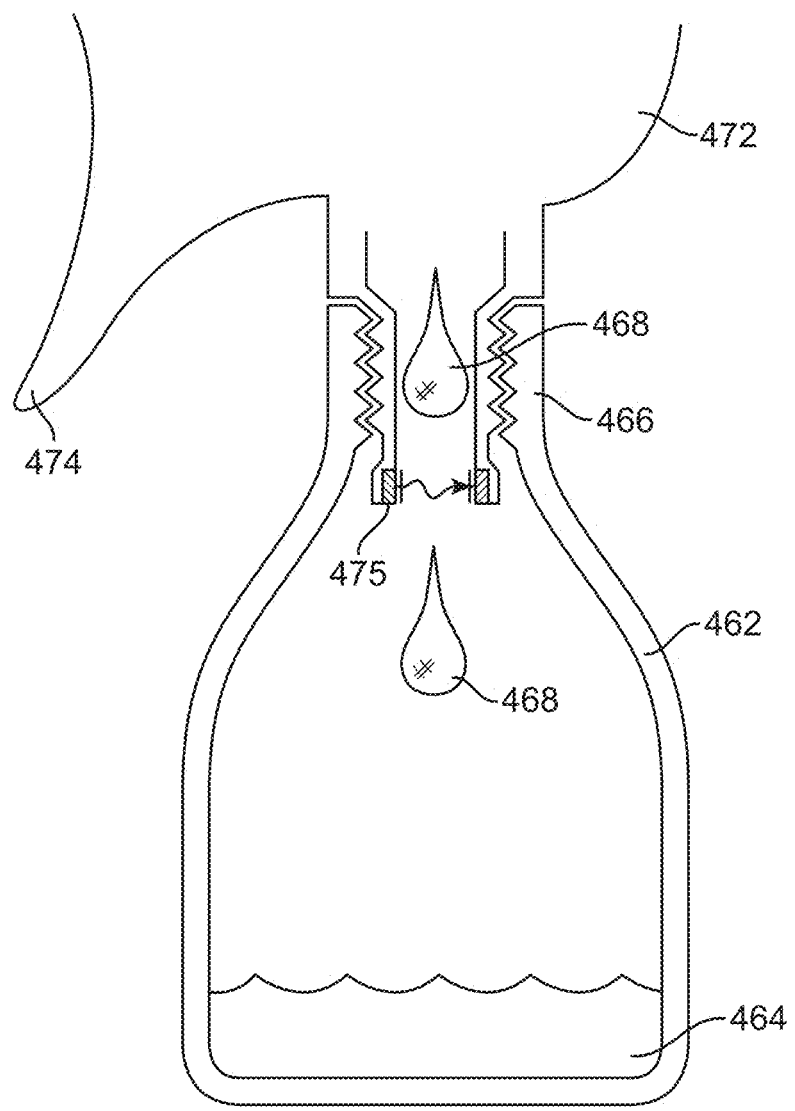
Figure 11I:
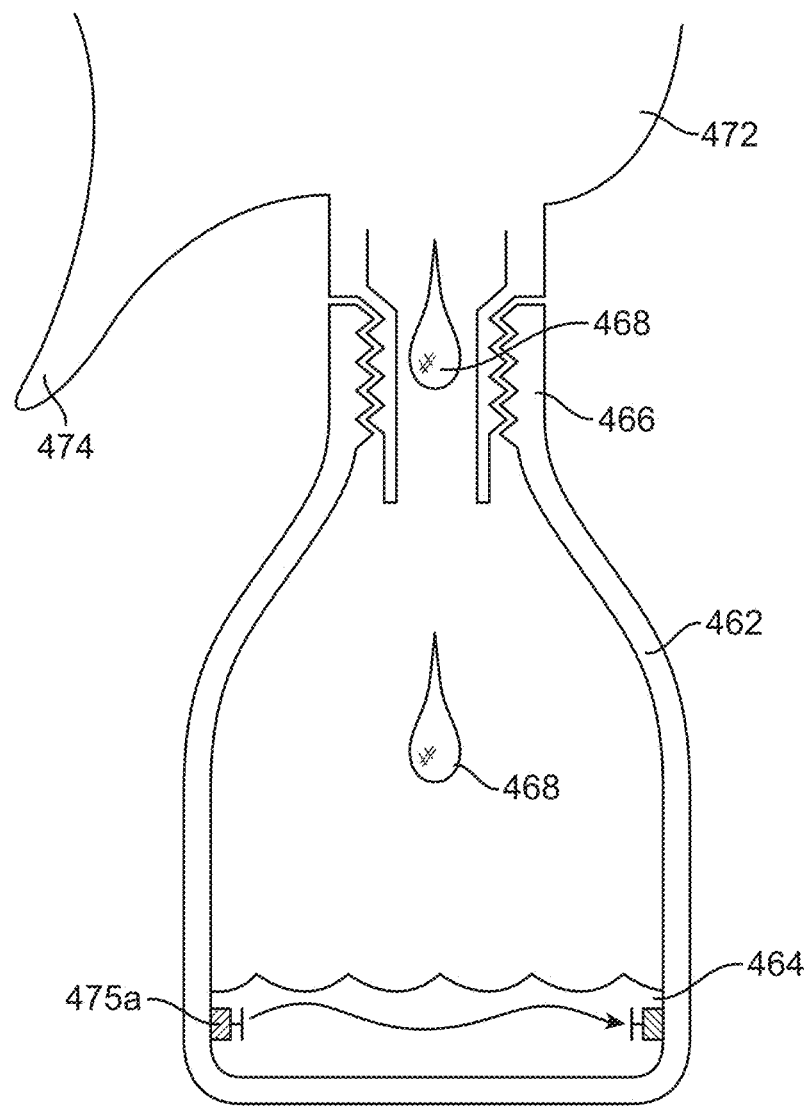

FIGS. 11H-11I illustrate exemplary embodiments of expression devices that use capacitive sensors. The expression device 472 may be any of the expression devices disclosed herein and they have an interface 474 that also may be any of the interfaces disclosed in this specification. A reservoir 462 is threadably 466 or otherwise coupled to the expression device and the reservoir may be any of the reservoirs described herein. As milk 468 is expressed and collected at the outlet of the expression device, it passes through the capacitive sensor 475 which is then able to measure fluid volume. FIG. 11I is similar to the embodiment in FIG. 11H, with the major difference being that the capacitive sensor 475a is disposed in the reservoir 462 near the bottom, rather than in the outlet of the expression device. The data from the sensor in either embodiment may then be processed, transmitted, or displaying using any of the techniques described herein.

In other exemplary embodiments, one or more strain gauges can be used to measure the volume of expressed fluid. The strain gauges can be situated at any suitable position in the pumping device. For example, a strain gauge can be coupled to a flap valve (or any other valve permitting passage of expressed fluid) and configured to determine the volume based on the displacement of the valve over time. Alternatively or in addition, a strain gauge can be coupled to a collection reservoir and configured to measure the volume of expressed fluid contained within the reservoir.

Figure 11J:
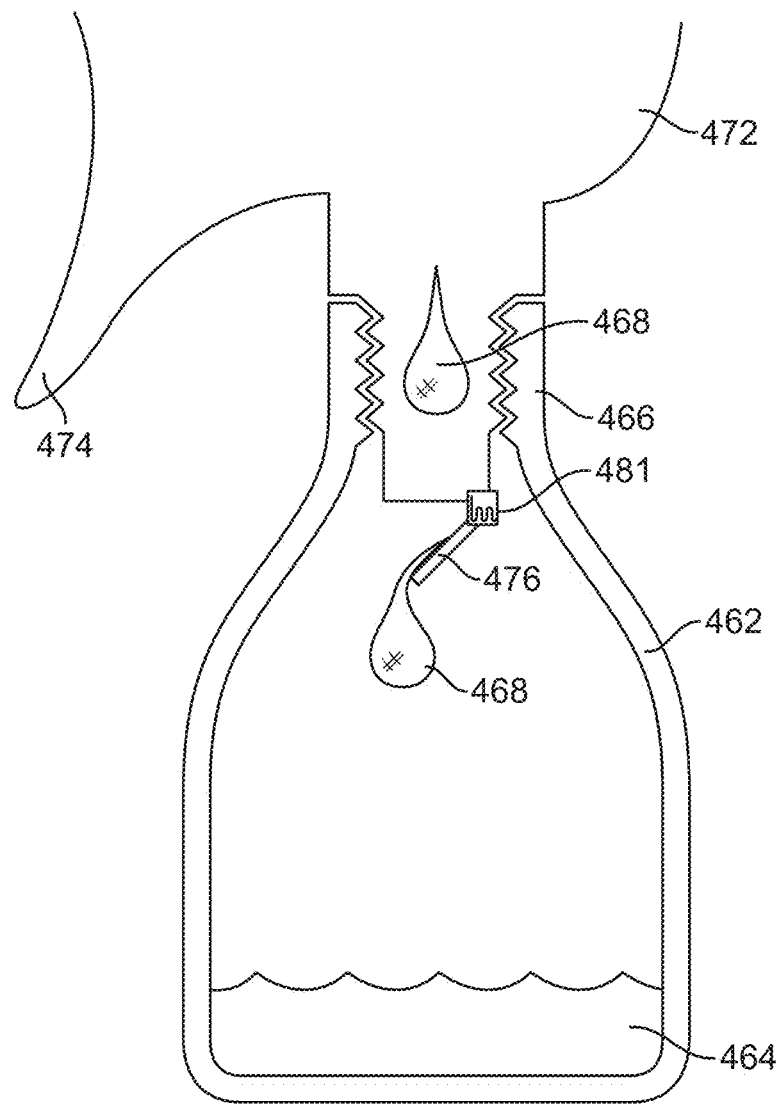

FIG. 11J illustrates an exemplary embodiment of a strain gauge. The expression device 472 includes an interface 474 and reservoir 462 threadably 466 or otherwise coupled thereto. Any portion of this system may be any of the components described elsewhere in this specification. As milk is expressed 468 it accumulates in the outlet of the expression device. Eventually, the weight of the accumulated milk is sufficient to actuate and open flap valve 476. A strain gauge 481 is coupled to the flap valve and this sensor is then used to collect data on movement of the valve and therefore this correlates to the collected fluid. The fluid accumulates in a layer 464 in reservoir 462. The data from the sensor is then processed, transmitted, or displayed using any of the methods disclosed herein.

Figure 11K:
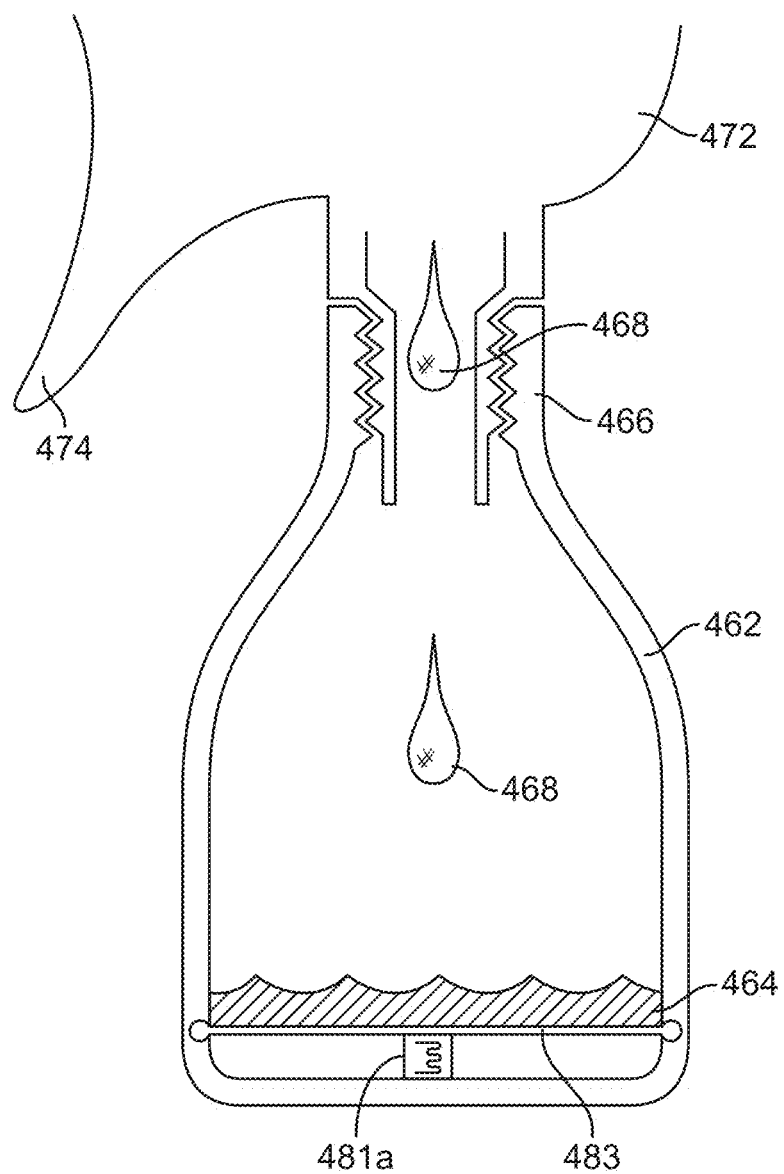

FIG. 11K illustrates an alternative embodiment of a strain gauge sensor. This embodiment generally takes the same form as the previous embodiment with the major difference being that the collected fluid layer 464 is disposed over a plate 483 which bears the weight of the collected fluid. Thus, as the weight increases or decreases, a strain gauge 481a disposed under the plate 483 detects the weight change and this can be correlated to the collected fluid volume. Data from the sensor is then processed, transmitted, or displayed according to any of the methods disclosed herein.

Figure 11L:
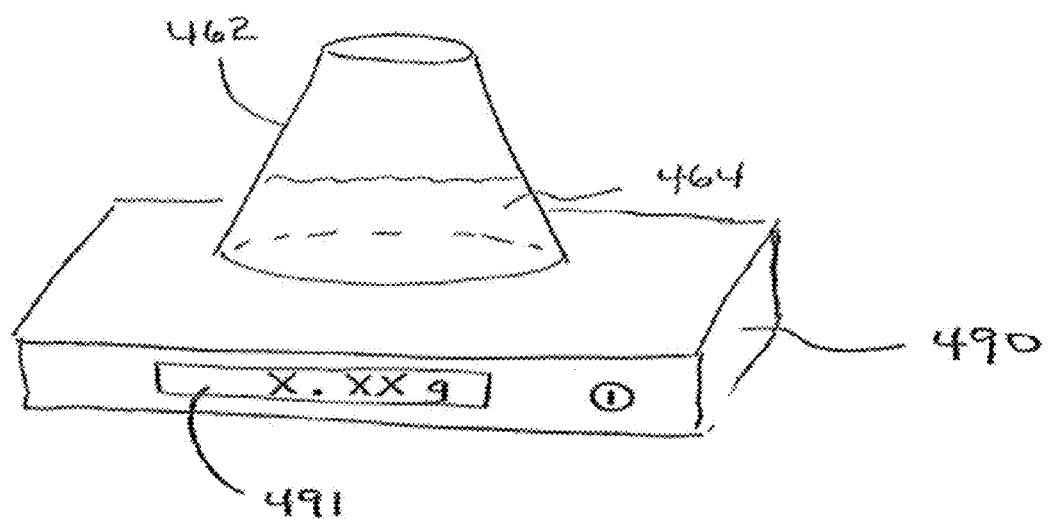

FIG. 11L illustrates an exemplary embodiment that uses a scale to quantify the weight of the expressed milk. The reservoir 462 containing the expressed milk 464 may be uncoupled from the expression device and placed on a scale 490. The scale can measure the weight of the reservoir containing the milk, and can be configured to subtract the weight of an empty reservoir in order to calculate the weight of the expressed milk. The scale may have a stored calibration curve that can be used to convert the measured weight to a corresponding fluid volume. Alternatively, the scale may allow the user to enter in the fluid volume of the expressed milk, and calculate the corresponding density of the expressed milk. The scale may comprise a display screen 491, which may display one or more of the weight, fluid volume, or density of the milk. The scale may be configured to communicate with a peripheral device such as a controller 500 of the breast milk expression device or a computing device as described in further detail herein.

In some embodiments, the composition of the milk expressed by the pumping device may be quantified by a sensor unit provided with the pumping device. The composition of breast milk can be valuable information for understanding whether an infant is obtaining the appropriate amount of nutrition via the milk. This information can help mothers or clinicians identify whether additional nutrition should be supplied to the infant. Components of breast milk considered to be nutritionally important include carbohydrates such as glucose and lactose, fats such as triglycerides, proteins such as lactoferrin, organic acids such as taurine, vitamins such as vitamin D, and minerals such as zinc, copper, and iron.

Figure 23A:
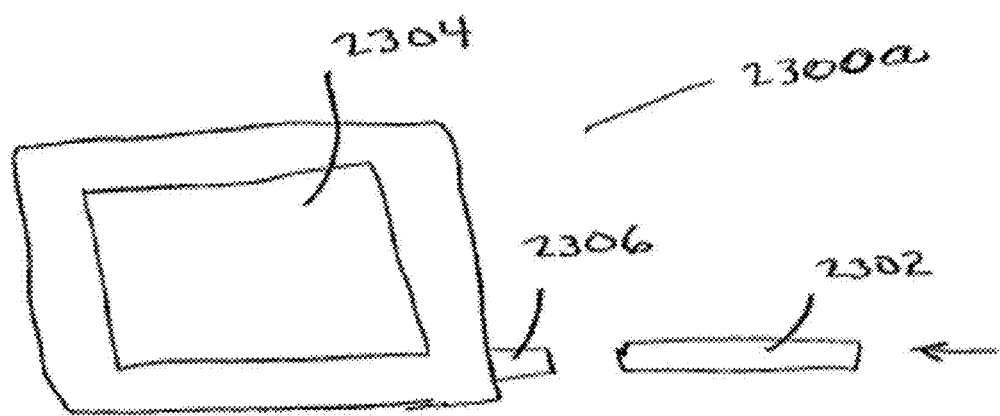
FIGS. 23A and 23B illustrate exemplary embodiments of a sensor unit for quantifying the composition of expressed milk using an enzyme assay.
Figure 23B:
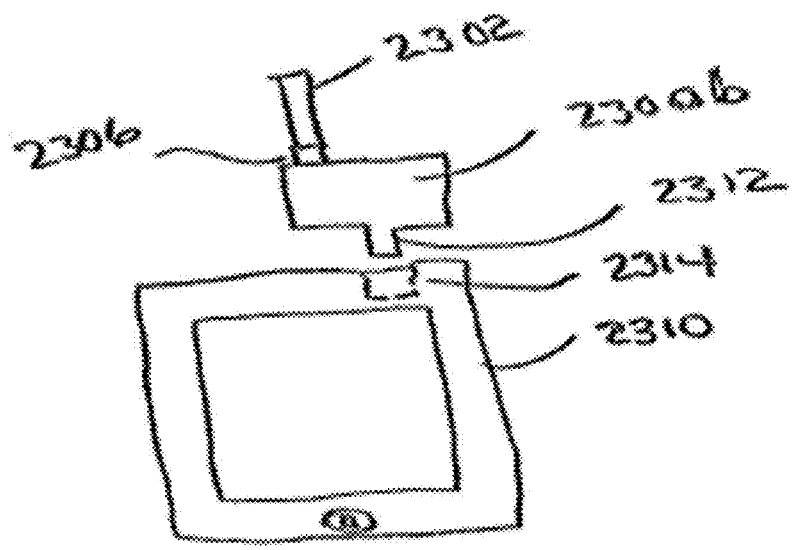

FIGS. 23A and 23B illustrate exemplary embodiments of a sensor unit for quantifying the composition of expressed milk using an enzyme assay. A test strip 2302 contains one or more enzymes that can react with target components of the breast milk. For example, the test strip may contain glucose oxidase to help detect glucose and/or beta-galactosidase to help detect lactose. The test strip may have a unique identifier that matches the unique identifier of the reservoir. One or more drops of the breast milk, expressed using the breast milk expression device as described herein, can be placed on the test strip, and the test strip can subsequently be inserted into the sensor unit. The user interface of the sensor unit may prompt the user to enter or scan the unique identifier of the reservoir or of the test strip, so that the data from the analysis may be digitally coupled to the expressed milk from a particular pumping session. Once the unique identifier is entered or scanned into the system, the user may select an option to run the test strip analysis from the user interface. The sensor unit comprises electrodes that can detect an electrical current produced by the enzymatic activity that results as the components of the breast milk are hydrolyzed by the enzymes contained in the test strip. The electrical current detected by the sensor unit can be converted into a numerical value denoting the relative amount of one or more components of the breast milk, using a calibration curve stored on the sensing unit. The composition of the milk may be presented as one or more of a concentration or percentage of the one or more components being tested by the enzymes on the test strip. The composition data can be digitally coupled to the unique identifier of the expressed milk, and then stored on a local drive of the sensor unit or of a peripheral device coupled to the sensor unit, via wired communication such as via a USB cable. Alternatively or in combination, the composition data digitally coupled to the unique identifier may be stored on a remote, or cloud, server, wherein the data may be transmitted to the server via wireless communication such as Bluetooth or WiFi.

FIG. 23A illustrates a stand-alone sensor unit 2300*a* having its own user interface. The user interface may be presented to the user through a display screen with an alphanumeric keyboard input, or through a touch screen display 2304. The test strip 2302, having one or more drops of breast milk placed thereon, may be inserted into a port 2306 of the sensor unit 2300*a*. After entering or scanning in the unique identifier of the reservoir or of the test strip, the user may run the analysis, and the results of the analysis may be displayed on the display of the sensor unit.

FIG. 23B illustrates a sensor unit 2300*b* that is configured to be removably coupled to and controlled by a peripheral device 2310 such as a smart phone, tablet or other mobile device. The sensor unit 2300*b* comprises a connector 2312 that inserts into a port 2314 of the peripheral device, such as a headphone port. The peripheral device may comprise a controller of the pumping device or a computing device such as a mobile phone, tablet, or personal computer. The peripheral device comprises an application programmed to provide the user interface of the sensor unit. The user may insert the test strip 2302 having the drops of breast milk placed thereon into a port 2306 of the sensor unit 2300*b*. After entering or scanning in the unique identifier of the reservoir or of the test strip, the user may run the analysis of the test strip through the user interface presented by the peripheral device.

Figure 24:
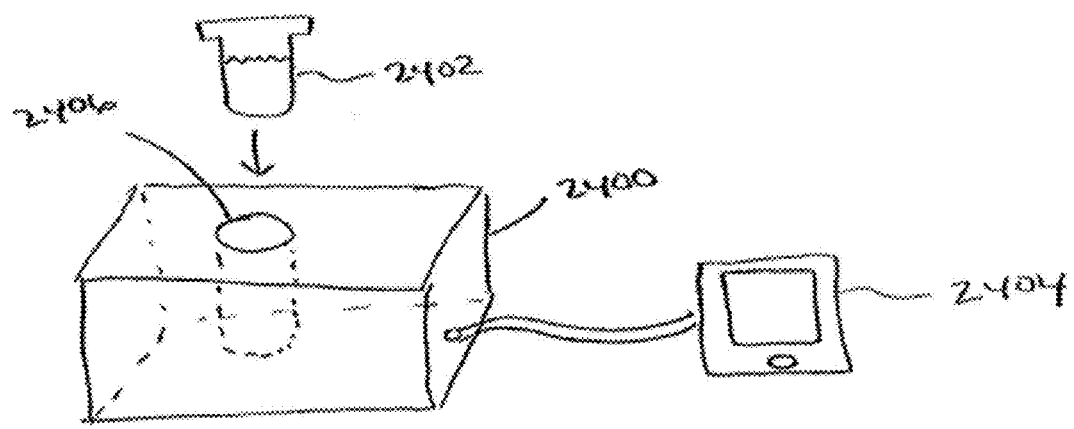
FIG. 24 illustrates an exemplary embodiment of a sensor unit configured to quantify the composition of expressed milk using spectroscopy.

FIG. 24 illustrates an exemplary embodiment of a sensor unit configured to quantify the composition of expressed milk using spectroscopy. The sensor unit 2400 comprises an emitter such as a light-emitting diode, a sample holder 2406, and a detector such a thermal detector or photonic detector. For example, the sensor unit may comprise a mid-infrared transmission spectrometer. The emitter emits light or energy through the sample, and the detector measures the light or energy emissions from the sample and converts the readout to concentrations and/or percentages of the compounds of interest. After a pumping session, the user may transfer a small volume of the expressed milk from the reservoir to a sample container 2402, such as a tube or a cuvette, wherein the sample container may comprise a unique identifier that matches the unique identifier of the reservoir. The sample container with the milk can then be inserted into the sample holder of the sensor unit, and analyzed for the presence of certain compounds in the breast milk. The sensor unit 2400 may be a stand-alone unit with its own user interface, or it may be removably couplable to a peripheral device 2404 such as a mobile phone, table, or other device, having an application programmed to provide the user interface. As described herein, the sensor may digitally couple the obtained composition data to the unique identifier, and store the coupled data either locally or remotely.

Other exemplary embodiments of the breast milk composition sensor may include devices that can detect the presence of various components of breast milk via thin-layer chromatography, colorimetry, electronic counting, chemiluminescence, nephelometry, biuret reagent assays, and multispectral imaging. Specific algorithms may be generated in order to increase the accuracy of the readouts. These and other devices for the quantification of breast milk composition may be integrated with the expression device as described herein or may be provided as separate units that can be stand-alone devices or devices configured to be connected to a peripheral device for operation.

In exemplary embodiments, some or all of the measurement data collected by the sensors can be fed back to the pumping device in order to optimize fluid expression. Preferably, the feedback can be transmitted to a processing unit and/or control unit of the pumping device (e.g., suitable hardware located in the controller 115) configured to control one or more functionalities of the actuation assembly. Based on the feedback, the processing unit can determine changes to actuation parameters of the actuation assembly in order to achieve and/or maintain optimal fluid expression. For example, the feedback can be used to determine adjustments to a vacuum stroke or stroke speed of a pump, piston assembly, or any other suitable actuation assembly.

Figure 21:
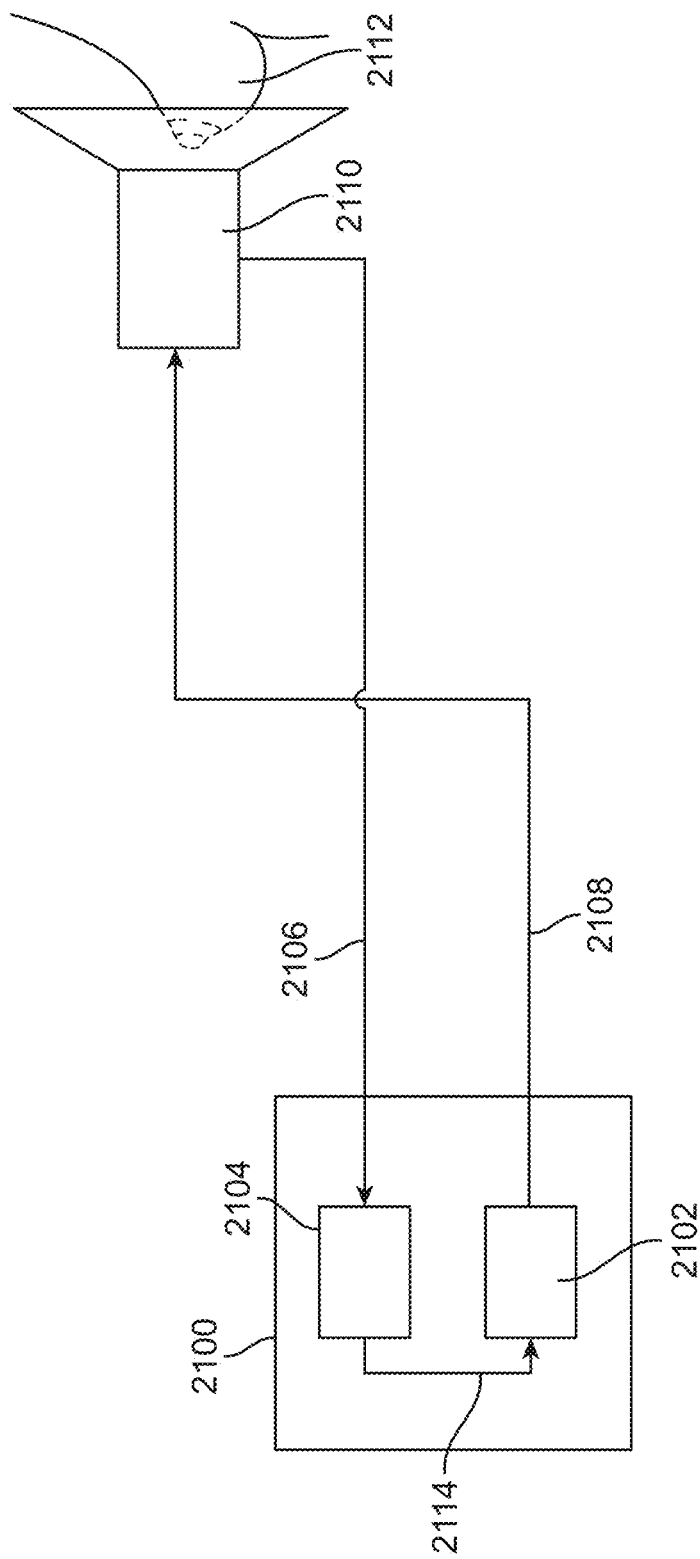
FIG. 21 illustrates the use of a feedback control loop to control a milk expression device.

FIG. 21 illustrates an exemplary expression system with feedback control. The system includes a pump unit 2100 preferably including a controller and processor 2104 as well as a motor 2102 for actuating the device, and a distal assembly 2110 which is sized and shaped to mate with the target anatomy, here a breast 2112. Any of the elements in this exemplary system may be any of the components disclosed elsewhere in other exemplary embodiments. In this embodiment, feedback 2106 from the sensor which monitors expressed milk in the expression device 2110 is transmitted from the distal assembly (expression device with interface) to the controller and processor 2104. The data is processed and this information is used to provide instructions to motor 2102 which increases or decreases actuation of the expression device which is then transmitted by communication 2108 back to the expression device or distal assembly 2110. Any of the embodiments in this specification may include such a feedback loop.

Figure 12:
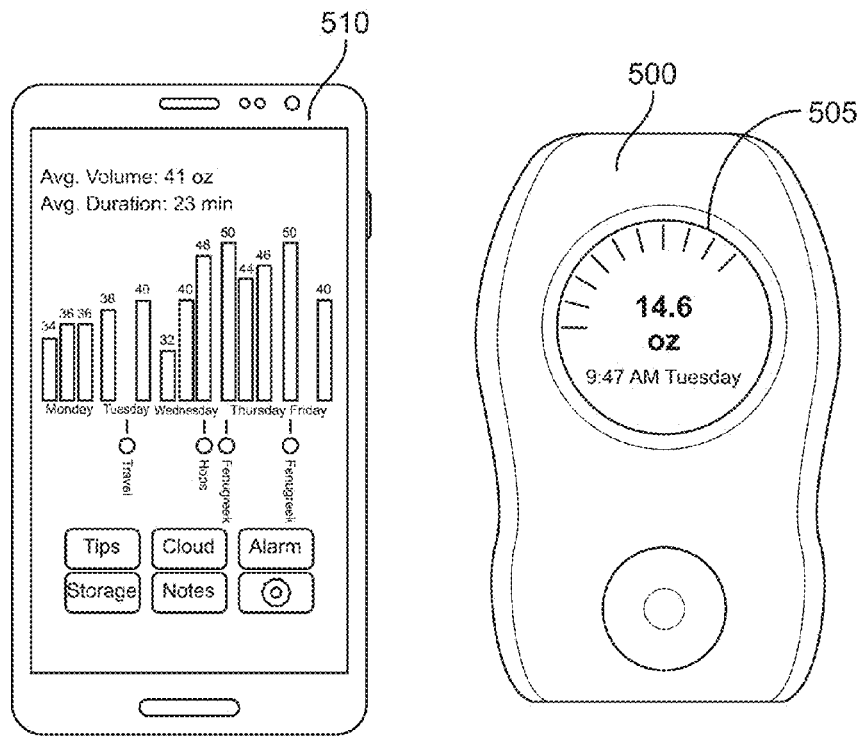
FIG. 12 illustrates a controller and a mobile device, in accordance with embodiments.

FIG. 12 illustrates an exemplary embodiment of a controller 500 for a pumping device including a display screen 505. The controller 500 can include suitable hardware for collecting, processing, and storing the milk expression data described herein, as well as analysis results obtained from processing the expression data. In preferred embodiments, this information is displayed to a user of the pumping device via the display screen 505. Furthermore, information can also be transmitted from the controller 500 and displayed on a separate computing device, such as a mobile device 510, as described in further detail below. The information can be presented in any suitable format, including graphs, charts, tables, images, or other visual elements, and may be static or dynamic (e.g., updated in real time, etc.). The controller 500 can also send information about the times of pump usage to the mobile phone 510 so that the mobile application can identify when pumping has occurred and set reminders at desired pumping times. Such reminders can help avoid missed pumping sessions, and thus reduce the incidence of associated complications such as mastitis. Additionally, the controller 500 can include input devices enabling users to interact with the displayed information, such as the button 515, as well as keyboards, joysticks, touchscreens, switches, or knobs, or suitable combinations thereof.

In some embodiments, the results of the milk composition analysis may provide feedback to the user. For example, if the concentration of a critical nutritional component of the milk is found to be present at levels lower than a specific threshold value, the user interface of the sensor unit may display a warning message to the user. The threshold values for the various components of the milk may be calibrated by the sensor unit based on the weight of the infant and the weight of the mother. The feedback messages from the sensor unit may be shared by the user with clinicians via e-mail or short messaging service (SMS), or may be stored onto the data array for the corresponding unique identifier, so that clinicians may access and review the information remotely via a connection through a cloud server.

Communication with Computing Devices

In any of the embodiments disclosed herein, the pumping devices described herein can be configured to communicate with another entity, such as one or more computing devices and/or servers. Exemplary computing devices include personal computers, laptops, tablets, and mobile devices (e.g., smartphones, cellular phones). The servers described herein can be implemented across physical hardware, virtualized computing resources (e.g., virtual machines), or any suitable combination thereof. In preferred embodiments, the servers are distributed computing servers (also known as cloud servers) utilizing any suitable combination of public and/or private distributed computing resources. The computing devices and/or servers may be in close proximity to the pumping device (short range communication), or may be situated remotely from the pumping device (long range communication). Any description herein relating to communication between a computing device and a pumping device can also be applied to communication between a server and a pumping device, and vice-versa.

Figure 13:
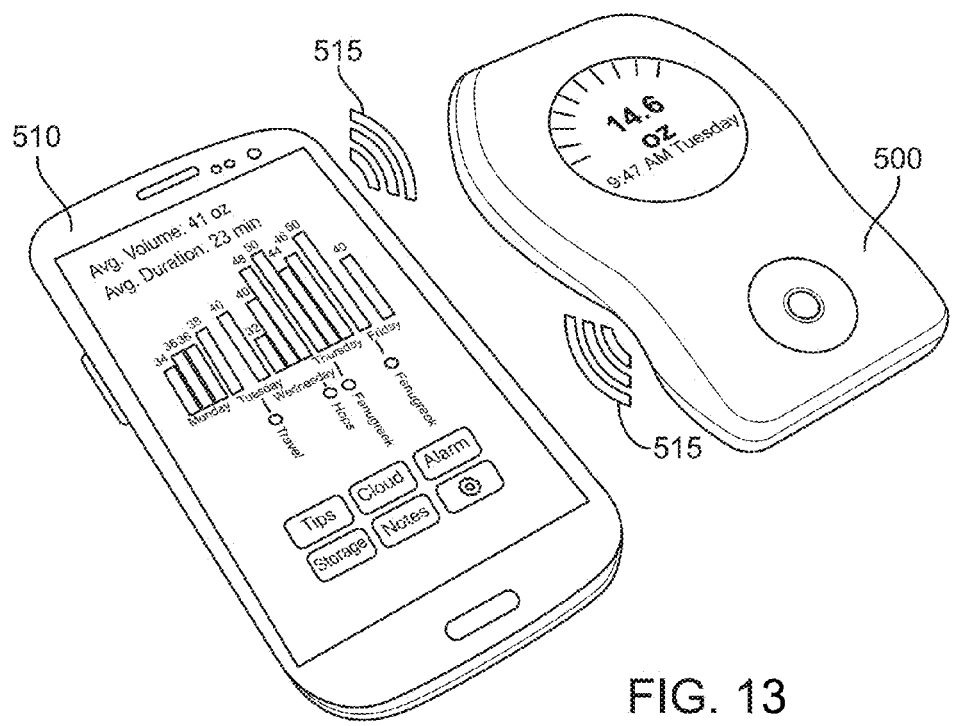
FIG. 13 illustrates short range communication between a controller and a mobile device, in accordance with embodiments.

FIG. 13 illustrates short range communication 515 between the controller 500 of a pumping device and mobile device 510. The communication 515 can utilize wireless communication methods, as described below. In many embodiments, the controller 500 and mobile device 510 are also capable of long range communication.

Figure 14:
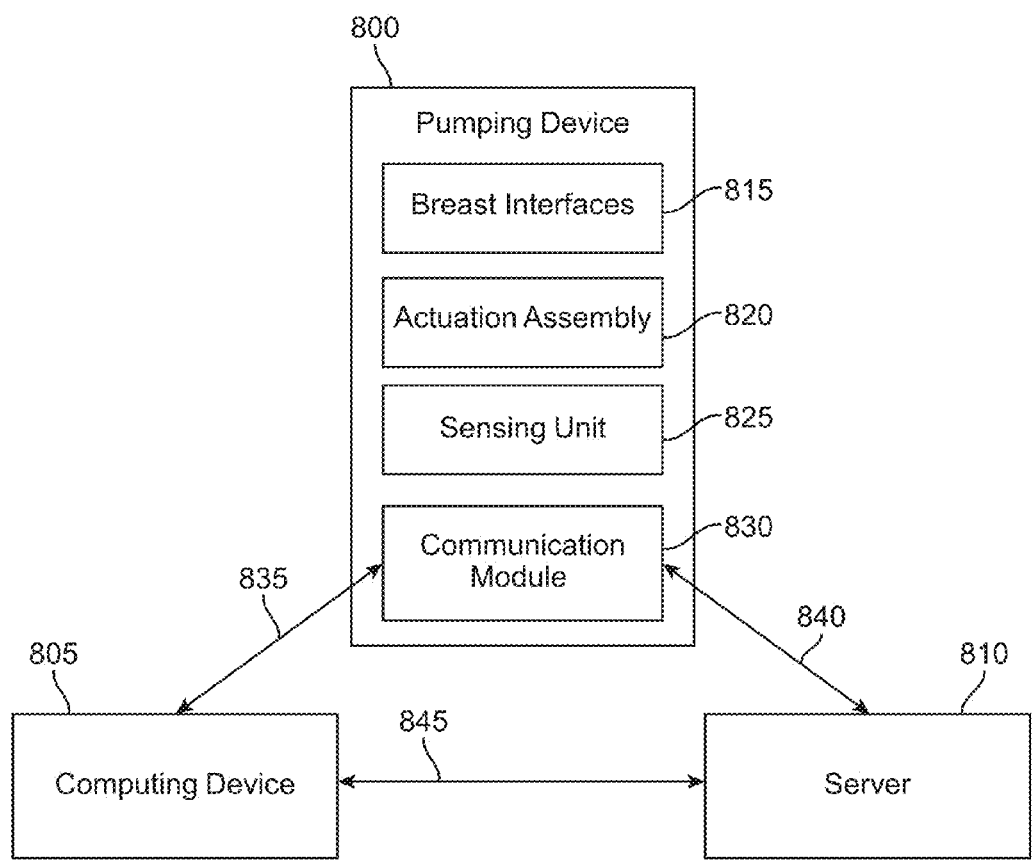
FIG. 14 is a schematic illustration of a pumping device in communication with a computing device and a server, in accordance with embodiments.

FIG. 14 is a schematic illustration of a pumping device 800 in communication with a computing device 805 and a server 810. The pumping device 800 includes one or more breast interfaces 815, an actuation assembly 820, a sensing unit 825, and a communication module 835. Preferably, the communication module 830 is implemented across suitable hardware within a controller of the pumping device (e.g., controller 500). The pumping device 800 can communicate with the computing device 805 and server 810 via the communication module 830. In many embodiments, the communication module 830 is communicably coupled to the computing device 805 and server 810 via first and second data connections 835, 840. Furthermore, the server 810 can be communicably coupled to the computing device 805 via a third data connection 845. Although the pumping device 800 is depicted herein as communicating directly with the computing device 805 and the server 810, other configurations are also possible. For example, the pumping device 800 may communicate with the server 810 indirectly via the computing device 805, or vice-versa. Conversely, the server 810 may communicate with the pumping device 800 indirectly via the computing device 805, and the computing device 805 may communicate with the pumping device 800 via the server 810. Any description herein related to communication between the pumping device 800, the computing device 805, or server 810 can be applied to direct communication as well as indirect communication between these entities.

The data connections 835, 840, and 845 can utilize any communication method suitable for transmitting data between the pumping device 800, the computing device 805, and server 810. Such communication methods can include wired communication (e.g., wires, cables such as USB cables, fiber optics) and/or wireless communication (Bluetooth®, WiFi, near field communication). In many embodiments, data can be transmitted over one or more networks, such as local area networks (LANs), wide area networks (WANs), telecommunications networks, the Internet, or suitable combinations thereof.

In exemplary embodiments, the pumping device 800 transmits milk expression data to the computing device 805 or server 810 (directly or indirectly). The milk expression data can include measurement data generated by the sensing unit 825 of the pumping device 800, as previously described herein. In many embodiments, the pumping device 800 analyzes the measurement data (e.g., using suitable onboard hardware and/or software) and transmits the analysis results to the computing device 805 or server 810. Alternatively, the measurement data can be analyzed by the computing device 805 or server 810, such as using one or more applications. The computing device 805 or server 810 may be associated with data stores for storage of the measurement data and/or analysis results.

The applications (of the computing device 805 or server 810) can also collect and aggregate the measurement data and/or analysis results and display them in a suitable format to a user (e.g., charts, tables, graphs, images, etc.), as previously described herein. Preferably, the application includes additional features that allow the user to overlay information such as lifestyle choices, diet, and strategies for increasing milk production, in order to facilitate the comparison of such information with milk production statistics. The mobile application can also include features that allow the user to control aspects of the pump, such as pump power and pump states (e.g., let-down and stimulate modes), adjust expression pressure and speed, and adjust the size of a breast interface, where the breast interface is automatically adjustable. The application may also have resources for breast feeding moms, such as advice or connection to advice, social aspects such as peer comparisons, and an accessory store for acquiring accessories for the pump. The analysis and display functionalities described herein may be performed by a single entity, or by any suitable combination of entities. For example, in many embodiments, data analysis can be carried out by the server 810, and the analysis results transmitted to the pumping device 800 or computing device 805 for display to the user.

Additionally, the computing device 805 or server 810 can include an application configured to control at least one functionality of the pumping device 800 or a portion thereof (e.g., the actuation assembly 820), such as power, vacuum pressure applied (via the interfaces 815), or speed. For example, the communication module 830 can receive control signals from the computing device 805 and/or sever 810, and transmit the control signals to the actuation assembly 820 to produce the desired actuation. In preferred embodiments, the control signals can be generated using feedback provided by the pumping device 800, such as feedback based on measurement data provided by the sensing unit 825, as previously described herein. Additionally, the computing device 805 or server 810 may implement machine learning techniques with regard to control of the pumping device 800, in order to improve and optimize pumping performance over time.

Furthermore, the pumping device 800, computing device 805, and/or server 810 can be configured to provide notifications reminding the user to express milk. Such notifications can help avoid missed pumping sessions, and thus reduce the incidence of associated complications such as mastitis. The notifications can be generated based on previously collected milk expression data, such as data relating to expression frequency and/or the timing of previous pumping sessions, as well as based on user preferences. Preferably, the notification functionality is included in a suitable application running on the computing device 805 or server 810. For example, the pumping device 800 can send information about the times of pump usage to the computing device 805 or server 810, so that the application can identify when pumping has occurred and set reminders at desired pumping times.

The notifications can be provided using any suitable method and in any suitable format. For example, the notifications can be generated by the computing device 805 or server 810, transmitted to the pumping device 800 (e.g., to the communication module 830), and displayed to the user (e.g., on a display of the pumping device 800, such as the display screen 505). Conversely, the notifications can be generated by the pumping device 800 and transmitted to the computing device 805 and/or server 810. In many embodiments, the notifications are displayed to the user by the computing device 805. Alternatively, the pumping device 800, computing device 805 and/or sever 810 can provide the notifications to the user using other methods. For example, the notifications can be sent to an email address, via short message service (SMS) to a smartphone or other mobile device associated with a cellular phone number, or to a web page accessible by the user.

Other types of data can also be transmitted between the pumping device 800, computing device 805, and/or server 810. For example, in many embodiments, firmware updates for one or more components of the pumping device 800 can be transmitted to the pumping device 800 from the computing device 805 and/or server 810.

Figure 17:
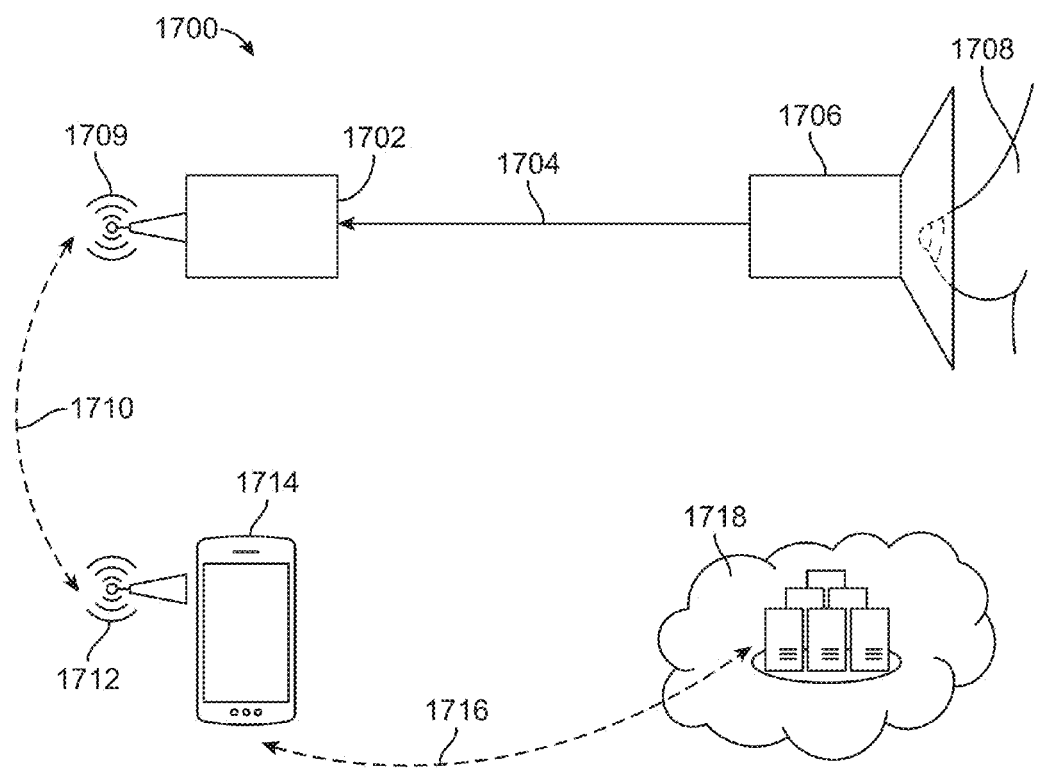
FIG. 17 illustrates a schematic diagram of a system for expression of milk.

FIG. 17 illustrates another exemplary embodiment of a system for expression of milk or for monitoring other fluids. The system 1700 includes a pump unit 1702, a distal assembly 1706 (sometimes also referred to as an interface in this specification), wireless communication transmitters and receivers 1709, 1712, a computing device 1714 and a remote server 1718. The pump unit 1702 may be any of the pump units described in this specification or known in the art, and the distal assembly 1708 also may be any of those described herein or known in the art. The distal assembly 1706 is preferably sized and shaped to conform to the target anatomy, which in this exemplary embodiment is a breast 1708. The pump unit 1702 actuates 1704 the distal assembly 1706 to cause expression of milk from breast 1708 using any of the actuation mechanism disclosed herein. A transmitter 1709 is preferably disposed on the pump unit or adjacent thereto and is configured to transmit data 1710 (or any other data generated, e.g. expressed milk data) from the pump unit to a receiver 1712 on the computing device 1714. The data may be transmitted wirelessly using methods known in the art such as those disclosed in this specification. In alternative embodiments, a hard connection such as with a USB cable may be used to operably couple the pump 1702 and computing device 1714 together. The computing device may be a smart phone, tablet, personal computer, or any other electronic computing device that can display the data transmitted from the pump unit 1702. The computing device may also transmit information back to the pump unit to help control operation of the distal assembly. The computing device 1714 may also communicate 1716 with a remote server 1718 which may store or display the data. Access to the remote service 1718 may be by the Internet or by other means known in the art and thus the cloud based data may be readily accessed from any other device with Internet access.

Figure 18:
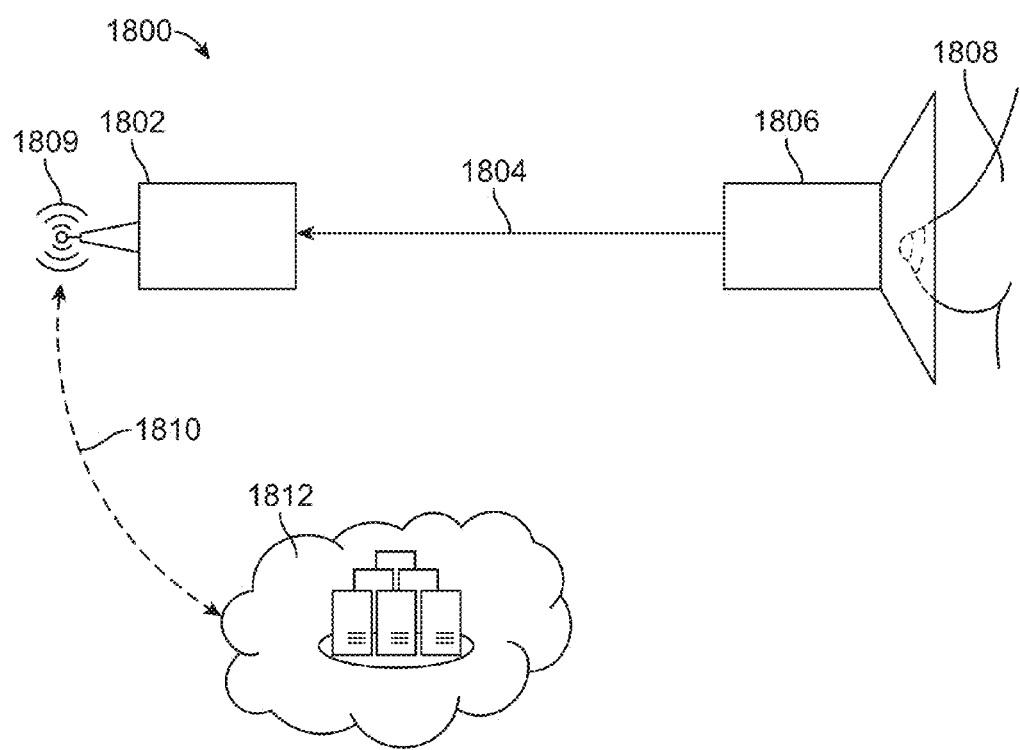
FIG. 18 illustrates another exemplary embodiment of a system for expression of milk.

FIG. 18 illustrates another exemplary embodiment of a system 1800 for expression of milk. In this embodiment, the system 1800 includes a pump unit 1802, a distal assembly 1806 and a cloud based or remote server 1812. The pump unit 1802 may be any of the pumps disclosed herein and it is operably coupled with the distal assembly 1806 which is sized and shaped to conform to the target, such as breast 1808. The distal assembly may be any of the distal assemblies described herein. The pump unit 1802 actuates 1804 the distal assembly using any of the mechanisms disclosed herein to cause expression of milk from breast 1808. The pump unit 1802 also includes a transmitter and receiver 1809 for transmitting pump data 1810 or any other data generated (e.g. expressed milk data) to a remove server 1812, which in this embodiment is a cloud based server. Thus, the data may be transmitted to the remote service via the Internet, and accessed from the cloud based server by the pump 1802 or any other computing device via the Internet. Preferably communication with the cloud based server is by wireless communication.

FIGS. 19A-19C illustrate exemplary computing device displays 1904. For example, FIG. 19A illustrates an exemplary display on a mobile phone 1902 and graphically illustrates milk production, the time of the last pumping session, a graphic of goal attainment, and a graphic illustrating the fluid consumption of the user. Additionally, the display 1904 may also provide user encouragement or user feedback based on the amount of milk production. FIG. 19B is an enlarged view of the display 1904 in FIG. 19A. FIG. 19C illustrates additional information that the display 1904 may show when a touch screen is actuated (e.g. by swiping or touching the screen). For example, the volume of the milk expressed is indicated after the "Last Pumping Session" section of the display is selected. Some or all items may be expanded, as also indicated in FIG. 19C. Additional information, or in some situations, less information may be displayed as desired.

Figures 20A, 20B:
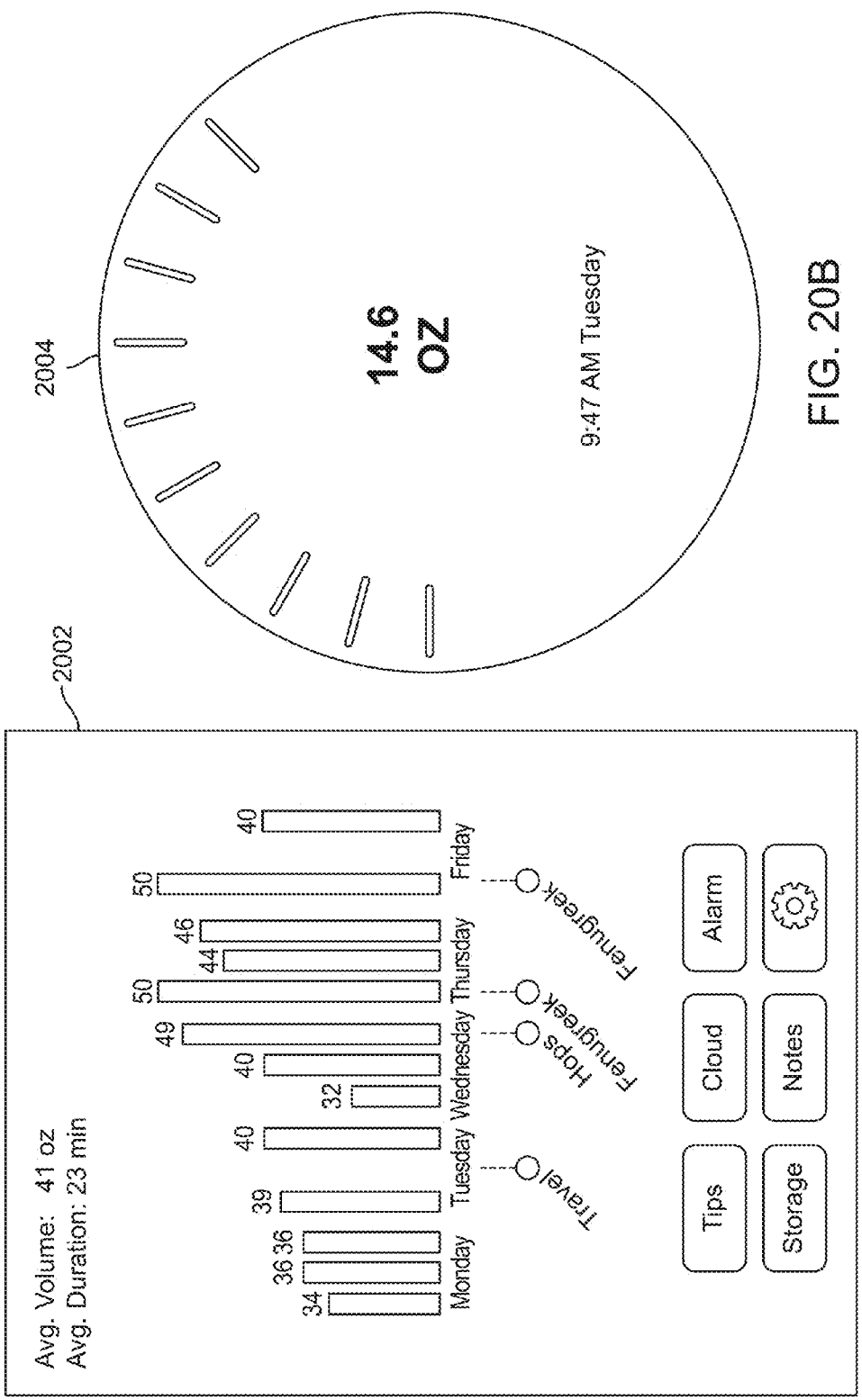
FIGS. 20A-20B illustrate exemplary displays in a milk expression system.

FIGS. 20A-20B illustrate other exemplary displays which may be used in a milk expression system. For example, FIG. 20A is an exemplary display 2002 on any of the computing devices disclosed herein and operably coupled with the pump unit. The display may indicate an average volume of milk expressed over any time period, along with an average duration of the expression session during that same time period. Graphics may be used (e.g. bar chart, pie chart, x-y plot, etc.) to show volume expressed during individual sessions over the course of several days, here Monday through Friday. The display may allow a user to annotate the display so that missed sessions may be accounted for, for example if a session is omitted due to traveling, the display may show travel during that time period. Other annotations may also be made, such as when certain foods or nutritional supplements are taken, here hops or fenugreek. This allows the user to recall when expressed milk samples were obtained relative to the consumption of the food or nutritional supplements. The display may have other functional buttons such as for obtaining tips, accessing the cloud, setting an alarm, making notes, storing data, or establishing system preferences. Communication between the computing device and the pump unit in FIGS. 20A-20B is discussed more thoroughly above in relation to FIG. 13.

FIG. 20B illustrates an exemplary display 2004 that may be on a computing device in the system, or more preferably that is on any of the pumps disclosed herein. The display 2004 is similar to a dashboard style gauge and indicates the volume of fluid expressed and collected and the time. Other information may also be displayed including but not limited to that disclosed herein.

Inventory Tracking and Management

The relatively short shelf-life of expressed breast milk, combined with the fluctuating supply and demand of the milk over time, can pose challenges for the mother in building and maintaining an inventory of milk. The breast milk expression device described herein may be provided as a system having features that facilitate the tracking and management of an inventory of expressed milk.

Figure 25:
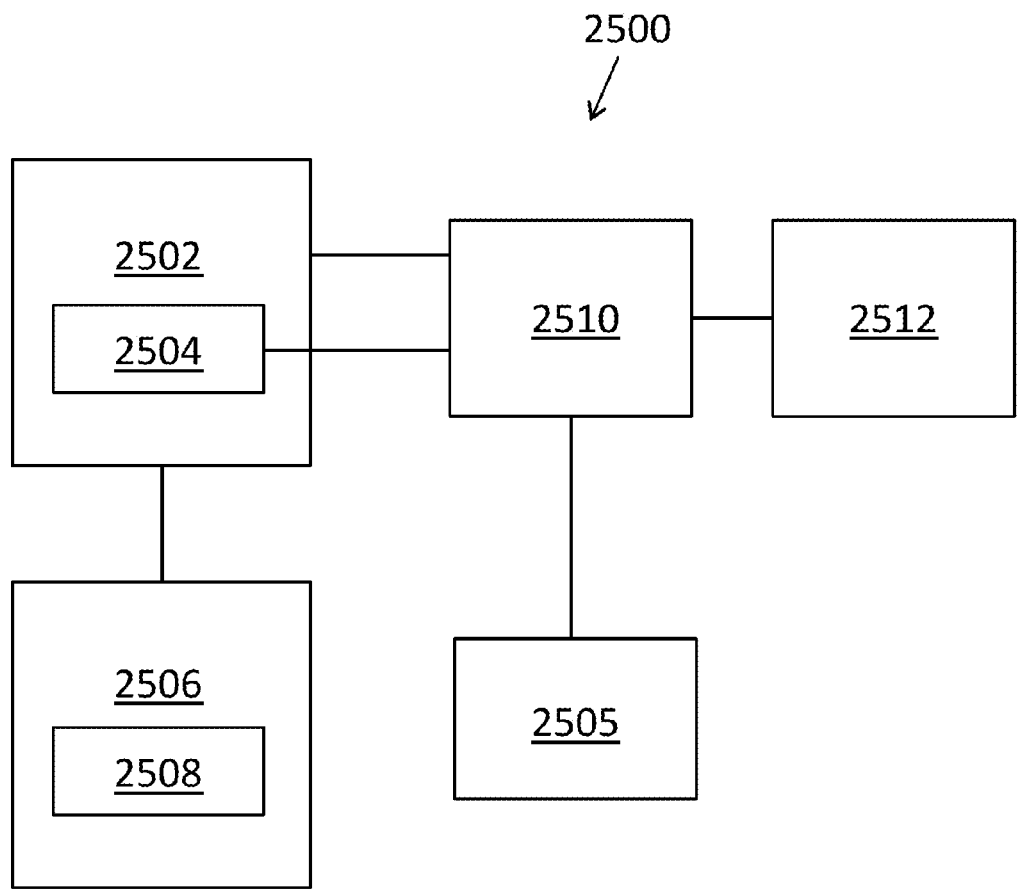
FIG. 25 illustrates an exemplary embodiment of a milk expression and inventory management system.

FIG. 25 illustrates an exemplary embodiment of a milk expression and inventory management system 2500. The system comprises a breast milk expression device 2502 fluidly coupled to a collection reservoir 2506 having a unique identifier 2508 as described herein, where the unique identifier may be pre-labeled onto the reservoir or may be manually labeled by the user. The reservoir may comprise a bottle and/or a bag, and can be removably coupled to the expression device to receive and collect the expressed milk. The system may comprise an integrated sensor unit 2504 integrated with the expression device 2502 as described herein, for example by being affixed to an exit valve or flap valve of the expression device. The sensor unit may comprise one or more of any of the sensors described herein. For example, the sensor unit may measure the volume of milk expressed during the pump session, or the concentration of one or more compounds of breast milk. Alternatively or in combination with the integrated sensor unit 2504, the system may comprise a separate sensor unit 2505, which can be used to characterize the expressed milk after the milk has been collected in the reservoir 2506. The system further comprises a peripheral device 2510 connected to the expression device, the peripheral device having suitable hardware for collecting, processing, and storing the milk expression data as described herein, as well as for analyzing the results obtained from processing the expression data. The peripheral device may also collect basic pump session data during expression, such as the time and date of the pump session and the duration of pumping. The peripheral device may be a controller of the expression device, and/or a computing device such as a mobile phone, tablet, or personal computer having an application programmed to control and/or communicate with the expression device.

Figure 27:
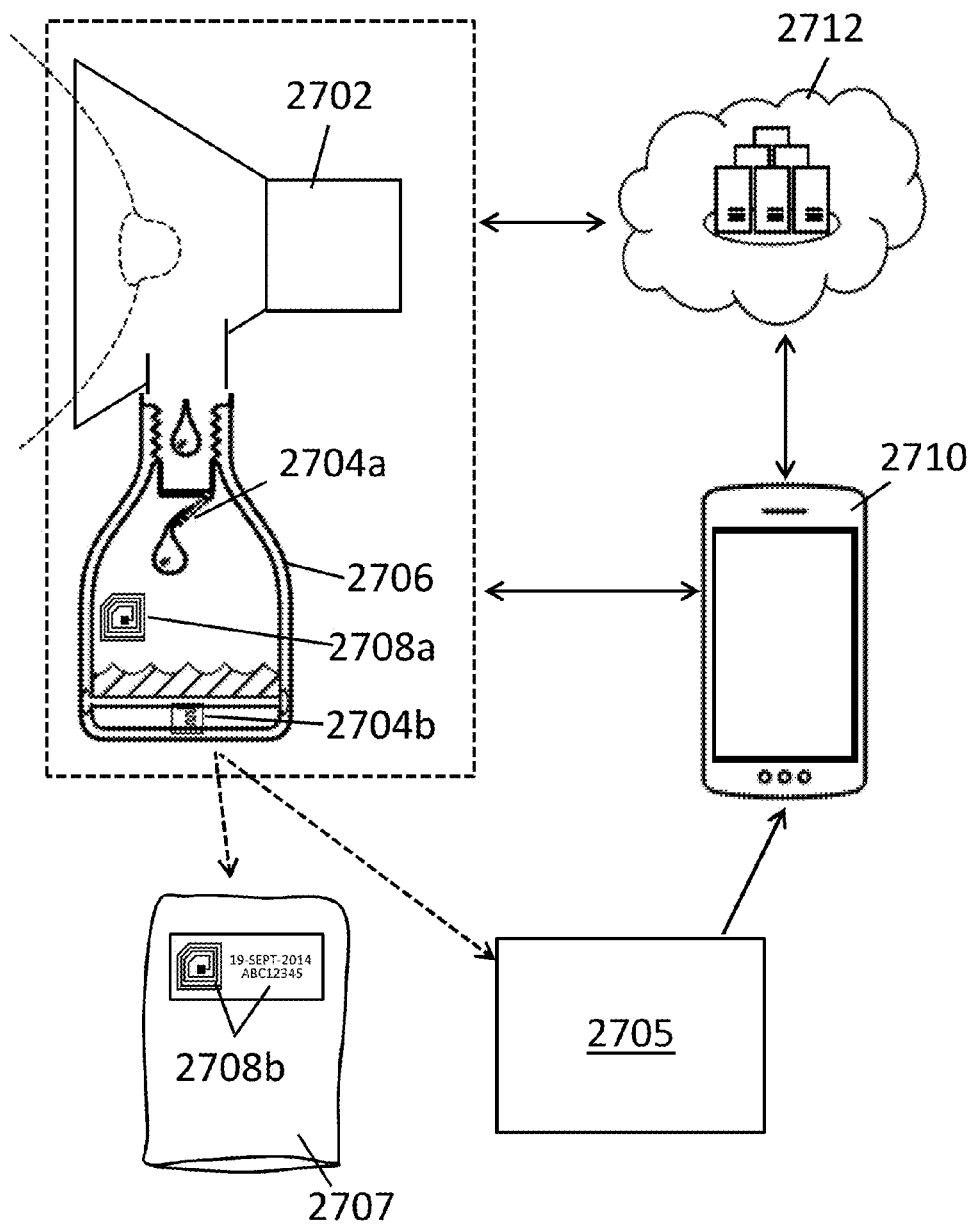
FIG. 27 illustrates another exemplary embodiment of a milk expression and inventory management system.

FIG. 27 illustrates another exemplary embodiment of a milk expression and inventory management system 2700. The system comprises an expression device 2702 such as any expression device described herein, a collection reservoir 2706 fluidly coupled to the expression device, and a peripheral device 2710 operably coupled to the expression device and/or the collection reservoir. The expression device may optionally comprise an integrated sensor unit 2704a, such as any sensor unit as described herein, configured to be integrated with the expression device. In addition, the collection reservoir may optionally comprise an integrated sensor unit 2704b, such as any sensor unit as described herein, configured to be integrated with the collection reservoir. The integrated sensor unit can be configured to measure one or more attributes of the expressed milk during the pumping session, such as the volume of expressed milk or the concentration of one or more components of breast milk. If the collection reservoir is also used as the storage reservoir, the integrated sensor unit can also be configured to measure the volume of the milk during and/or after feeding the milk to a child. In such embodiments, the integrated sensor unit can not only measure the volume of milk expressed into a collection reservoir, but also measure the volume of milk exiting the collection/storage reservoir and therefore the volume of milk remaining in the reservoir after a feeding session. The system may optionally comprise a separate sensor unit 2705 as described herein, the separate sensor unit configured to characterize the expressed milk after the milk has been collected in the reservoir 2706. The expression device, the one or more integrated sensing units, and the separate sensor unit may be in communication with the peripheral device via wired or wireless connections. The system may further comprise a server 2712 in communication with the peripheral device and/or the expression device via a wireless connection. The collection reservoir may comprise a unique identifier 2708a as described herein, which may be pre-labeled onto the reservoir and/or labeled onto the reservoir by the user. The collection reservoir may be used as the storage reservoir for the collected milk, wherein the opening the collection reservoir may be securely sealed and the collection reservoir may be transferred to a storage location (e.g., refrigerator or freezer). Optionally, the system may comprise one or more storage reservoirs 2707 separate from the collection reservoir, such that a user may transfer milk collected in the collection reservoir to a storage reservoir after expression of the milk. The separate storage reservoir 2707 may comprise a unique identifier 2708b such as any unique identifier described herein, which may be pre-labeled onto the storage reservoir or manually labeled by the user.

During a pump session, an integrated sensor unit can collect data by measuring one or more attributes of the breast milk as it is expressed and collected in the collection reservoir. When the pump session is complete, the sensor unit can send the collected data to the peripheral device, where the data may be digitally coupled to the basic pump session data. The peripheral device can then prompt the user if she would like to add the milk expressed during this session to her inventory. If the user selects the option to add the milk to the inventory, the peripheral device can prompt the user to provide the unique identifier of the reservoir, for example by manually entering in a user-assigned code or by scanning in a pre-printed label. For example, the reservoir may comprise a bag having a pre-printed QR code, and providing the unique identifier may comprise scanning the QR code with a mobile phone running a QR code scanning application. When the peripheral device obtains the unique identifier for the milk expressed during the pump session, the unique identifier can be digitally coupled to the data gathered for the pump session, including the time and date of the pump session, duration of pumping, volume of expressed milk, and/or compositional attributes of the expressed milk.

The expressed milk may also be analyzed after the pump session has been completed, using the separate sensor unit. The sensor unit may be a stand-alone unit with its own user interface, or it may be a unit configured to be coupled to and operated by the peripheral device. A small sample of the milk may be removed from the reservoir and tested using the sensor unit as described in further detail elsewhere in this specification. The sensor unit may prompt the user to provide the unique identifier of the sample (from the reservoir or from the test strip or sample container), and the data generated by the sensor unit may then be digitally coupled to the unique identifier. The digitally coupled data may be transmitted to the peripheral device via a wired connection or wireless connection. The peripheral device may further bundle the data transmitted from the separate sensor unit with the data for the unique identifier already stored on the peripheral device, such as the basic pump session data and data generated from an integrated sensor unit.

The complete array of the bundled data may be stored on a local drive of the peripheral device, such as the local drive of the controller or of a computing device in communication with the controller. Alternatively or in combination, the bundled data may be stored on a remote server, wherein the data may be transmitted to the remote server from the peripheral device via a wireless connection as described in detail elsewhere in this specification.

For dual expression devices, i.e., devices comprising two breast interfaces and two corresponding collection reservoirs, each reservoir may have a distinct unique identifier, and fluid collection, quantification, and inventory management may be performed separately for milk expressed from each breast. Alternatively, if the user combines the milk expressed from the two breasts into a single reservoir (e.g., one of the collection reservoirs or a separate storage reservoir), a single unique identifier may be associated with the combined milk from both breasts, stored in the single reservoir.

In embodiments wherein the unique identifier comprises an RFID tag, the pump system may further comprise an RFID reader configured to communicate with one or more of the peripheral device and the server. The RFID reader may be a stand-alone device disposed at a convenient location for tracking milk storage reservoirs as they are added to and removed from storage locations (e.g., attached to the door of the refrigerator/freezer, placed on a kitchen counter, etc.). Alternatively, the RFID reader may be integrated with one or more devices of the system, such as the peripheral device or an organizer system for the milk storage reservoirs, as described in further detail elsewhere herein. The RFID reader may be configured to communicate with the peripheral device and/or the server via a wired or wireless data connection. When the RFID reader scans an RFID tag associated with a storage reservoir, the reader may directly access the milk inventory stored on the peripheral device and/or the server and make appropriate updates to the inventory as described herein. Alternatively or in combination, the RFID reader may send information regarding the detected changes in inventory to the application of the peripheral device. This information may be presented to the user via the application in real time, or periodically at pre-determined times of the day. The user may be prompted to acknowledge the updates to the inventory, or confirm that the updates should be made. Optionally, the RFID reader may comprise means for users to provide inputs regarding the destination of a scanned storage reservoir. For example, after scanning a storage reservoir, the user may be prompted to push a button disposed on the RFID reader to indicate whether the scanned reservoir is to be placed in the refrigerator/freezer (storage), in the garbage (dispose), or in the baby's belly (fed). The RFID reader may accordingly update the inventory with changes, if any, in the storage location of the scanned inventory item.

Figure 28:
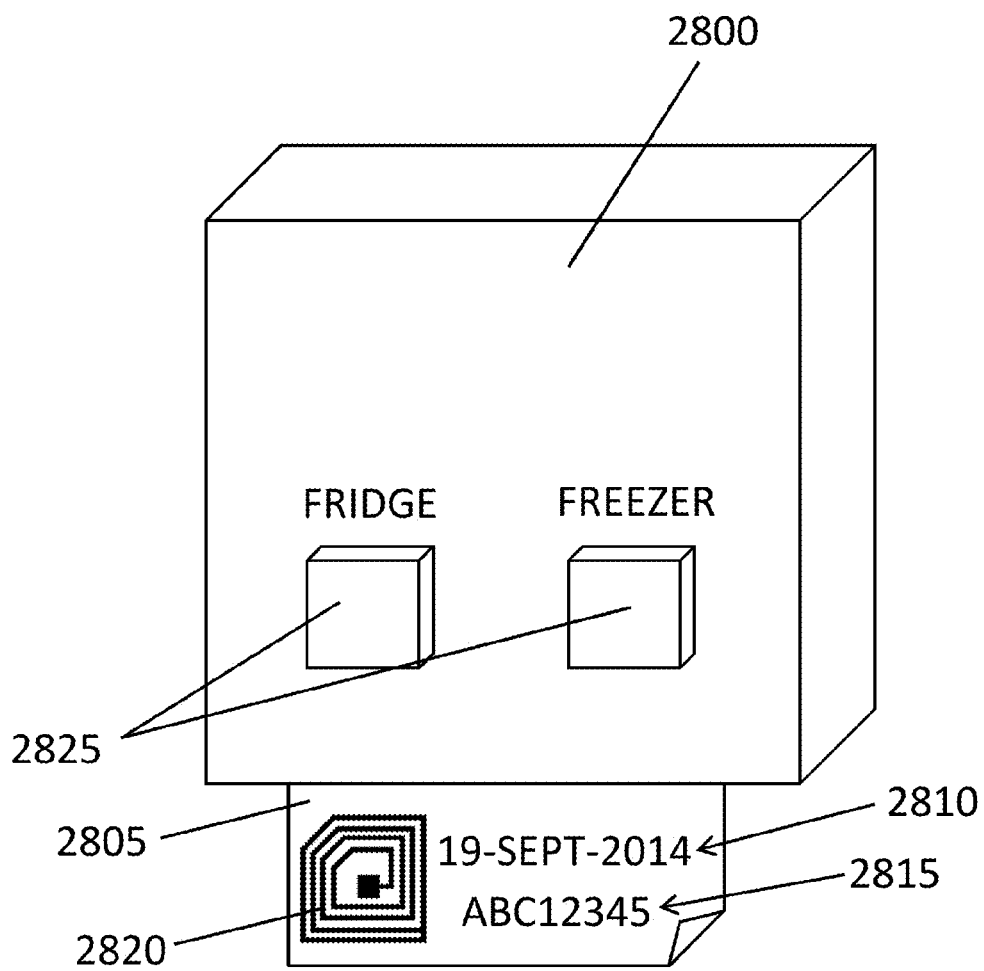
FIG. 28 illustrates an exemplary embodiment of a label printer which may be optionally incorporated with an inventory management system.

FIG. 28 illustrates an exemplary embodiment of a label printer 2800 which may be optionally incorporated to generate labels for storage reservoirs. The label printer can be configured to print labels 2805 comprising one or more unique identifiers that are recognizable by human eye, such as alphanumeric text codes. For example, the text codes may comprise a date code 2810 and/or an inventory code 2815. Optionally, the labels may additionally comprise a machine-readable identifier that is pre-printed or otherwise provided on the labels, such as a bar code, QR code, or RFID tag 2820. The label printer can be further configured to communicate with a peripheral device, a server, or both, via a wired or wireless data connection, to access and update the milk inventory stored on either or both of the peripheral device and the server. To generate a label for a new storage reservoir, a user may simply press a button disposed on the printer. The one or more unique identifiers of the reservoir on the newly printed label may be provided to the application of the peripheral device via the data connection, thereby generating a new inventory item in the inventory corresponding to the storage reservoir. Optionally, the label printer may comprise a plurality of buttons 2825 each indicating a different storage location for the storage reservoir, and the user may push a button corresponding to the desired storage location to print the label. In such a configuration, the label printer can automatically update the inventory item with the storage location of the reservoir. The printed labels may be configured to adhere to a storage reservoir, for example by way of an adherent back side, such that the user can affix the printed label to the storage reservoir containing the expressed milk. The labeled reservoir can then be placed in the appropriate storage location. The label printer can simplify the generation of unique identifiers and automate the creation of new inventory items based on the newly generated identifiers. Further, the human-readable identifiers provided on the printed labels can assist a user in selecting the desired storage reservoir, by facilitating visual identification of desired reservoir.

Figure 29:
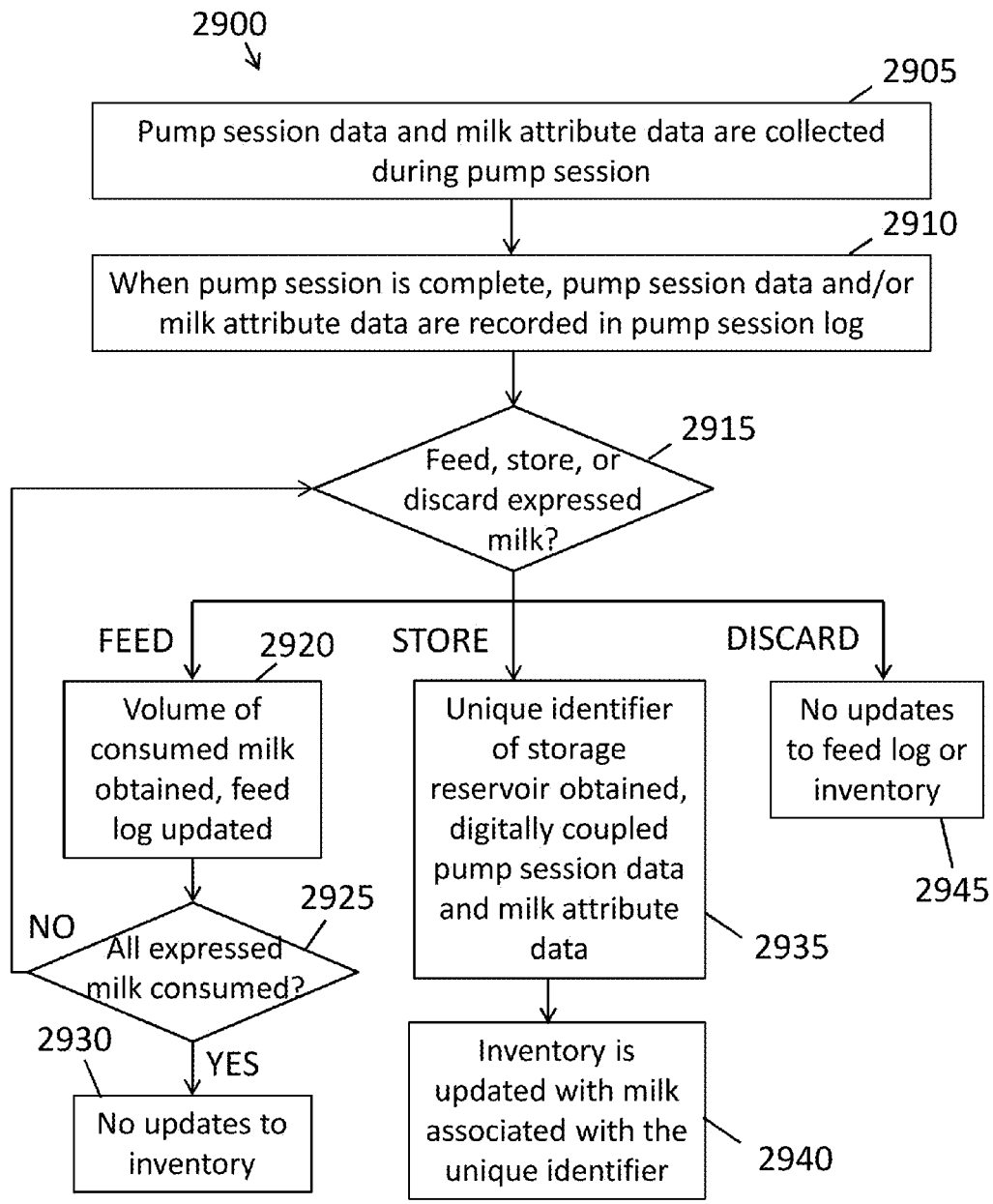
FIG. 29 shows an exemplary method of adding an item to a breast milk inventory.

FIG. 29 shows an exemplary method 2900 of adding an item to a breast milk inventory. In step 2905, pump session data and/or milk attribute data are collected during a pump session. The pump session data may be collected by a peripheral device in communication with the expression device, and may comprise the date and time of pumping and the duration of pumping, for example. The milk attribute data may be collected by an integrated sensor unit disposed on one or both of the expression device and the collection reservoir, and may comprise the volume of expressed milk and/or the composition of the expressed milk.

In step 2910, following the completion of the pump session, the pump session data and/or the milk attribute data are recorded in a pump session log. The pump session log, which can maintain a record of every pump session performed by the expression device, may be stored on a local drive of the peripheral device and/or on a remote server. In preferred embodiments, the peripheral device provides an inventory management application, programmed to track and manage the user's breast milk inventory. The application may comprise the same application that is used to control and/or communicate with the expression device, or the application may be a separate application that can be incorporated with any breast milk expression device, including commercially available systems. The application can be programmed to display information, prompt user action, and receive user input regarding milk inventory management. The user may access and view pump session data, milk attribute data, and/or the pump session log through the application.

In step 2915, the application determines whether the expressed milk is to be fed, stored, or discarded. For example, the application may prompt the user to select an action (feed, store, or discard). Alternatively, the application may obtain the information from another device in communication with the peripheral device, such as an RFID reader comprising user inputs for indicating the destination of a scanned storage reservoir as described herein. Alternatively, the application may comprise instructions to determine this information automatically. For example, the application may be programmed to assume that the expressed milk is to be stored if the child has been fed within a certain time window (e.g., 1 hour) from the current pump session, or the application may be programmed to assume that the expressed milk is to be discarded if the milk attribute data indicates that the expressed milk is unsuitable for feeding (e.g., alcohol level exceeds a pre-set threshold).

In step 2920, wherein the expressed milk is fed to the child, volume of milk consumed by the child is obtained, and a feed log for the user is updated accordingly. The application may prompt the user to input the volume of consumed or remaining milk, or the volume of consumed or remaining milk may be automatically determined via one or more methods as described herein, such as via a reservoir comprising an integrated sensing unit. The feed log, which can help a user maintain a record of her child's feeding sessions, may then record information related to the feeding session, such as the date and time of feeding, the volume of milk consumed, the expression date of the milk consumed, etc. The feed log may be stored on a local drive of the peripheral device and/or of a remote server.

In step 2925, the application determines, based on step 2920, whether all of the expressed milk has been consumed. In step 2930, wherein all of the expressed milk has been consumed, no updates are made to the milk inventory. If the expressed milk has not been completely consumed and the volume of remaining expressed milk is non-zero, the user may be directed back to step 2915, wherein the user is prompted to select an action for the remaining milk.

In step 2935, wherein the expressed milk is stored for later feeding, a unique identifier of the storage reservoir for the expressed milk is obtained from the user. For example, the user may be prompted to manually provide a user-assigned, human-readable code through the application, the user may generate an identifier by printing a label using a label printer as described herein, or the user may scan in a machine-readable code (e.g., scan a bar code or a QR code with a mobile phone, or scan an RFID tag with an RFID reader). The obtained unique identifier is then digitally coupled with the pump session data and/or milk attribute data for the expressed milk. If the expressed milk has been partially fed to the child, the milk attribute data associated with the unique identifier can comprise the remaining volume of expressed milk after feeding. Optionally, the storage location of the milk may also be obtained, for example by prompting the user to provide the storage location through the application, or by obtaining the information from another device configured to receive user input (such as a label printer or milk organizer as described herein). The obtained storage location may then be associated with the unique identifier.

In step 2940, the milk inventory is updated with the milk associated with the unique identifier in step 2935. The unique identifier may or may not already exist in the inventory, depending on whether the user has placed the freshly expressed milk in a new storage reservoir with a new unique identifier, or has combined the freshly expressed milk with previously expressed milk already present in the inventory (e.g., milk expressed during previous pumping sessions in the same calendar day). If the unique identifier does not already exist in the inventory, a new inventory item associated with the unique identifier can be created and added to the inventory. If the unique identifier already exists in the inventory, the inventory item associated with the unique identifier can be updated to incorporate the information for the freshly expressed milk. For example, the volume of milk for the inventory item can be increased by the volume of the freshly expressed milk.

In step 2945, wherein the expressed milk is discarded, no updates are made to the feed log or the inventory, though the pump session data and/or the milk attribute data may still be recorded in the pump session log.

The steps of method 2900 are provided as an example of a method of adding an item to a milk inventory in accordance with embodiments. A person of ordinary skill in the art will recognize many variations and modifications of method 2900 based on the disclosure provided herein. For example, some steps may be added or removed. One or more steps may be performed in a different order than as illustrated in FIG. 29. Some of the steps may comprise sub-steps. Many of the steps may be repeated as many times as appropriate or necessary.

When the stored milk is ready to be fed to an infant, the user may utilize the peripheral device to determine which batch of expressed milk to select. Inventory management by the peripheral device can follow a first-in, first-out rule, wherein the first item to enter the inventory is the first item to leave. Under this structure, the oldest expressed milk in the inventory may be identified as the next to be fed. Exceptions may apply for milk in the inventory whose storage duration has surpassed a pre-set limit on the length of time the milk may be stored. For example, if the inventory contains 10 batches of milk expressed on consecutive days (day 1-day 10), but the storage duration limit is set to 8 days, the batches expressed on days 1 and 2 may be identified as batches to be discarded, and the batch expressed on day 3 may be identified as the batch to be fed.

An application of the peripheral device may comprise an algorithm to sort through the inventory of milk and identify milk to be discarded and/or milk to be fed next. The algorithm can use the unique identifier associated with each batch of expressed milk in order to manage the inventory. For example, the algorithm may compare the expression date for each batch with the current date, calculate the difference in the number of days, sort the inventory by this calculated difference, and identify the batch with the largest difference (falling under the expiry threshold) as the batch to be fed next.

For embodiments wherein the unique identifier comprises a user-assigned, manually labeled identifier, the peripheral device may simply present the selected unique identifier to the user via its display, and the user may visually identify and select the bag bearing the corresponding identifier from her inventory. The user can then withdraw the recommended bag from inventory so that the milk inventory is updated. This may be particularly helpful when milk is entered into inventory at one location and withdrawn from a second location. Also, the system can identify expired milk and help ensure that it is discarded. For embodiments wherein the unique identifier comprises a scannable code, such as a barcode or QR code, the application of the peripheral device may comprise an algorithm to help the user visually identify the bottle or bag presenting the selected unique identifier. For example, the algorithm may scan a bag of expressed milk using a camera coupled to the peripheral device, identify the expression date of the bag via its unique identifier, and determine whether or not the bag is the next to be fed in the inventory. The algorithm can then overlay a label on the display screen of the peripheral device to show the status of the bag within the inventory. For example, if the bag should be discarded, the overlaid label can be a red X. If the bag is the next to be fed, the overlaid label can be a green O or number 1. If the bag is the third in line to be fed, the overlaid label can be a green number 3.

Figure 26:
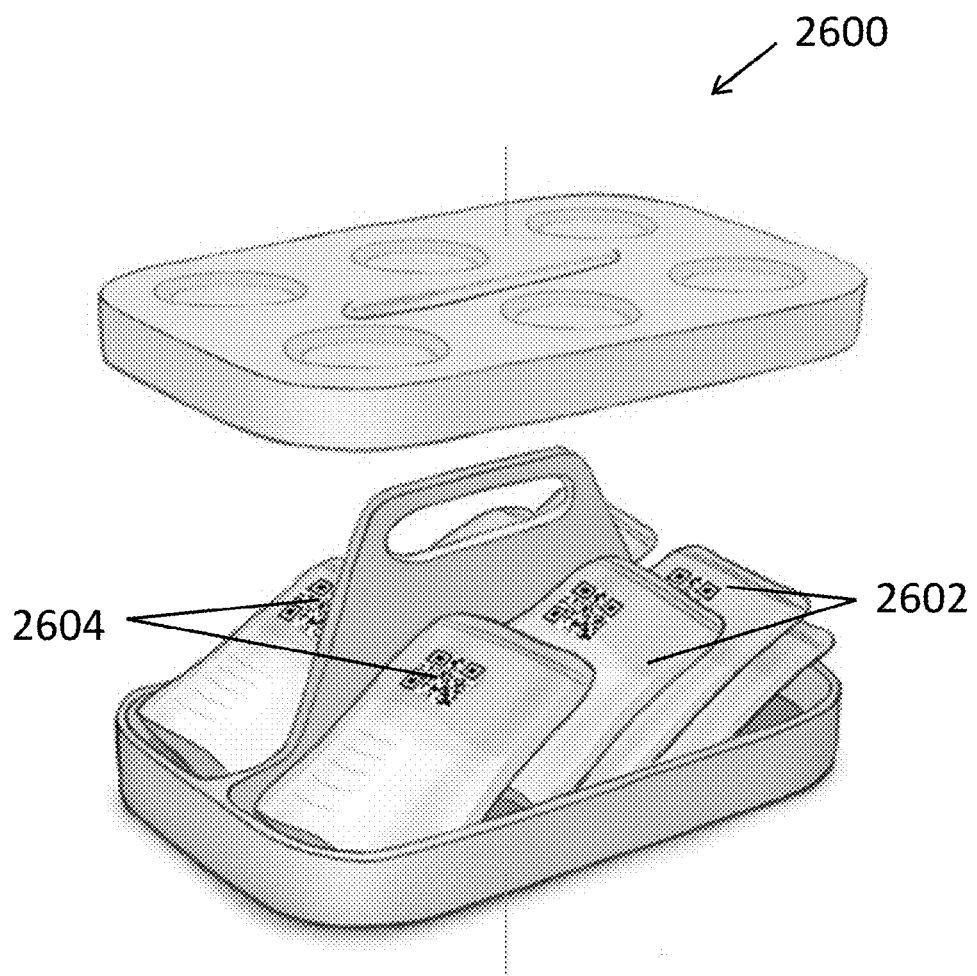
FIG. 26 illustrates an exemplary embodiment of a storage configuration for expressed milk reservoirs having unique identifiers.

The reservoirs containing the expressed milk may be stored in a configuration that facilitates the visualization of the reservoirs by the user or by a peripheral device. FIG. 26 illustrates an exemplary embodiment of a storage configuration 2600 for expressed milk reservoirs 2602 having unique identifiers 2604. The bags 2602 can be disposed in a configuration that allows their unique identifiers to be visible from the top, as shown in the figure. The peripheral device can then be used to visualize the entire inventory at the same time, displaying over each unique identifier the overlaid screen label showing its inventory status, as described herein. The reservoirs may be bottles instead of bags, and the unique identifiers may be disposed on the tops of the bottles for easy visualization.

In still other embodiments, an augmented reality system may facilitate inventory management. Once the expressed milk has been collected in containers having a unique identifier, an operator may quickly scan the entire inventory to capture all the unique identifiers. An image of the inventory may be captured with a camera phone, or wearable computing device and an indicator may be generated by the system and overlaid on top of the image of the inventory to indicate which container is to be used next, or which containers should be discarded. For example, a green line may highlight the next container to use, while a red line may indicate which containers to throw away. Other display units may also be used to help visualize the inventory management queues provided. For example, Google Glass may be used and to provide visual overlays or other visual cues to the user.

When the user confirms that the batch of milk bearing the selected unique identifier has been fed to the infant and removed from the inventory, the data array associated with the unique identifier may be removed from the live or available inventory.

Figure 30A:
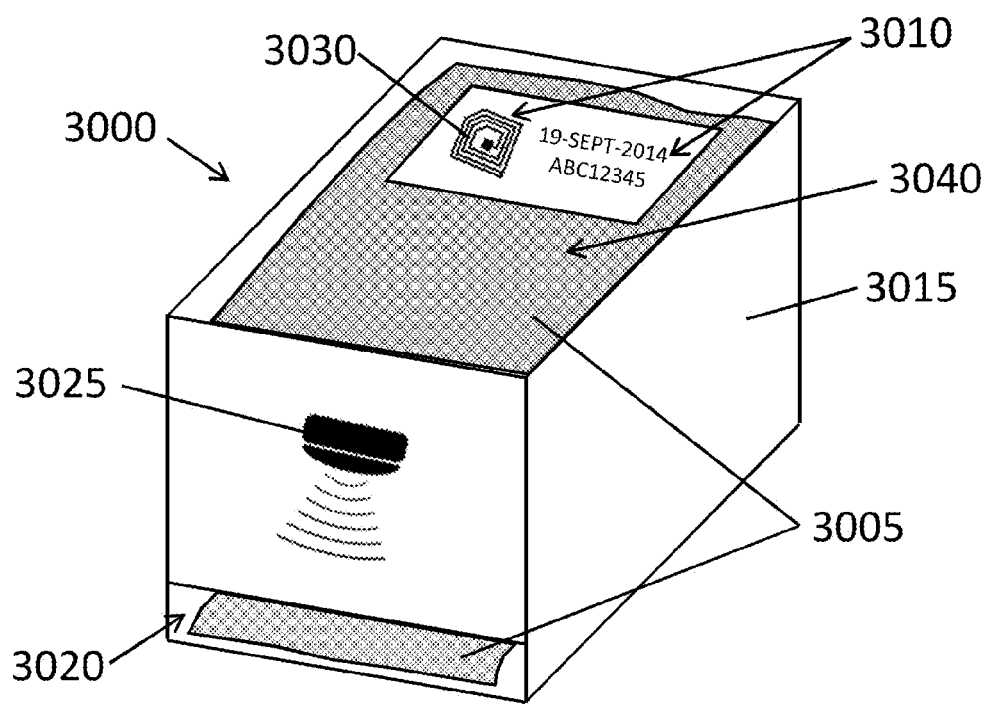
FIG. 30A is a perspective view and FIG. 30B is a side cross-sectional view of an exemplary storage reservoir organizer.
Figure 30B:
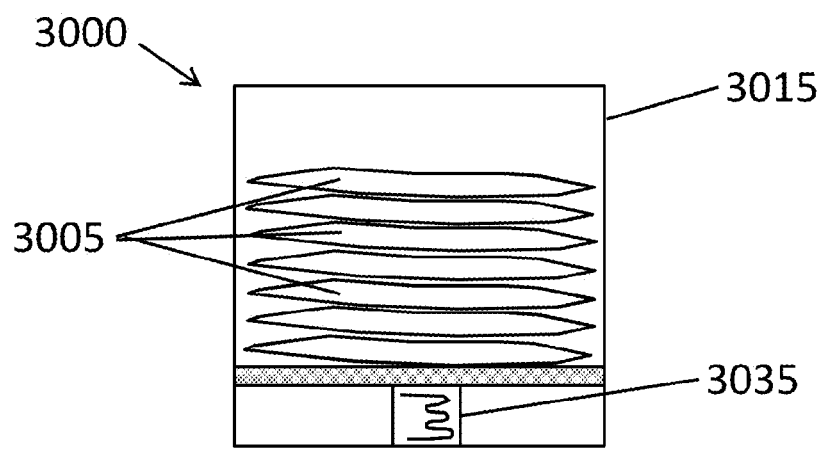

FIGS. 30A-30B illustrate another exemplary embodiment of a storage configuration 3000 for storage reservoirs 3005 having one or more unique identifiers 3010. FIG. 30A shows a perspective view of a storage reservoir organizer 3015, and FIG. 30B shows a side cross sectional view of the organizer 3015 of FIG. 30A. In this configuration, a plurality of storage reservoirs can be stored stacked on top of one another within the organizer, as shown in FIG. 30B wherein the storage reservoirs comprise bags. The shape and dimensions of the organizer may differ from the illustrated embodiment, depending on the shape and dimensions of the storage reservoirs. The organizer can be shaped and sized to have a footprint that substantially matches the footprint of a single storage reservoir in the storage configuration, such that a plurality of storage reservoirs can be stacked one on top of another. For example, if the storage reservoirs comprise bottles, the organizer may have a narrower footprint and a greater height to accommodate the bottles laid on their sides and stacked on top of one another. The reservoir organizer may be configured to fit within a compartment of a refrigerator or freezer, such as on a shelf or in the door. A user may place a storage reservoir inside the reservoir organizer through a top opening 3040 at the top of the organizer, wherein the top opening may be sized to receive the storage reservoirs one at a time. Accordingly, the first reservoir to be placed in the organizer, containing the oldest milk, can end up at the bottom of the stack of reservoirs, whereas the last reservoir to be placed in the organizer, containing the newest milk, can end up at the top of the stack. The organizer can comprise a bottom opening 3020 at the bottom of the organizer, through which the reservoir at the bottom of the stack may be withdrawn. Thus, the stacked storage configuration can facilitate a first-in, first-out system of organization for the expressed breast milk, wherein the user first removes the reservoir containing the oldest expressed milk.

Optionally, any of the milk storage configurations described herein may incorporate features to automate one or more aspects of inventory tracking and management. For example, as shown in FIG. 30A, a storage reservoir organizer may comprise an integrated RFID reader 3025 configured to scan a storage reservoir as it enters and/or exits the organizer. As described herein, the RFID reader may be configured to communicate with one or more of a peripheral device and a server having the milk inventory stored thereon, so as to access and update the inventory when the reader scans a storage reservoir comprising an RFID tag. When a user places a new storage reservoir comprising an RFID tag 3030 into the organizer, the RFID reader can read the RFID tag, and subsequently update the inventory with the storage location of the inventory item and/or send an alert to the application to notify the user of the detected change in inventory. Likewise, when a user removes a storage reservoir from the organizer, the scanning of the reservoir's RFID tag with RFID reader can trigger the reader to update the inventory accordingly.

Any milk storage configuration as described herein may also optionally incorporate an integrated sensing unit to automatically determine one or more attributes of the milk placed into the organizer. For example, as shown in FIG. 30B, a storage reservoir organizer may comprise an integrated weight sensor 3035, configured to measure the weight of the stack of milk storage reservoirs disposed on top of the weight sensor. When a storage reservoir is added to or removed from the organizer, the weight sensor can detect the corresponding change in weight, and communicate the information to the inventory or to the application.

Figure 31:
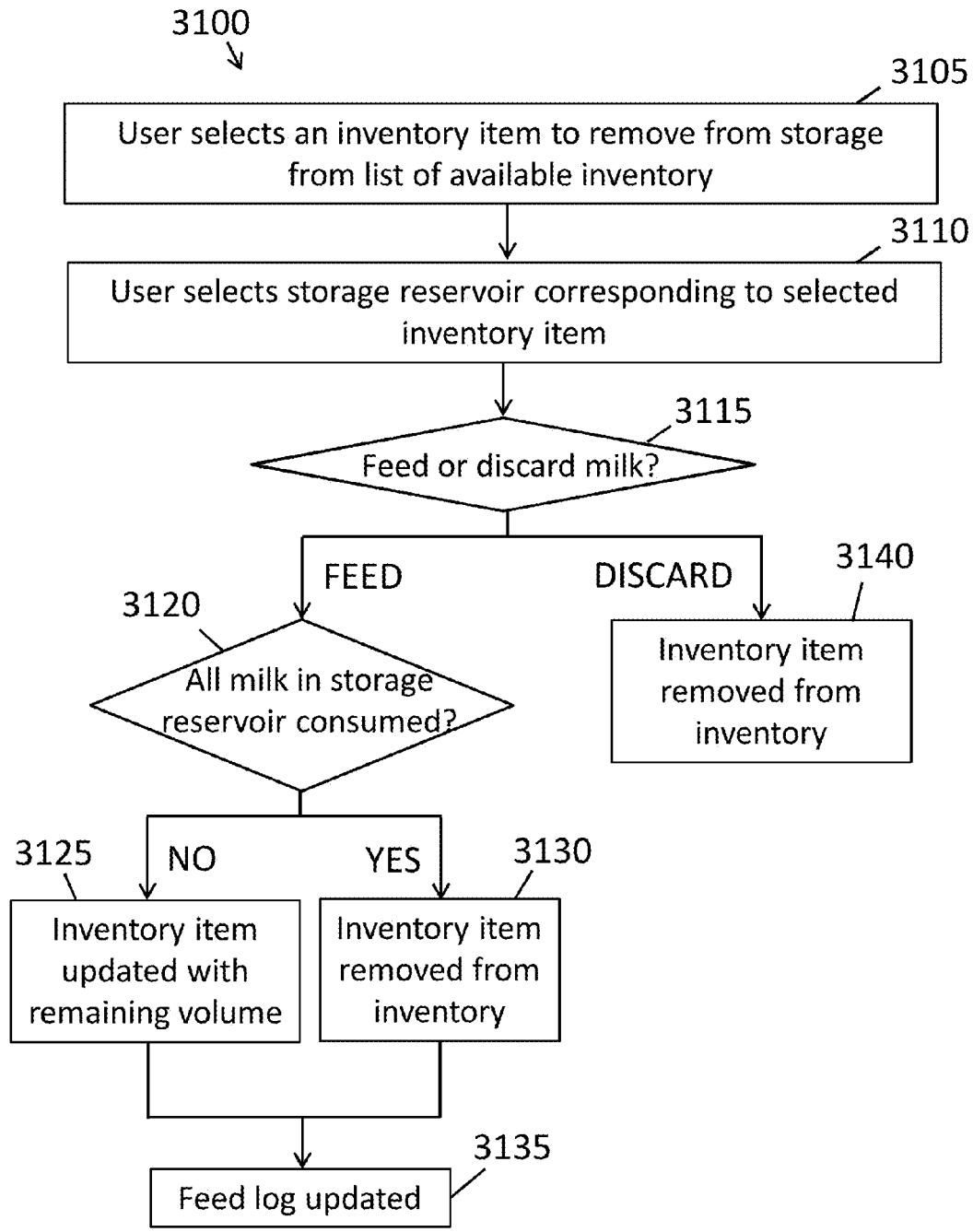
FIG. 31 shows an exemplary method of removing an item from a breast milk inventory.

FIG. 31 shows an exemplary method 3100 of removing an item from a breast milk inventory. In step 3105, a user selects an inventory item to remove from storage from a list of available inventory. For example, an application as described herein may provide the user with the option of viewing the inventory of available milk, and selecting an item to feed or discard. The inventory may optionally present inventory items in order of first-to-feed to last-to-feed, based on an algorithm as described herein; for example, the oldest inventory item that has not "expired" or surpassed a pre-set storage time limit may be displayed at the top of the inventory list. In step 3110, the user selects the milk storage reservoir or container corresponding to the selected inventory item. The user may identify the appropriate storage reservoir using any method described herein (e.g., visual identification of a human-readable code, scanning and visualization of a QR code, etc.).

In step 3115, the application determines whether milk in the selected storage reservoir is to be discarded or fed. This information may be obtained from the user, for example by prompting the user to provide a selection through the application. Alternatively, the application may obtain the information from another device in communication with the peripheral device, such as an RFID reader comprising means for users to provide inputs regarding the destination of a scanned storage reservoir (e.g., buttons to select feed/store/discard). Alternatively, the application may comprise instructions to determine this information automatically. For example, if the selected inventory item has exceeded an expiry threshold as described herein, the application may assume that the item is to be discarded; conversely, if the item has not exceeded the expiry threshold, the application may assume that the item is to be fed.

In step 3120, wherein the inventory item is fed to a child, the system determines whether all of the milk contained in the storage reservoir is consumed. This information may be obtained from the user, for example by prompting the user to provide the volume of remaining milk, if any, through the application. Alternatively, the information may be determined automatically, for example by sensing the volume of the remaining milk with an integrated sensor of the storage reservoir, or by sensing the weight of the remaining milk with an integrated weight sensor of the storage reservoir organizing system as described elsewhere herein.

In step 3125, wherein there is milk remaining in the storage reservoir after the feeding, the inventory is updated to show the remaining volume of milk for the inventory item corresponding to the selected reservoir. In step 3130, wherein all of the milk in the reservoir has been fed, the inventory is updated to remove the inventory item corresponding to the selected reservoir. In step 3135, the feed log as described herein is also updated with information for the feeding session.

In step 3140, wherein the milk in the selected storage reservoir is discarded, the inventory item corresponding to the reservoir is removed from the inventory.

While method 3100 comprises selecting an inventory item from a list provided through the application, the inventory management system may also be configured to allow users to physically select a storage reservoir without referring to the inventory list.

Figure 32:
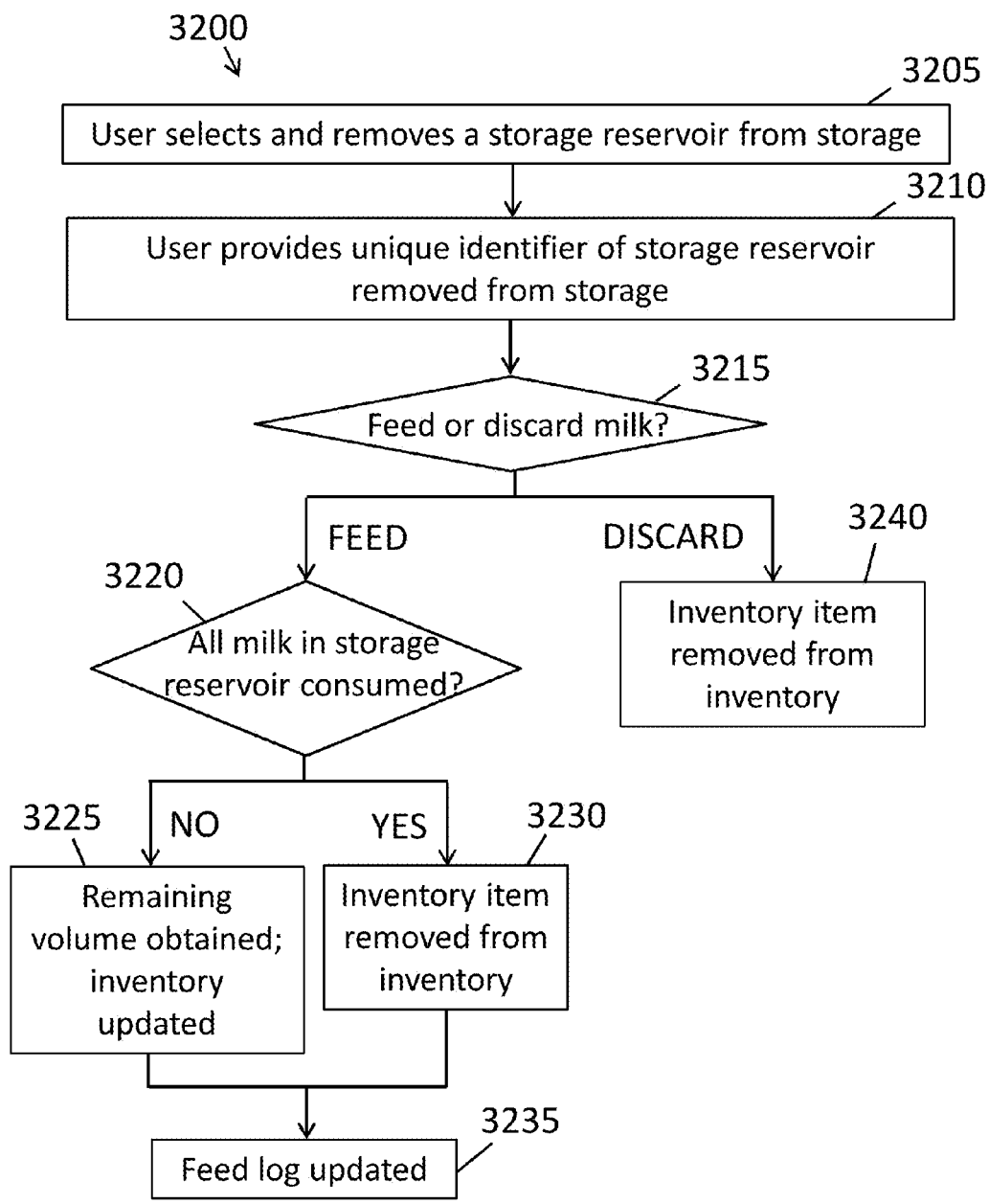
FIG. 32 shows another exemplary method of removing an item from a breast milk inventory.

FIG. 32 shows another exemplary method 3200 of removing an item from a breast milk inventory. In step 3205, a user selects and removes a storage reservoir from storage. In step 3210, the user provides the unique identifier of the selected storage reservoir to the system, for example by manually inputting a user-assigned, human-readable code through the application, printing a label with an identifier using a label printer as described herein, scanning a QR code with the peripheral device, and/or scanning an RFID tag with an RFID reader.

In step 3215, the application determines whether the selected storage reservoir is to be discarded or fed. This information may be obtained from the user, for example by prompting the user to provide a selection through the application. Alternatively, the application may obtain the information from another device in communication with the peripheral device, such as an RFID reader comprising means for users to provide inputs regarding the destination of a scanned storage reservoir (e.g., buttons to select feed/store/discard). Alternatively, the application may comprise instructions to determine this information automatically. For example, if the selected inventory item has exceeded an expiry threshold as described herein, the application may assume that the item is to be discarded; conversely, if the item has not exceeded the expiry threshold, the application may assume that the item is to be fed.

In step 3220, wherein the inventory item is fed to a child, the system determines whether all of the milk contained in the storage reservoir is consumed. This information may be obtained from the user, for example by prompting the user to provide the volume of remaining milk, if any. Alternatively, the information may be determined automatically, for example by sensing the volume of the remaining milk with a sensor of the storage reservoir, or by sensing the weight of the remaining milk with an integrated weight sensor of the storage reservoir organizing system as described elsewhere herein.

In step 3225, wherein there is milk remaining in the storage reservoir after the feeding, the inventory is updated to show the remaining volume of milk for the inventory item corresponding to the selected reservoir. In step 3230, wherein all of the milk in the reservoir has been fed, the inventory is updated to remove the inventory item corresponding to the selected reservoir. In step 3235, the feed log as described herein is also updated with information for the feeding session.

In step 3240, wherein the milk in the selected storage reservoir is discarded, the inventory item corresponding to the reservoir is removed from the inventory.

Method 3200 can allow users to remove items from the milk inventory without interacting with the application. The unique identifier may comprise a machine-readable identifier as described herein, and a machine capable of recognizing the identifier, such as a barcode reader or an RFID reader, can be disposed in a location near the refrigerator and/or freezer. The user can simply remove a storage reservoir from its storage location and scan the identifier of the reservoir with the machine to automatically update the inventory. Such a configuration can allow persons who do not have access to the application, such as caregivers, to update the milk inventory automatically as they feed or discard stored milk.

For example, wherein the unique identifier comprises an RFID tag, an RFID reader as described herein may be disposed at a convenient location for scanning the storage reservoirs (e.g., attached to the door of the refrigerator/freezer, placed on a kitchen counter, etc.). A user can remove a storage reservoir from storage and scan the reservoir with the RFID reader. The RFID reader can be configured to communicate with the peripheral device comprising the application for the pump system, for example via a wireless connection. When the reader scans an RFID tag, the reader can alert the application that the storage reservoir corresponding to the recognized RFID tag has been removed from storage. As described herein, the application may apply an algorithm to automatically determine whether the identified milk is fed or discarded, or the RFID reader may comprise a user input that allows the user to indicate whether the milk is to be fed or discarded. The inventory may be updated accordingly. Optionally, updates to the inventory may be withheld until an authorized user of the pump system approves the updates via the application. For example, when a storage reservoir corresponding to an item in the inventory is scanned, the application may alert the authorized user of the system that a change to the inventory has been detected, and ask the user to confirm that the inventory update is correct. Such alerts may be presented to the user in real-time, or periodically at set time-intervals (e.g., every day at 7:00 pm).

The steps of methods 3100 and 3200 are provided as examples of methods of removing an item from a milk inventory in accordance with embodiments. A person of ordinary skill in the art will recognize many variations and modifications of methods 3100 and 3200 based on the disclosure provided herein. For example, some steps may be added or removed. One or more steps may be performed in a different order than as illustrated in FIGS. 31 and 32. Some of the steps may comprise sub-steps. Many of the steps may be repeated as many times as appropriate or necessary.

After a user has selected a storage reservoir as in step 3110 of method 3100 or step 3210 of method 3200, the user may decide to take an action other than feeding or discarding the milk contained in the reservoir. For example, the user may decide to change the storage location of the reservoir. The application may provide such an action as a user-selectable option when an inventory item is selected by a user or identified via the unique identifier. Alternatively, the application may obtain the information from another device in communication with the peripheral device, such as an RFID reader. For example, a user may remove a storage reservoir from the freezer, select "refrigerator" as the destination on the RFID reader and proceed to scan the reservoir with the reader. The application may then recognize that the reservoir is being moved from the freezer to the refrigerator, and accordingly change the storage location associated with the inventory item. The system may be further configured to allow and keep track of other user actions (e.g., transfer of milk from a selected reservoir to another).

An inventory management application for tracking and managing breast milk inventory may be provided via the peripheral device, and may be programmed with various features and functionalities to facilitate inventory management by a user. As described herein, the application may be programmed to prompt the user to record additions to or removals from the inventory, or record volumes of consumed milk. Optionally, the application may provide additional features to further facilitate the user workflow. The application may be programmed to provide a daily reminder or trigger message to recommend one or more inventory-related actions to the user. For example, the application may be programmed to perform a check of the inventory every evening, and recommend that the user move some inventory from the freezer to the refrigerator if the inventory shows little or no milk stored in the refrigerator. The application may be programmed to periodically check the inventory for items expiring within a short window of time (e.g., within 24 hours), and remind the user to feed this milk within said window of time and/or move the inventory item from the freezer to the refrigerator such that the milk may be fed.

The expressed milk inventory may be stored onto a remote or cloud server, so that the inventory may be accessed by users given permission. For example, a child caregiver may update the inventory appropriately as milk is fed to the infant. A pediatrician may also be able to access the inventory to track milk production and content, in order to determine whether the infant is receiving the appropriate nutrition.

Experimental Data

Figure 15:
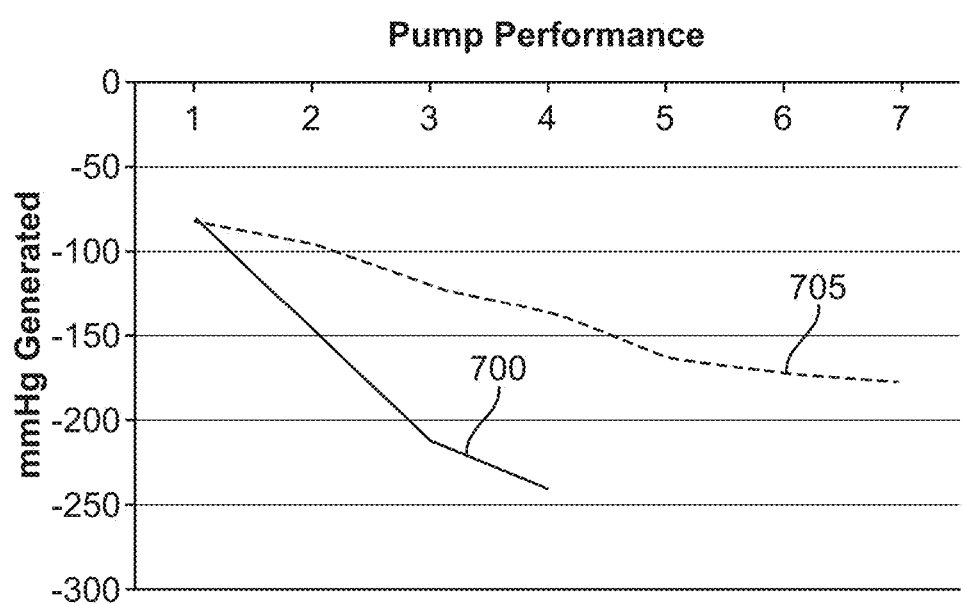
FIG. 15 is a graph illustrating the pump performance of an exemplary pumping device compared to a commercial device, in accordance with embodiments.
Figure 16:
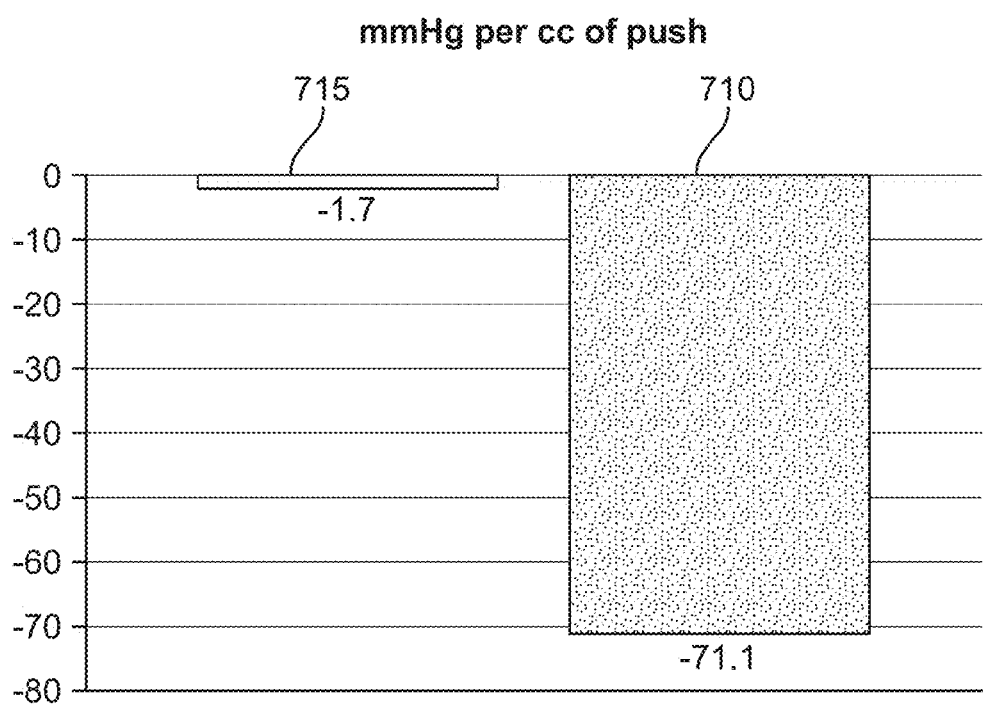
FIG. 16 is a graph illustrating the pumping efficiency of an exemplary pumping device compared to a commercial device, in accordance with embodiments.

FIGS. 15 and 16 illustrate experimental pumping data obtained from a commercial breast pump device and an exemplary embodiment of the present invention. The exemplary embodiment utilized an incompressible fluid for pumping and had a maximum hydraulic fluid volume of 4 cc, while the commercial device utilized air for pumping and had a maximum volume of 114 cc.

FIG. 15 illustrates a graph of the pump performance as quantified by vacuum pressure generated per run. For the exemplary embodiment, pressure measurements were taken for 1 cc, 2 cc, 3 cc, and 4 cc of fluid volume displaced by the pump, with the run number corresponding to the volume in cc. For the commercial device, measurements were taken with the pump set to one of seven equally incremented positions along the vacuum adjustment gauge representing 46 cc, 57 cc, 68 cc, 80 cc, 91 cc, 103 cc, and 114 cc of fluid volume displaced by the pump, respectively, with the run number corresponding to the position number. Curve 700 corresponds to the exemplary embodiment and curve 705 corresponds to the commercial device. The exemplary embodiment generated higher levels of vacuum pressure per displacement volume compared to the commercial device, with maximum vacuum pressures of −240.5 mmHg and −177.9 mmHg, respectively.

FIG. 16 illustrates a graph of the pump efficiency as measured by the maximum vacuum pressure per maximum volume of fluid displaced, with bar 710 corresponding to the exemplary embodiment and bar 715 corresponding to the commercial device. The exemplary embodiment demonstrated a 42-fold increase in pumping efficiency compared to the commercial device, with efficiencies of −71.1 mmHg/cc and −1.7 mmHg/cc, respectively.

The various techniques described herein may be partially or fully implemented using code that is storable upon storage media and computer readable media, and executable by one or more processors of a computer system. Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, solid state drives (SSD) or other solid state storage devices, or any other medium which can be used to store the desired information and which can be accessed by the a system device. Based on the disclosure and teachings provided herein, a person of ordinary skill in the art will appreciate other ways and/or methods to implement the various embodiments.

It shall be understood that different aspects of the invention can be appreciated individually, collectively, or in combination with each other. Suitable elements or features of any of the embodiments described herein can be combined or substituted with elements or features of any other embodiment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for quantifying expressed milk from a human breast, said system comprising:
   a breast milk expression device configured to express milk from the breast;
   a reservoir fluidly coupled to the breast milk expression device and configured to collect the expressed breast milk;
   a sensor unit integrated with the reservoir or the breast milk expression device and configured to quantify one or more attributes of the expressed breast milk; and a peripheral device in communication with the sensor unit, wherein the peripheral device is configured to obtain a unique identifier for the expressed breast milk and associate the unique identifier with the one or more attributes of the expressed breast milk.

2. The system of claim 1, wherein the sensor unit is configured to automatically quantify the one or more attributes of the expressed breast milk during expression of the breast milk.

3. The system of claim 1, wherein the sensor unit is configured to sense a change in an amount of milk contained within the reservoir or a flow of milk past the sensor unit to quantify the one or more attributes of the expressed breast milk.

4. The system of claim 1, further comprising a separate sensor unit in communication with the peripheral device, the separate sensor unit configured to quantify one or more attributes of the expressed breast milk after the expressed breast milk has been collected in the reservoir.

5. The system of claim 1, wherein the one or more attributes of the expressed breast milk quantified by the sensor unit comprise a volume of the expressed breast milk collected in the reservoir.

6. The system of claim 1, wherein the one or more attributes of the expressed breast milk quantified by the sensor unit comprise a composition of the expressed milk, and wherein the sensor unit is configured to quantify a relative amount of one or more compounds present in the expressed breast milk.

7. The system of claim 1, wherein the breast milk expression device is configured to generate pump session data comprising a start time of a pump session and an end time of the pump session, and wherein the peripheral device is further configured to associate the unique identifier with the pump session data.

8. The system of claim 1, wherein the peripheral device is further configured with instructions to update an inventory of expressed breast milk in response to the association of the unique identifier with the one or more attributes of the expressed breast milk.

9. The system of claim 8, wherein the peripheral device is configured to generate an inventory item in the inventory of expressed breast milk corresponding to the unique identifier.

10. The system of claim 1, wherein the unique identifier comprises one or more of a human-readable code, a barcode, a Quick Response (QR) code, and a radio-frequency identification (RFID) tag.

11. The system of claim 1, further comprising a label printer for generating a label for the reservoir or a storage reservoir containing the expressed breast milk, wherein the label printer is configured to communicate with the peripheral device and provide the unique identifier to the peripheral device when the label is generated.

12. A method for quantifying expression of breast milk from a human breast, said method comprising:
providing a breast milk expression device for expressing breast milk from a human breast and a reservoir for collecting the expressed breast milk;
quantifying one or more attributes of the expressed breast milk with a sensor unit integrated with the reservoir or the breast milk expression device;
generating pump session data comprising a start time of expression of the breast milk and an end time of the expression;
obtaining a unique identifier for the expressed breast milk;
digitally associating the unique identifier with the pump session data and the one or more attributes of the expressed breast milk; and
updating a pump session log with the unique identifier and the associated pump session data and the one or more attributes of the expressed breast milk, wherein the pump session log is stored on a peripheral device in communication with the breast milk expression device.

13. The method of claim 12, wherein quantifying comprises automatically quantifying the one or more attributes of the expressed breast milk during expression of the breast milk.

14. The method of claim 12, wherein quantifying comprises quantifying the one or more attributes of the expressed breast milk after the expressed breast milk has been collected in the reservoir.

15. The method of claim 12, wherein quantifying comprises quantifying a volume of the expressed breast milk collected in the reservoir.

16. The method of claim 12, wherein quantifying comprises quantifying a relative amount of one or more compounds present in the expressed breast milk.

17. The method of claim 12, further comprising determining a volume of the expressed breast milk remaining in the reservoir after at least a portion of the expressed breast milk has been fed to a child.

18. The method of claim 17, further comprising updating a feed log stored on the peripheral device to add feeding session data comprising a time of feeding and a volume of the expressed breast milk consumed by the child.

19. The method of claim 12, further comprising sensing a change in an amount of milk contained within the reservoir or a flow of milk past the sensor unit to quantify the one or more attributes of the expressed breast milk.

20. The method of claim 12, wherein the unique identifier comprises a human-readable code, and wherein obtaining the unique identifier comprises prompting a user to input the human-readable code via an application of the peripheral device.

21. The method of claim 12, wherein the unique identifier comprises a machine-readable code, and wherein obtaining the unique identifier comprises reading the machine-readable code with a machine configured to recognize the machine-readable code.

22. The method of claim 21, wherein the machine-readable code comprises a radio-frequency identification (RFID) tag, and wherein obtaining the unique identifier comprises scanning the RFID tag with an RFID reader in communication with the peripheral device.

23. The method of claim 12, further comprising updating an inventory of expressed breast milk to add a new inventory item corresponding to the unique identifier.

24. The method of claim 12, further comprising transferring the expressed milk from the reservoir to another storage reservoir comprising the unique identifier.

25. A system for managing an inventory of expressed breast milk, said system comprising:
an inventory management database storing the inventory of expressed breast milk, the inventory comprising one or more inventory items; and
a computing device configured with instructions to:
receive pump session data from a breast milk expression device, the pump session data comprising a start time of a pump session and an end time of the pump session;

receive user input indicating whether breast milk expressed during the pump session is to be stored, discarded, or fed; and update the inventory of expressed breast milk in response to receiving the user input indicating that the breast milk expressed during the pump session is to be stored, wherein updating the inventory of expressed breast milk comprises obtaining a unique identifier for the expressed breast milk expressed during the pump session, and adding or updating an inventory item associated with the unique identifier.

26. The system of claim 25, wherein the computing device is further configured with instructions to receive milk attribute data from a sensing unit integrated with the reservoir or the breast milk expression device, the milk attribute data comprising one or more attributes of the expressed breast milk, and wherein updating the inventory of expressed breast milk further comprises digitally coupling the unique identifier with the milk attribute data.

27. The system of claim 25, wherein the computing device is further configured with instructions to sort the one or more inventory items in the inventory in order of first-to-feed to last-to-feed.

28. The system of claim 25, wherein the computing device is further configured with instructions to display the inventory to a user.

29. The system of claim 25, wherein the computing device is further configured with instructions to locally store the inventory management database.

30. The system of claim 25, further comprising a server in communication with the computing device, the server configured to remotely store the inventory management database.

31. The system of claim 25, wherein the unique identifier comprises a Quick Response (QR) code, and wherein the computing device is further configured to recognize the QR code.

32. The system of claim 25, wherein the unique identifier comprises a radio-frequency identification (RFID) tag, and wherein the system further comprises an RFID reader in communication with the computing device, the RFID reader configured to recognize the RFID tag and provide identifier information to the computing device.

33. The system of claim 25, further comprising a reservoir organizer configured to store a plurality of reservoirs in a stacked configuration, wherein the organizer comprises a top opening configured to receive the plurality of reservoirs one at a time and a bottom opening configured to allow withdrawal of a reservoir disposed at the bottom of a stack of the plurality of reservoirs, thereby facilitating a first-in, first-out system of organization.

34. The system of claim 33, wherein the reservoir organizer further comprises an integrated RFID reader configured to scan an RFID tag disposed on a storage reservoir as the storage reservoir enters or exits the reservoir organizer, wherein the RFID reader communicates detected scans to the computing device.

35. The system of claim 33, wherein the reservoir organizer further comprises an integrated weight sensor configured to measure a weight of the stack of the plurality of reservoirs, wherein the weight sensor communicates detected changes in the weight of the stack to the computing device.

36. A method for managing an inventory of expressed breast milk, said method comprising:

receiving pump session data from a breast milk expression device, the pump session data comprising a start time of a pump session and an end time of the pump session;

receiving user input indicating whether the breast milk expressed during the pump session is to be stored, discarded, or fed; and updating the inventory of expressed breast milk in response to receiving the user input indicating that the breast milk expressed during the pump session is to be stored;

wherein updating the inventory of expressed breast milk comprises obtaining a unique identifier for the expressed breast milk expressed during the pump session, and adding or updating an inventory item associated with the unique identifier.

37. The method of claim 36, further comprising receiving milk attribute data from a sensing unit integrated with the reservoir or the breast milk expression device, the milk attribute data comprising one or more attributes of breast milk expressed during the pump session.

38. The method of claim 37, wherein updating the inventory of expressed breast milk further comprises digitally coupling the unique identifier with the milk attribute data.

39. The method of claim 36, further comprising receiving a unique identifier associated with an inventory item to be updated or removed from the inventory of expressed breast milk, and identifying the inventory item associated with the unique identifier.

40. The method of claim 36, further comprising displaying, via an inventory management application of the computing device, a list of inventory items in the inventory, and prompting a user to select the inventory item to update or remove from the list of inventory items.

41. The method of claim 40, further comprising sorting the list of inventory items in order of first-to-feed to last-to-feed.

42. The method of claim 41, wherein sorting comprises sorting in order of date of expression of the expressed breast milk, wherein an inventory item corresponding to expressed breast milk with an oldest date of expression is determined to be the first-to-feed, and an inventory item corresponding to expressed breast milk with a newest date of expression is determined to be the last-to-feed.

43. The method of claim 41, wherein the method further comprises providing, via the inventory management application of the computing device, a visual display of a plurality of reservoirs corresponding to a plurality of inventory items in the inventory, the visual display identifying the first-to-feed inventory item.

44. The method of claim 40, further comprising indicating an inventory item as expired if a difference between a current date and a date of expression of the expressed breast milk corresponding to the inventory item exceeds a predetermined expiry threshold.

45. The method of claim 40, wherein removing the inventory item comprises removing the inventory item from the inventory in response to a determination that there is no remaining milk in the reservoir.

46. The method of claim 40, wherein updating the inventory item comprises updating information associated with the inventory item in response to a determination that there is remaining milk in the reservoir.

47. The method of claim 46, wherein updating information associated with the inventory item comprises updating a volume of the expressed breast milk contained in the reservoir.

48. The method of claim 46, wherein updating information associated with the inventory item comprises updating a storage location of the reservoir.

49. The method of claim 36, wherein the inventory is locally stored on the computing device.

50. The method of claim 36, wherein the inventory is remotely stored on a server in communication with the computing device.

51. The method of claim 36, wherein the unique identifier comprises a radio-frequency identification (RFID) tag, and wherein the method further comprises scanning the RFID tag with an RFID reader in communication with the computing device.

* * * * *